US007612060B2

(12) United States Patent
Aya et al.

(10) Patent No.: US 7,612,060 B2
(45) Date of Patent: Nov. 3, 2009

(54) TRIAZOLES AND METHODS OF USE

(75) Inventors: Toshihiro Aya, Thousand Oaks, CA (US); Guolin Cai, Thousand Oaks, CA (US); Jian J. Chen, Newbury Park, CA (US); Derin D'Amico, Newbury Park, CA (US); Thomas Nguyen, Thousand Oaks, CA (US); Wenyuan Qian, Camarillo, CA (US)

(73) Assignee: Amgen Inc., Thousand Oaks, CA (US)

( * ) Notice: Subject to any disclaimer, the term of this patent is extended or adjusted under 35 U.S.C. 154(b) by 391 days.

(21) Appl. No.: 11/247,046

(22) Filed: Oct. 11, 2005

(65) Prior Publication Data

US 2006/0100213 A1 May 11, 2006

Related U.S. Application Data

(60) Provisional application No. 60/618,893, filed on Oct. 13, 2004.

(51) Int. Cl.
  *C07D 403/00* (2006.01)
  *C07D 401/00* (2006.01)
  *C07D 413/00* (2006.01)
  *A01N 43/46* (2006.01)
  *A61K 31/535* (2006.01)
  *A61K 31/497* (2006.01)

(52) U.S. Cl. ............... 514/217.08; 544/366; 544/360; 544/370; 544/363; 544/359; 544/369; 514/235.5; 514/252.17; 514/254.04; 514/254.05

(58) Field of Classification Search ............ None
See application file for complete search history.

(56) References Cited

FOREIGN PATENT DOCUMENTS

| WO | WO 95/14683 | 6/1995 |
|---|---|---|
| WO | WO 97/25315 | 7/1997 |
| WO | WO 02/076964 A1 | 10/2002 |
| WO | WO 2004/083173 A2 | 9/2004 |
| WO | WO 2004/092116 A1 | 10/2004 |
| WO | WO 2004/092164 A1 | 10/2004 |

OTHER PUBLICATIONS

Chawla et al., "Challenges in Polymorphism of Pharmaceuticals", CRIPS vol. 5, No. 1, Jan.-Mar. 2004 (4 Pages).*
Newman et al., "Solid-state analysis of the active pharmaceutical ingredient in drug products", DDT vol. 8, No. 19, Oct. 2003, p. 898-905.*
Cole et al., Bioorg. Med. Chem. Lett, 2008, doi:10.1016/j.bmcl.2008.11.005.*
Su, Dai-Shi, et al., "Discovery of a Potent, Non-peptide Bradykinin $B_1$ Receptor Antagonist," *J. Am. Chem. Soc.*, vol. 125, No. 25, pp. 7516-7517, 2003.

* cited by examiner

*Primary Examiner*—Joseph K. McKane
*Assistant Examiner*—Sun Jae Y Loewe
(74) *Attorney, Agent, or Firm*—Rekha P. Bansal

(57) ABSTRACT

Selected compounds are effective for treatment of pain and diseases, such as inflammation mediated diseases. The invention encompasses novel compounds, analogs, prodrugs and pharmaceutically acceptable derivatives thereof, pharmaceutical compositions and methods for prophylaxis and treatment of diseases and other maladies or conditions involving pain, inflammation, and the like. The subject invention also relates to processes for making such compounds as well as to intermediates useful in such processes.

8 Claims, No Drawings

TRIAZOLES AND METHODS OF USE

CROSS-REFERENCE TO RELATED APPLICATIONS

This application claims the benefit under 35 U.S.C. 119(e) of U.S. Provisional Application Ser. No. 60/618,893, filed on Oct. 13, 2004, the disclosure of which is incorporated herein by reference in its entirety.

BACKGROUND OF THE INVENTION

1. Field of the Invention

This invention is in the field of pharmaceutical agents and specifically relates to compounds, compositions, uses and methods for treating inflammation-related disorders, including pain.

2. State of the Art

More than two million people in the United States alone are incapacitated by chronic pain on any given day (T. Jessell & D. Kelly, Pain and Analgesia in PRINCIPLES OF NEURAL SCIENCE, third edition (E. Kandel, J. Schwartz, T. Jessell, eds., (1991)). Unfortunately, current treatments for pain are only partially effective, and many cause lifestyle altering, debilitating, and/or dangerous side effects. For example, non-steroidal anti-inflammatory drugs ("NSAIDs") such as aspirin, ibuprofen, and indomethacin are moderately effective against inflammatory pain but they are also renally toxic, and high doses tend to cause gastrointestinal irritation, ulceration, bleeding, increased cardiovascular risk, and confusion. Patients treated with opioids frequently experience confusion and constipation, and long-term opioid use is associated with tolerance and dependence. Local anesthetics such as lidocaine and mixelitine simultaneously inhibit pain and cause loss of normal sensation. In addition, when used systemically, local anesthetics are associated with adverse cardiovascular effects. Thus, there is currently an unmet need in the treatment of chronic pain.

Pain is a perception based on signals received from the environment and transmitted and interpreted by the nervous system (for review, see M. Millan, Prog. Neurobiol. 57:1-164 (1999)). Noxious stimuli such as heat and touch cause specialized sensory receptors in the skin to send signals to the central nervous system ("CNS"). This process is called nociception, and the peripheral sensory neurons that mediate it are nociceptors. Depending on the strength of the signal from the nociceptor(s) and the abstraction and elaboration of that signal by the CNS, a person may or may not experience a noxious stimulus as painful. When one's perception of pain is properly calibrated to the intensity of the stimulus, pain serves its intended protective function. However, certain types of tissue damage cause a phenomenon, known as hyperalgesia or pronociception, in which relatively innocuous stimuli are perceived as intensely painful because the person's pain thresholds have been lowered. Both inflammation and nerve damage can induce hyperalgesia. Thus, persons afflicted with inflammatory conditions, such as sunburn, osteoarthritis, colitis, carditis, dermatitis, myositis, neuritis, inflammatory bowel disease, collagen vascular diseases (which include rheumatoid arthritis and lupus) and the like, often experience enhanced sensations of pain. Similarly, trauma, surgery, amputation, abscess, causalgia, collagen vascular diseases, demyelinating diseases, trigeminal neuralgia, cancer, chronic alcoholism, stroke, thalamic pain syndrome, diabetes, herpes infections, acquired immune deficiency syndrome ("AIDS"), toxins and chemotherapy cause nerve injuries that result in pain.

As the mechanisms by which nociceptors transduce external signals under normal and hyperalgesic conditions become better understood, processes implicated in hyperalgesia can be targeted to inhibit the lowering of the pain threshold and thereby lessen the amount of pain experienced.

Bradykinin (BK) and the related peptide, kallidin (Lys-BK) mediate the physiological actions of kinins on the cardiovascular and renal systems. However, the active peptides, BK and kallidin, are quickly degraded by peptidases in the plasma and other biological fluids and by those released from a variety of cells, so that the half-life of BK in plasma is reported to be approximately 17 seconds (1). BK and kallidin are rapidly metabolized in the body by carboxypeptidase N, which removes the carboxyterminal arginine residue to generate des-Arg BK or des-Arg kallidin. Des-Arg-kallidin is among the predominant kinins in man and mediates the pathophysiological actions of kinins in man. In addition to being a very potent proinflammatory peptide, des-Arg-BK or des-Arg-kallidin is known to induce vasodilation, vascular permeability, and bronchoconstriction (for review, see Regoli and Barabe, Pharmacological Rev, 32(1), 1-46 (1980)). In addition, des-Arg-BK and des-Arg-kallidin appear to be particularly important mediators of inflammation and inflammatory pain as well as being involved in the maintenance thereof. There is also a considerable body of evidence implicating the overproduction of des-Arg-kallidin in conditions in which pain is a prominent feature such as septic shock, arthritis, angina, and migraine.

The membrane receptors that mediate the pleiotropic actions of kinins are of two distinct classes, designated B1 and B2. Both classes of receptors have been cloned and sequenced from a variety of species, including man (Menke, et al, J. Biol. Chem. 269, 21583-21586 (1994); Hess et al, Biochem. Biophys. Res. Commun. 184, 260-268 (1992)). They are typical G protein coupled receptors having seven putative membrane spanning regions. In various tissues, BK receptors are coupled to every known second messenger. B2 receptors, which have a higher affinity for BK, appear to be the most prevalent form of bradykinin receptor. Essentially all normal physiological responses and many pathophysiological responses to bradykinin are mediated by B2 receptors.

B1 receptors, on the other hand, have a higher affinity for des-Arg-BK compared with BK, whereas des-Arg-BK is inactive at B2 receptors. In addition, B1 receptors are not normally expressed in most tissues. Their expression is induced upon injury or tissue damage as well as in certain kinds of chronic inflammation or systemic insult (F. Marceau, et al., Immunopharmacology, 30, 1-26 (1995)). Furthermore, responses mediated by B1 receptors are up-regulated from a null level following administration of bacterial lipopolysaccharide (LPS) or inflammatory cytokines in rabbits, rats, and pigs.

The pain-inducing properties of kinins coupled with the inducible expression of B1 receptors make the B1 receptor an interesting target in the development of anti-inflammatory, antinociceptive, antihyperalgesic and analgesic agents that may be directed specifically at injured tissues with minimal actions in normal tissues.

Certain compounds have been described as bradykinin antagonists. WO 03/07958, published 30 Jan. 2003, describes tetrahydroquinoxalines. Dihydroquinoxalinones are described in a JACS communication.

Piperazine-2,3,5-triones are described in Tet. Lett., 40, 7557-7560 (1999). European application 641779, published 8 Mar. 1995, describes 3,6-dioxopiperazines as platelet aggregation inhibitors.

Clearly, there is a need for new, safe and effective treatments for inflammation and pain. Such agents are provided in the present invention.

DETAILED DESCRIPTION OF THE INVENTION

In one aspect, this invention is directed to a compound of Formula (I):

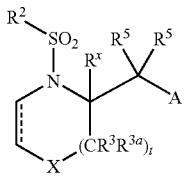

(I)

wherein:

t is 0, 1 or 2;

X is selected from —NH—, —S—, —O—, —NR$^d$—, —NR$^e$—, or —NR$^g$—;

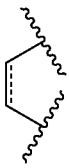

is selected from:

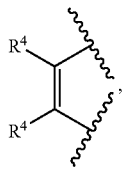 , 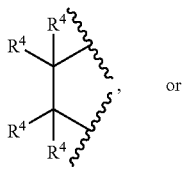 , or 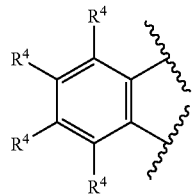

A is a group of formula (a) or (b):

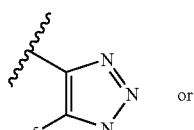

(a)

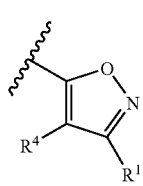

(b)

where:

R$^1$ is -(alkylene)n-R where n is 0 or 1 and R is a 5-, 6-, 7-, or 8-membered saturated, partially saturated or unsaturated monocyclic, a saturated, partially saturated or unsaturated 8-, 9-, 10- or 11-membered bicyclic, or 12-, 13-, 14- or 15-membered tricyclic hydrocarbon ring containing 0, 1, 2, 3 or 4 atoms selected from N, O and S, wherein the carbon and sulfur atoms of the ring are substituted by 0, 1 or 2 oxo groups and the ring is substituted by 0, 1, 2 or 3 substituents selected from R$^6$, R$^7$ or R$^8$ independently selected from basic moieties, and additionally substituted by 0, 1, 2 or 3 substituents selected from R$^6$, R$^7$ and R$^8$ which are selected from R$^g$, C$_{1-8}$alkyl, C$_{1-4}$haloalkyl, hydroxyalkyl, cyano, nitro, C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$—SR$^a$, —S(=O)R, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, N(R$^a$)C(=O)OR$^b$, —N(R$^a$)C(=O)NR$^a$R$^a$, —N(R$^a$)C(=NR$^a$)NR$^a$R$^a$, —N(R$^a$)S(R$^a$)S(=)$_2$NR$^a$R$^a$, —NR$^a$C$_{2-6}$alkylNR$^a$R$^a$ and —NR$^a$C$_{2-6}$alkylOR$^a$, and the ring is additionally substituted by 0, 1, 2, 3, 4 or 5 substituents selected from R$^6$, R$^7$, R$^8$, R$^9$ and R$^{10}$ which are independently selected from Br, Cl, F and I;

R$^2$ is a saturated, partially saturated or unsaturated 5-, 6- or 7-membered monocyclic or 6-, 7-, 8-, 9-, 10- or 11-membered bicyclic hydrocarbon ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from R$^e$, R$^g$, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkyl OR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkyl OR$^a$, and the ring is additionally substituted by 0, 1, 2, 3, 4 or 5 substituents independently selected from Br, Cl, F and I;

R$^3$, R$^{3a}$, R$^4$ and R$^5$ are independently in each instance selected from H, C$_{1-3}$alkyl, C$_{1-3}$haloalkyl, —OH, F, Cl, Br and I; or R$^3$ and R$^{3a}$ together form oxo;

R$^x$ is selected from H, F, Cl, (C$_1$-C$_3$)haloalkyl, and (C$_1$-C$_3$)alkyl;

R$^a$ is independently, at each instance, H or R$^b$;

R$^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl.

R$^d$ is independently at each instance C$_{1-8}$alkyl, C$_{1-4}$haloalkyl, halo, cyano, nitro, —C(=O)R$^a$, —C(=O)OR, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

R$^e$ is independently at each instance C$_{1-6}$alkyl substituted by 0, 1, 2 or 3 substituents independently selected from R$^d$ and additionally substituted by 0 or 1 substituents selected from R$^g$; and $R^g$ is independently at each instance a saturated, partially saturated or unsaturated 5-, 6- or 7-membered monocyclic or 6-, 7-, 8-, 9-, 10- or 11-membered bicyclic hydrocarbon ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alky10$R^a$—S$R^a$, —S(=O)R, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and the ring is additionally substituted by 0, 1, 2, 3, 4 or 5 substituents independently selected from Br, Cl, F and I; or or any pharmaceutically-acceptable salt or hydrate thereof.

In one embodiment, in conjunction with any of the below embodiments, $R^1$ is a saturated, partially saturated or unsaturated 8-, 9-, 10- or 11-membered bicyclic or 12-, 13-, 14- or 15-membered tricyclic hydrocarbon ring containing 0, 1, 2, 3 or 4 atoms selected from N, O and S, wherein the carbon and sulfur atoms of the ring are substituted by 0, 1 or 2 oxo groups and the ring is substituted by $R^6$, $R^7$ or $R^8$ independently selected from basic moieties, and additionally substituted by 0, 1, 2 or 3 substituents selected from $R^6$, $R^7$ and $R^8$ which are selected from $R^g$, $C_{1-8}$alkyl, $C_{1-4}$haloalkyl, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)R, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, N($R^a$)C(=N$R^a$)N$R^aR^a$, —N($R^a$)S(=O)$_2R^b$, —N($R^a$)S(=O)$_2$N$R^aR^a$, —N$R^a C_{2-6}$alkylN$R^aR^a$ and —N$R^aC_{2-6}$alkylO$R^a$, and the ring is additionally substituted by 0, 1, 2, 3, 4 or 5 substituents selected from $R^6$, $R^7$, $R^8$, $R^9$ and $R^{10}$ which are independently selected from Br, Cl, F and I.

In another embodiment, in conjunction with any of the below embodiments, $R^1$ is a saturated, partially saturated or unsaturated 8-, 9-, 10- or 11-membered bicyclic or 12-, 13-, 14- or 15-membered tricyclic hydrocarbon ring containing 0, 1, 2, 3 or 4 atoms selected from N, O and S, wherein the carbon and sulfur atoms of the ring are substituted by 0, 1 or 2 oxo groups and the ring is substituted by 0, 1, 2 or 3 substituents selected from $R^6$, $R^7$ and $R^8$ which are selected from $R^g$, $C_{1-8}$alkyl, $C_{1-4}$haloalkyl, cyano, nitro, basic moiety, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O) N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and the ring is additionally substituted by 0, 1, 2, 3, 4 or 5 substituents selected from $R^6$, $R^7$, $R^8$, $R^9$ and $R^{10}$ which are independently selected from Br, Cl, F and I.

In another embodiment, in conjunction with any of the below embodiments, $R^1$ is -(alkylene)n-R where n is 0 or 1 and R is a 5-, 6-, 7-, or 8-membered saturated, partially saturated or unsaturated monocyclic hydrocarbon ring containing 0, 1, 2, 3 or 4 atoms selected from N, O and S, wherein the carbon and sulfur atoms of the ring are substituted by 0, 1 or 2 oxo groups and the ring is substituted by 0, 1, 2 or 3 substituents selected from $R^6$, $R^7$ and $R^8$ which are selected from $R^g$, $C_{1-8}$alkyl, $C_{1-4}$haloalkyl, cyano, nitro, basic moiety, —C(=O)$R^b$, —C(=O)N$R^aR^b$, —C(=N$R^a$)N$R^aR^a$, —O$R^a$, —OC(=O)$R^a$, —OC(=O)N$R^aR^a$, —OC(=O)N ($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O) $R^b$, —N($R^a$)C(=O)O$R^b$, —N($R^a$)C(=O)N$R^aR^a$, N($R^a$)C (=N$R^a$)N$R^aR^a$, —N($R^a$)S(=O)$_2R^b$, —N($R^a$)S(=O)$_2$ N$R^aR^a$, —N$R^aC_{2-6}$alkylN$R^aR^a$ and —N$R^aC_{2-6}$alkylO$R^a$, and the ring is additionally substituted by 0, 1, 2, 3, 4 or 5 substituents selected from $R^6$, $R^7$, $R^8$, $R^9$ and $R^{10}$ which are independently selected from Br, Cl, F and I.

In another embodiment, in conjunction with any of the above or below embodiments, the basic moieties are independently selected from amino, cycloalkylamino$C_{1-6}$alkyl, cycloalkyl$C_{1-6}$alkylamino$C_{1-6}$alkyl, heterocyclylamino$C_{1-6}$ alkyl, heterocyclyl$C_{1-6}$alkylamino$C_{1-6}$alkyl, arylamino$C_{1-6}$ alkyl, aryl$C_{1-6}$alkylamino$C_{1-6}$alkyl, $C_{1-6}$-alkylamino-$C_{1-6}$-alkoxy, $C_{1-6}$-alkylamino-$C_{1-6}$-alkoxy-$C_{1-6}$-alkoxy, amino$C_{1-6}$ alkoxy, amino-$C_{1-6}$alkyl, $C_{1-6}$alkylamino$C_{1-6}$alkyl, $C_{1-4}$-alkylamino-$C_{2-6}$-alkenyl, 5-8 membered nitrogen-containing heterocyclyl-$C_{2-6}$-alkenyl, heterocyclyl-$C_{1-6}$alkylamino$C_{2-6}$alkyl, 5-6 membered heterocyclyloxy, 4-6 membered nitrogen-containing heterocyclyl and 5-7 membered nitrogen-containing heterocyclyl-alkyl; and wherein each of said basic moieties is substituted by 0, 1, 2 or 3 groups independently selected from halo, —NH$_2$, hydroxyl, cyano, —CF$_3$, $C_{1-6}$alkylamino, oxo, $C_{1-6}$alkoxy, $C_{2-6}$alkenyl, $C_{2-6}$alkynyl, di$C_{1-6}$alkylamino, $C_{1-6}$alkyl, substituted $C_{1-6}$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted $C_{1-6}$alkyl, substituted aryl, substituted heteroaryl, and substituted saturated or partially saturated heterocyclyl is substituted by 0, 1, 2 or 3 groups independently selected from halo, —NH$_2$, hydroxyl, cyano, $C_{1-6}$alkylamino, $C_{1-6}$haloalkyl, oxo, $C_{1-6}$alkoxy, $C_{1-6}$alkoxy$C_{1-6}$alkyl, $C_{1-6}$alkyl, $C_{2-6}$alkenyl, $C_{2-6}$alkynyl, or di$C_{1-6}$alkylamino.

In another embodiment, in conjunction with any of the above or below embodiments, basic moieties on $R^1$ are independently selected from amino, mono-$C_{1-4}$-alkylamino-$C_{1-4}$-alkyl, di-$C_{1-4}$-alkylamino-$C_{1-4}$-alkyl, mono-$C_{1-4}$-alkylamino-$C_{2-4}$-alkenyl, di-$C_{1-4}$-alkylamino-$C_{2-4}$-alkenyl, 5-8 membered nitrogen-containing heterocyclyl-$C_{2-4}$-alkenyl, optionally substituted 5-6 membered nitrogen-containing heterocyclyl and 5-8 membered nitrogen-containing heterocyclyl-$C_{1-4}$-alkyl.

In another embodiment, in conjunction with any of the above or below embodiments, the basic moieties on $R^1$ are independently selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methyl-aminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)amino-methyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)-piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethyl-pyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azabicyclo[3.2.1]oct-6-yl)methyl, 2-piperidinyl and 4-methylpiperazin-1-ylmethyl.

In another embodiment, in conjunction with any of the above or below embodiments, the basic moieties on $R^1$ are independently selected from amino, aminomethyl, isopropylaminomethyl, t-butylaminomethyl, 2-t-butylaminoethyl, 2-tert-butylamino-1-methyl-ethyl, 1-tert-butylaminoethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methyl-aminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)-aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethyl-aminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)-piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethyl-pyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl.

In another embodiment, in conjunction with any one of the above and below embodiments,

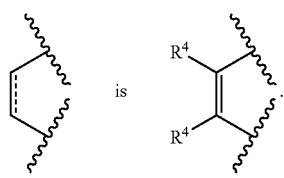 is 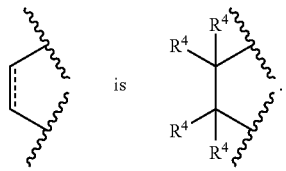.

In another embodiment, in conjunction with any one of the above and below embodiments,

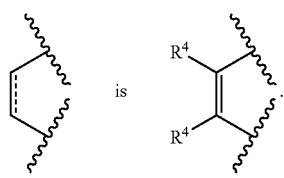 is 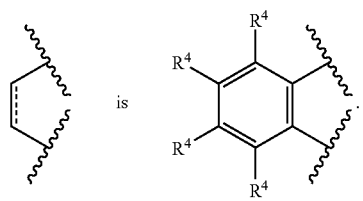.

In another embodiment, in conjunction with any one of the above and below embodiments, A is:

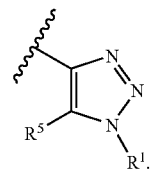

In another embodiment, in conjunction with any one of the above and below embodiments, A is:

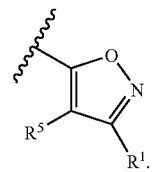

In another embodiment, in conjunction with any one of the above and below embodiments, t is 1.

In another embodiment, in conjunction with any one of the above and below embodiments, $R^1$ is a partially saturated 8-, 9-, 10- or 11-membered bicyclic containing 0, 1, 2, 3 or 4 atoms selected from N, O and S, wherein the carbon and sulfur atoms of the ring are substituted by 0, 1 or 2 oxo groups and the ring is substituted by 1, 2 or 3 basic moieties, and additionally substituted by 0, 1, 2 or 3 substituents selected from $R^g$, $C_{1-8}$alkyl, $C_{1-4}$haloalkyl, cyano, nitro, —C(=O)$R^b$, —C(=O)O$R^b$, —C(=O)N$R^aR^a$, —C(=N$R^a$)N$R^1R^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and the ring is additionally substituted by 0, 1, 2, 3, 4 or 5 substituents independently selected from Br, Cl, F and I, wherein $R^1$ is attached via a sp$^3$ hybridized carbon atom in the bicyclic ring.

In another embodiment, in conjunction with any one of the above and below embodiments, $R^1$ is:

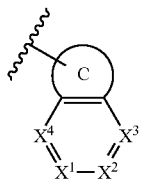

wherein:
$X^1$ is N or CR$^6$;
$X^2$ is N or CR$^7$;
$X^3$ is N or CR$^8$;
$X^4$ is N or CH; wherein no more than two of $X^1$, $X^2$, $X^3$ and $X^4$ is N; and the C ring is a saturated or partially saturated 6- or 7-membered ring containing 0, 1 or 2 atoms selected from N, O and S, wherein the carbon and sulfur atoms of the ring are substituted by 0, 1 or 2 oxo groups and the ring is substituted by 0 or 1 substituents selected from R$^g$, C$_{1-8}$alkyl, C$_{1-4}$haloalkyl, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$—SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and the ring is additionally substituted by 0, 1, 2 or 3 substituents independently selected from Br, Cl, F and I.

In another embodiment, in conjunction with any one of the above and below embodiments, $R^1$ is:

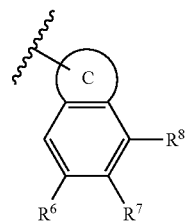

wherein
the C ring is a saturated or partially saturated 6- or 7-membered ring containing 0, 1 or 2 atoms selected from N, O and S, wherein the carbon and sulfur atoms of the ring are substituted by 0, 1 or 2 oxo groups and the ring is substituted by 0 or 1 substituents selected from R$^9$, C$_{1-8}$alkyl, C$_{1-4}$haloalkyl, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and the ring is additionally substituted by 0, 1, 2 or 3 substituents independently selected from Br, Cl, F and I.

In another embodiment, in conjunction with any one of the above and below embodiments, $R^1$ is:

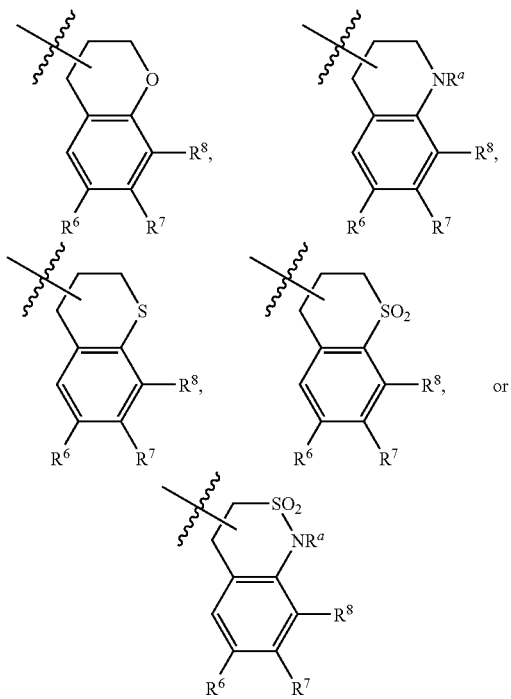

each of which are substituted by 0 or 1 substituents selected from R$^g$, C$_{1-8}$alkyl, C$_{1-4}$haloalkyl, cyano, nitro, —C(=O)R$^b$, —C(=O)OR$^b$, C(=O)NR$^a$R$^a$, —C(=NR$^a$)NR$^a$R$^a$, OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$ NR$^a$R$^a$, —NR$^a$ C$_{2-6}$alkylNR$^a$R$^a$ and —NR$^a$C$_{2-6}$alkylOR$^a$, and additionally substituted by 0, 1, 2 or 3 substituents independently selected from Br, Cl, F and I.

In another embodiment, in conjunction with any one of the above and below embodiments, $R^1$ is:

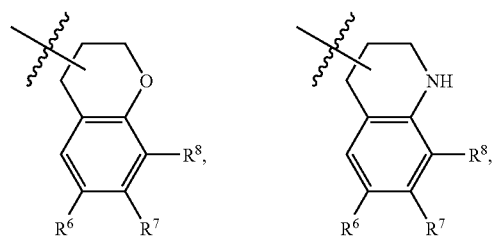

-continued

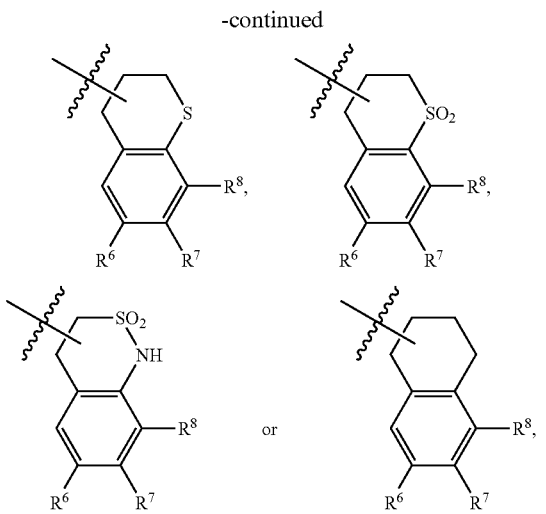

where the part of the above rings that is attached to the nitrogen atom in Formula (I) [i.e., dihydropyranyl, tetrahydropyridinyl, dihydrothiopyranyl, 1,1-dioxodihydrothiopyranyl portion of the ring including the nitrogen ring atom] is substituted by 0 or 1 substituents selected from $R^g$, $C_{1-8}$alkyl, $C_{1-4}$haloalkyl, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, N($R^a$)C(=O)O$R^b$, —N($R^a$)C(=O)N$R^aR^a$, N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and additionally substituted by 0, 1, 2 or 3 substituents independently selected from Br, Cl, F and I and $R^6$, $R^7$ and $R^8$ are independently selected from H, a basic moiety, $R^g$, $C_{1-8}$alkyl, $C_{1-4}$haloalkyl, cyano, nitro, —C(=O)$R^a$, —C(=O)O$R^a$—C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —NR$C^{2-6}$alkylO$R^a$, Br, Cl, F and I; provided that 1 or 2 of $R^6$, $R^7$ and $R^8$ are a basic moiety.

In another embodiment, in conjunction with any one of the above and below embodiments, $R^1$ is:

each of which are substituted by 0 or 1 substituents selected from $R^g$, $C_{1-8}$alkyl, $C_{1-4}$haloalkyl, cyano, nitro, —C(=O)$R^b$, —C(=O)O$R^b$, —C(=O)N$R^aR^a$, —C(=N$R^a$)N$R^aR^a$, —O$R^b$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and additionally substituted by 0, 1, 2 or 3 substituents independently selected from Br, Cl, F and I.

In another embodiment, in conjunction with any one of the above and below embodiments, $R^1$ is:

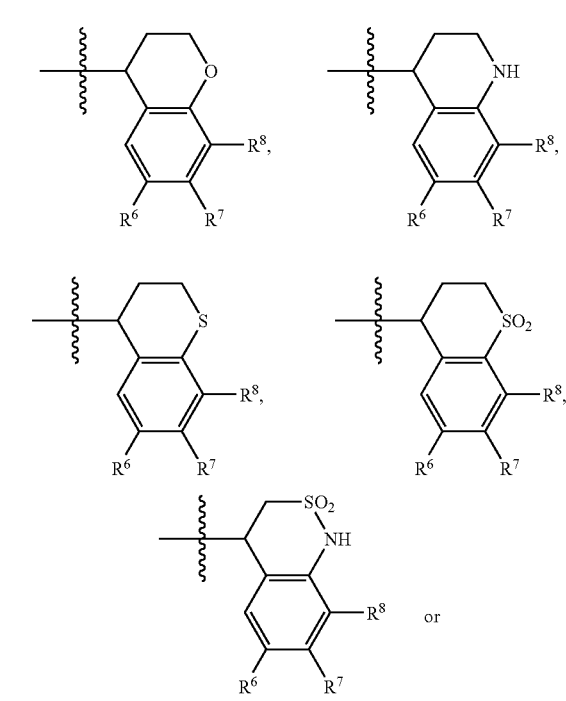

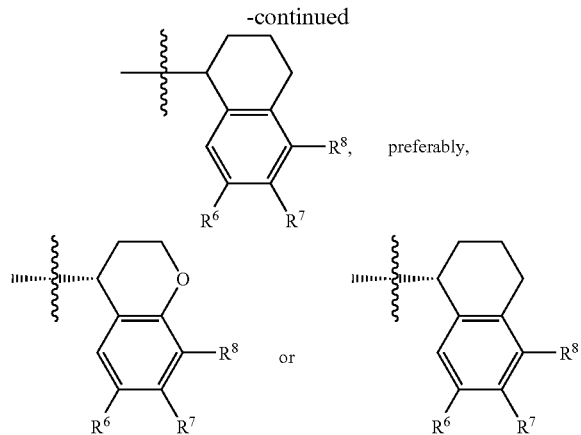

where the part of the above rings that is attached to the nitrogen atom in Formula (I) [i.e., dihydropyranyl, tetrahydropyridinyl, dihydrothiopyranyl, 1,1-dioxodihydrothiopyranyl portion of the ring including the nitrogen ring atom] is substituted by 0 or 1 substituents selected from $R^g$, $C_{1-8}$alkyl, $C_{1-4}$haloalkyl, cyano, nitro, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —OC(═O)N($R^a$)S(═O)$_2R^b$, —O$C_{2-6}$alkylN$R^aR^a$, —O$C_{2-6}$alkylO$R^a$, —S$R^a$, —S(═O)$R^b$, —S(═O)$_2R^b$, —S(═O)$_2$N$R^aR^a$, —S(═O)$_2$N($R^a$)C(═O)$R^b$, —S(═O)$_2$N($R^a$)C(═O)O$R^b$, —S(═O)$_2$N($R^a$)C(═O)N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^B$, —N$R^aC_{2-6}$alkylN$R^aR^a$ and —N$R^aC_{2-6}$alkylO$R^a$, and additionally substituted by 0, 1, 2 or 3 substituents independently selected from Br, Cl, F and I and $R^6$, $R^7$ and $R^8$ are independently selected from H, a basic moiety, $R^g$, $C_{1-8}$alkyl, $C_{1-4}$haloalkyl, cyano, nitro, —C(═O)$R^b$, —C(═O)O$R^b$, —C(═O)N$R^aR^a$, —C(═N$R^a$)N$R^aR^a$, O$R^a$, —OC(═O)$R^b$, —OC(═O)N$R^aR^a$, —OC(═O)N($R^a$)S(═O)$_2R^b$, —O$C_{2-6}$alkylN$R^aR^a$, —O$C_{2-6}$alkylO$R^a$, —S$R^a$, —S(═O)$R^b$, —S(═O)$_2R^b$, —S(═O)$_2$N$R^aR^a$, —S(═O)$_2$N($R^a$)C(═O)$R^b$, —S(═O)$_2$N($R^a$)C(═O)O$R^b$, —S(═O)$_2$N($R^a$)C(═O)N$R^aR^a$, —N$R^aR^a$, —N($R^a$)C(═O)$R^b$, N($R^a$)C(═O)O$R^b$, N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^aC_{2-6}$alkylN$R^aR^a$, —N$R^aC_{2-6}$alkylO$R^a$, Br, Cl, F and I; provided that 1 or 2 of $R^6$, $R^7$ and $R^8$ are a basic moiety.

In another embodiment, in conjunction with any one of the above and below embodiments, $R^2$ is phenyl or napthyl, both of which are substituted by 0, 1, 2 or 3 substituents selected from $R^e$, $R^g$, $C_{1-4}$haloalkyl, halo, cyano, nitro, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —OC(═O)N($R^a$)S(═O)$_2R^b$, —O$C_{2-6}$alkylN$R^aR^a$, —O$C_{2-6}$alkylO$R^a$—S$R^a$, —S(═O)$R^b$, —S(═O)$_2R^b$, —S(═O)$_2$N$R^aR^a$, —S(═O)$_2$N($R^a$)C(═O)$R^b$, —S(═O)$_2$N($R^a$)C(═O)O$R^b$, —S(═O)$_2$N($R^a$)C(═O)N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^aC_{2-6}$alkylN$R^aR^a$ and —N$R^aC_{2-6}$alkylO$R^a$, and additionally substituted by 0, 1, 2, 3, 4 or 5 substituents independently selected from Br, Cl, F and I.

In another embodiment, in conjunction with any one of the above and below embodiments, $R^2$ is phenyl or napthyl, both of which are substituted by 1, 2 or 3 substituents selected from $R^e$, $R^g$, $C_{1-4}$haloalkyl, halo, cyano, nitro, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —OC(═O)N($R^a$)S(═O)$_2R^b$, —O$C_{2-6}$alkylN$R^aR^a$, —O$C_{2-6}$alkylO$R^a$— S$R^a$, —S(═O)R, —S(═O)$_2R^b$, —S(═O)$_2$N$R^aR^a$, —S(═O)$_2$N($R^a$)C(═O)$R^b$, —S(═O)$_2$N($R^a$)C(═O)O$R^b$, —S(═O)$_2$N($R^a$)C(═O)N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^aC_{2-6}$alkylN$R^aR^a$ and —N$R^aC_{2-6}$alkylO$R^a$, and additionally substituted by 0, 1, 2, 3, 4 or 5 substituents independently selected from Br, Cl, F and I.

In another embodiment, in conjunction with any one of the above and below embodiments, $R^2$ is a saturated, partially saturated or unsaturated 5-, 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo groups and the ring is substituted by 0, 1, 2 or 3 substituents selected from $R^e$, $R^g$, $C_{1-4}$haloalkyl, halo, cyano, nitro, —C(═O)$R^b$, —C(═O)O$R^b$, —C(═O)N$R^aR^a$, —C(═N$R^a$)N$R^aR^a$, —O$R^a$, —OC(═O)$R^b$, —OC(═O)N$R^aR^a$, —OC(═O)N($R^a$)S(═O)$_2R^b$, —O$C_{2-6}$alkylN$R^a$, —O$C_{2-6}$alkylO$R^a$, —S$R^a$, —S(═O)$R^b$, —S(═O)$_2R^b$, —S(═O)$_2$N$R^1R^a$, —S(═O)$_2$N($R^a$)C(═O)$R^b$, —S(═O)$_2$N($R^a$)C(═O)O$R^b$, —S(═O)$_2$N($R^a$)C(═O)N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^aC_{2-6}$alkylN$R^aR^a$ and —N$R^aC_{2-6}$alkylO$R^a$, and the ring is additionally substituted by 0, 1, 2, 3, 4 or 5 substituents independently selected from Br, Cl, F and I.

In another embodiment, in conjunction with any one of the above and below embodiments, $R^2$ is an unsaturated 5-, 6- or 7-membered monocyclic ring containing 1, 2 or 3 atoms selected from N, O and S, wherein the carbon atoms of the ring are substituted by 0, 1 or 2 oxo groups and the ring is substituted by 0, 1, 2 or 3 substituents selected from $R^e$, $R^g$, $C_{1-4}$haloalkyl, halo, cyano, nitro, —C(═O)$R^b$, —C(═O)O$R^a$—C(═O)N$R^aR^a$, —C(═N$R^a$)N$R^aR^a$, —O$R^a$, —OC(═O)$R^b$, —OC(═O)N$R^aR^a$, —OC(═O)N($R^a$)S(═O)$_2R^b$, —O$C_{2-6}$alkylN$R^aR^a$, —O$C_{2-6}$alkylO$R^a$, —S$R^a$, —S(═O)$R^b$, —S(═O)$_2R^b$, —S(═O)$_2$N$R^aR^a$, —S(═O)$_2$N($R^a$)C(═O)$R^b$, —S(═O)$_2$N($R^a$)C(═O)O$R^b$, —S(═O)$_2$N($R^a$)C(═O)N$R^aR^a$, —N$R^aR^a$, —N($R^a$)C(═O)$R^b$, —N($R^a$)C(═O)O$R^b$, —N($R^a$)C(═O)N$R^aR^a$, —N($R^a$)C(═N$R^a$)N$R^aR^a$, —N($R^a$)S(═O)$_2R^b$, —N($R^a$)S(═O)$_2$N$R^aR^a$, —N$R^aC_{2-6}$alkylN$R^aR^a$ and —N$R^aC_{2-6}$alkylO$R^a$, and the ring is additionally substituted by 0, 1, 2, 3, 4 or 5 substituents independently selected from Br, Cl, F and I.

In another embodiment, in conjunction with any one of the above and below embodiments, $R^2$ is selected from 2-naphthyl, 1-naphthyl, phenyl, 3-chlorophenyl, 4-chlorophenyl, 3,5-dichlorophenyl, 3,4-dichlorophenyl, 2,4,6-trichlorophenyl, 3-fluorophenyl, 3-methoxyphenyl, 4-methoxyphenyl, 3-biphenyl, 3-chloro-4-methylphenyl, 4-chloro-3methylphenyl, 3-trifluoromethylphenyl, 4-trifluoromethylphenyl, 4-trifluoromethoxyphenyl, 3-methylphenyl, 2,1,3-benzoxadiazol-4-yl, thien-2-yl, 3-pyridyl, 8-quinolyl and 5-isoquinolyl.

In another embodiment, in conjunction with any one of the above and below embodiments, $R^3$ is selected from H, $C_{1-3}$alkyl, $C_{1-3}$haloalkyl, F, Cl, Br and I.

In another embodiment, in conjunction with any one of the above and below embodiments, $R^{3a}$ is selected from H, $C_{1-3}$alkyl, $C_{1-3}$haloalkyl, F, Cl, Br and I.

In another embodiment, in conjunction with any one of the above and below embodiments, $R^3$ and $R^{3a}$ together form oxo.

In another embodiment, in conjunction with any one of the above and below embodiments, $R^4$ is selected from H, $C_{1-3}$alkyl, $C_{1-3}$haloalkyl, F, Cl, Br and I.

In another embodiment, in conjunction with any one of the above and below embodiments, $R^5$ is selected from H, $C_{1-3}$alkyl, $C_{1-3}$haloalkyl, F, Cl, Br and I.

In another embodiment, in conjunction with any one of the above and below embodiments, $R^3$ is H.

In another embodiment, in conjunction with any one of the above and below embodiments, $R^{3a}$ is H.

In another embodiment, in conjunction with any one of the above and below embodiments, $R^4$ is H.

In another embodiment, in conjunction with any one of the above and below embodiments, $R^5$ is H.

In another embodiment, in conjunction with any one of the above and below embodiments, $R^x$ is H.

In another embodiment, in conjunction with any one of the above and below embodiments, $R^x$ is selected from F, Cl, $C_{1-3}$haloalkyl, and $C_{1-3}$alkyl.

In another embodiment, in conjunction with any one of the above and below embodiments, X is —NH—.

In another embodiment, in conjunction with any one of the above and below embodiments, X is —S—.

In another embodiment, in conjunction with any one of the above and below embodiments, X is —O—.

In another embodiment, in conjunction with any one of the above and below embodiments, X is —$NR^d$—.

In another embodiment, in conjunction with any one of the above and below embodiments, X is —$NR^e$—.

In another embodiment, in conjunction with any one of the above and below embodiments, X is —$NR^g$—.

In a second aspect, this invention is directed to a pharmaceutical composition comprising a compound of Formula (I) or any pharmaceutically-acceptable salt or hydrate thereof and a pharmaceutically acceptable excipient.

In a third aspect, this invention is directed to a method of treating a disease in a patient mediated by the B1 receptor comprising administering to the patient a pharmaceutical composition comprising a therapeutically effective amount of a compound of Formula (I) or any pharmaceutically-acceptable salt or hydrate thereof and a pharmaceutically acceptable excipient. Specifically, the compounds of the present invention are useful in the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

The invention also provides for the use of the compounds of the present invention for the prevention or for the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

In a fourth aspect, this invention is directed to the use of one or more of the compounds of the present invention in the manufacture of a medicament. Preferably, the medicament is useful in the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

The compounds of this invention may also act as inhibitors of other receptors or kinases, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

Definitions:

Unless otherwise stated, the following terms used in the specification and claims have the meanings given below:

The term "$C_{\alpha\text{-}\beta}$-alkyl" means an alkyl group having a minimum of α and a maximum of β carbon atoms in a branched, cyclical or linear relationship or any combination of the three, wherein α and β represent integers as indicated in this Application. The alkyl groups described in this section may also contain one or two double or triple bonds. When the alkyl group has a double or triple bond it is also referred to herein as alkenyl or alkynyl respectively.

Examples of $C_{1\text{-}6}$-alkyl include, but are not limited to, the following:

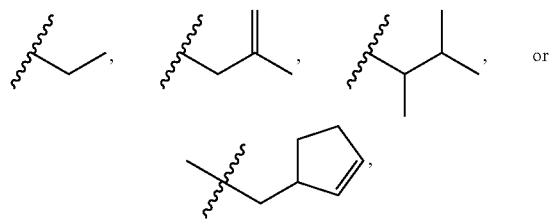

methyl, and the like.

The term "alkylene" means a divalent hydrocarbon radical of one to ten carbon atoms, preferably from two to six carbon atoms unless otherwise stated e.g., methylene, ethylene, propylene, and the like.

The terms "oxo"" represents the group=O (as in carbonyl).

The term "alkoxy" embrace linear or branched oxy-containing radical —OR where R is alkyl of one to ten carbon atoms. More preferred alkoxy radicals are "lower alkoxy" radicals having alkyl of one to six carbon atoms. Examples of such radicals include methoxy, ethoxy, propoxy, butoxy and tert-butoxy. Even more preferred are lower alkoxy radicals with alkyl of one to three carbon atoms. The "alkoxy" radicals may be further substituted at the alkyl radical with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy, and fluoropropoxy.

The term "alkoxyalkyl" embraces linear or branched alkyl radicals having one to ten carbon atoms any of which is substituted with one or more alkoxy radical as defined above. More preferred alkoxyalkyl radicals are "lower alkoxyalkyl" radicals respectively having one to six carbon atoms. Examples of such radicals include methoxymethyl, methoxyethyl, and the like. Even more preferred are lower alkoxyalkyl radicals respectively having one to three carbon atoms alkyl radicals.

The term "aryl", alone or in combination, means a carbocyclic aromatic system of 6 to 12 carbon atoms containing one or two rings wherein such rings may be attached together in a pendent manner or may be fused provided that at least one of the ring is aromatic. The term "aryl" embraces aromatic radicals such as phenyl, naphthyl, tetrahydronaphthyl, indane and biphenyl. More preferred aryl is phenyl. Unless otherwise stated the "aryl" group may have 1 to 3 substituents such as lower alkyl, hydroxyl, halo, haloalkyl, nitro, cyano, alkoxy, and lower alkylamino.

The term "aminoalkyl" embraces linear or branched alkyl radicals having one to ten carbon atoms any one of which is substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces aminoalkyl radical as defined herein having the nitrogen atom independently substituted with an alkyl radical. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "aminoalkenyl" embraces linear or branched alkyl radicals having two to six carbon atoms and at least a double bond wherein any one of the carbon atom is substituted with one or more amino radicals.

The term "$C_{1\text{-}4}$alkylaminoalkenyl" embraces aminoalkenyl radical as defined herein having the nitrogen atom independently substituted with a $C_{1\text{-}4}$alkyl radical.

The term "N-arylaminoalkyl" denotes aminoalkyl radical as defined herein substituted with an aryl radical. More preferred arylaminoalkyl radicals are "lower N-arylaminoalkyl" radicals having alkyl radicals of one to six carbon atoms. Even more preferred are phenylaminoalkyl radicals having one to three carbon atoms. Examples of such radicals include N-phenylaminomethyl and N-phenylaminoethyl.

The term "aralkylaminoalkyl" embraces aralkyl radicals as described below, attached to an aminoalkyl radical as defined herein. More preferred are lower arylalkylaminoalkyl radicals independently having alkyl radicals of one to three carbon atoms.

The term "aralkyl" embraces aryl-substituted alkyl radicals. Preferable aralkyl radicals are "lower aralkyl" radicals having aryl radicals attached to alkyl radicals having one to six carbon atoms. Even more preferred are lower aralkyl radicals phenyl attached to alkyl portions having one to three carbon atoms. Examples of such radicals include benzyl, diphenylmethyl and phenylethyl. The aryl in said aralkyl may be additionally substituted with halo, alkyl, alkoxy, haloalkyl and haloalkoxy.

The term "alkylamino" denotes amino groups, which have been substituted with one alkyl radical and with two alkyl radicals, including terms "N-alkylamino" and "N,N-dialkylamino". More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable "alkylamino" may be mono or dialkylamino such as N-methylamino, N-ethylamino, N,N-dimethylamino, N,N-diethylamino and the like.

The term "alkylaminoalkoxyalkoxy" embraces alkoxy radicals substituted with an alkylaminoalkoxy radical as defined below. More preferred alkylaminoalkoxyalkoxy radicals are "lower alkylaminoalkoxyalkoxy" radicals independently having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminoethoxymethoxy, N,N-dimethylaminoethoxymethoxy, N,N-diethylaminomethoxymethoxy, and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "aminoalkoxy" embraces alkoxy radicals substituted with an amino radical. More preferred aminoalkoxy radicals are "lower aminoalkoxy" radicals having alkoxy radicals of one to six carbon atoms. Suitable aminoalkoxy radicals may be aminoethoxy, aminomethoxy, aminopropoxy and the like.

The term "basic moiety" or "basic moieties" means a chemical moiety that has a measured or calculated pKa of from about 7 to about 13. The term also can include a chemical moiety that is protonable, to some extent, between a pH range of from about 7 to about 10. Examples of basic moieties include, but are not limited to, amino, cycloalkylamino$C_{1-6}$alkyl, cycloalkyl$C_{1-6}$alkylamino$C_{1-6}$alkyl, heterocyclylamino$C_{1-6}$alkyl, heterocyclyl$C_{1-6}$alkyl-amino$C_{1-6}$alkyl, arylamino$C_{1-6}$alkyl, aryl$C_{1-6}$alkylamino$C_{1-6}$alkyl, $C_{1-6}$alkylamino$C_{1-6}$alkoxy, $C_{1-6}$alkylamino$C_{1-6}$alkoxy$C_{1-6}$alkoxy, amino$C_{1-6}$ alkoxy, amino$C_{1-6}$alkyl, $C_{1-6}$alkylamino$C_{1-6}$ alkyl, $C_{1-4}$alkylamino-$C_{2-6}$alkenyl, 4-8-membered nitrogen-containing heterocyclyl$C_{2-6}$alkenyl, heterocyclyl$C_{1-6}$amino$C_{2-6}$alkyl, 5-6 membered heterocyclyloxy, 5-6 membered nitrogen-containing heterocyclyl and 5-7 membered nitrogen-containing heterocyclyl-alkyl; more specifically amino, cycloalkylamino$C_{1-6}$alkyl, cycloalkyl$C_{1-6}$alkyl-amino$C_{1-6}$alkyl, heterocyclylamino$C_{1-6}$alkyl, heterocyclyl$C_{1-6}$alkylamino$C_{1-6}$alkyl, arylamino$C_{1-6}$alkyl, aryl$C_{1-6}$alkylamino$C_{1-6}$alkyl, $C_{1-6}$alkylamino$C_{1-6}$alkoxy, $C_{1-6}$alkylamino-$C_{1-6}$ alkoxy$C_{1-6}$alkoxy, amino$C_{1-6}$alkoxy, amino$C_{1-6}$alkyl, $C_{1-6}$alkylamino$C_{1-6}$alkyl, $C_{1-4}$alkylamino-$C_{2-6}$alkenyl, 5-8-membered nitrogen-containing heterocyclyl$C_{2-6}$alkenyl, heterocyclyl$C_{1-6}$amino$C_{2-6}$alkyl, 5-6 membered heterocyclyloxy, 5-6 membered nitrogen-containing heterocyclyl and 5-7 membered nitrogen-containing heterocyclyl$C_{1-6}$alkyl. More specifically, amino, aminomethyl, isopropylaminomethyl, 1-butylaminomethyl, 2-t-butylaminoethyl, 2-tert-butylamino-1-methyl-ethyl, 1-tert-butylaminoethyl, 1-(tert-butylamino-methyl)-vinyl, 1-(piperidin-1-ylmethyl)-vinyl, N-isobutyl-aminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethylaminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxy-piperidin-1-ylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azaicyclo[3.2.1]oct-6-yl)methyl, 2-piperidinyl and 4-methylpiperazin-1-ylmethyl. Each basic moiety can be substituted by 0, 1, 2 or 3 groups independently selected from halo, —$NH_2$, —OH, —CN, —$CF_3$, $C_{1-6}$alkylamino, haloalkyl, oxo, $C_{1-6}$alkoxy, $C_{1-6}$alkoxyalkyl, $C_{2-6}$alkenyl, $C_{2-6}$alkynyl, di$C_{1-6}$alkylamino, =NCN; and $C_{1-6}$alkyl, aryl, heteroaryl, cycloalkyl and heterocyclyl, each of which is substituted by 0, 1, 2 or 3 groups independently selected from halo, —$NH_2$, —OH, —CN, —$CF_3$, $C_{1-6}$alkylamino, haloalkyl, oxo, $C_{1-6}$alkoxy, $C_{1-6}$alkoxyalkyl, $C_{1-6}$alkyl, $C_{2-6}$alkenyl, $C_{2-6}$alkynyl, or di$C_{1-6}$alkylamino.

In one embodiment, the basic moiety is selected from cycloalkylamino$C_{1-6}$alkyl, cycloalkyl$C_{1-6}$alkylamino$C_{1-6}$ alkyl, heterocyclylamino$C_{1-6}$alkyl, heterocyclyl-$C_{1-6}$alkylamino$C_{1-6}$alkyl, arylamino$C_{1-6}$alkyl, aryl$C_{1-6}$alkylamino$C_{1-6}$alkyl, $C_{1-6}$alkyl amino$C_{1-6}$alkoxy, $C_{1-6}$alkylamino$C_{1-6}$ alkoxy$C_{1-6}$alkoxy, amino$C_{1-6}$alkoxy, amino$C_{1-6}$alkyl, $C_{1-6}$alkylamino$C_{1-6}$alkyl, $C_{1-4}$alkylamino-$C_{2-6}$alkenyl, 4-8-membered nitrogen-containing heterocyclyl$C_{2-6}$alkenyl, heterocyclyl$C_{1-6}$amino$C_{2-6}$alkyl, 5-6 membered heterocyclyloxy, 5-6 membered nitrogen-containing heterocyclyl and 5-7 membered nitrogen-containing heterocyclyl-alkyl. In another embodiment, the basic moiety is selected from cycloalkylamino$C_{1-6}$alkyl, cycloalkyl$C_{1-6}$alkylamino$C_{1-6}$ alkyl, heterocyclylamino$C_{1-6}$alkyl, heterocyclyl$C_{1-6}$alkylamino$C_{1-6}$alkyl, arylamino$C_{1-6}$alkyl, aryl$C_{1-6}$alkylamino$C_{1-6}$alkyl, $C_{1-6}$alkyl amino$C_{1-6}$alkoxy, $C_{1-6}$alkylamino$C_{1-6}$ alkoxy$C_{1-6}$alkoxy, amino$C_{1-6}$alkoxy, amino$C_{1-6}$alkyl, $C_{1-6}$alkylamino$C_{1-6}$alkyl, $C_{1-4}$alkylamino-$C_{2-6}$alkenyl, 4-8-membered nitrogen-containing heterocyclyl$C_{2-6}$alkenyl, heterocyclyl$C_{1-6}$amino$C_{2-6}$alkyl, 5-6 membered heterocyclyloxy, 5-6 membered nitrogen-containing heterocyclyl and 5-7 membered nitrogen-containing heterocyclyl-alkyl any of which are substituted by halo, $C_{1-6}$alkyl or cycloalkyl.

The term "cycloalkyl" includes saturated carbocyclic groups. Preferred cycloalkyl groups include $C_3$-$C_6$ rings. More preferred compounds include cyclopentyl, cyclopropyl, and cyclohexyl.

The terms "carboxy" or "carboxyl", whether used alone or with other terms, denotes —$CO_2H$.

The term "cycloalkylaminoalkyl" refers to an aminoalkyl radical substituted with one cycloalkyl radical, or two cycloalkyl radicals i.e., it includes "N-cycloalkylaminoalkyl" and "N,N-dicycloalkylaminoalkyl". More preferred cycloalkylaminoalkyl radicals are "lower cycloalkylaminoalkyl" radicals having alkyl radicals with one to six carbon atoms. Even more preferred are lower cycloalkylaminoalkyl radicals having alkyl radicals with one to three carbon atoms. Examples of such lower alkylaminoalkyl radicals include N-cyclohexylaminomethyl, and N-cyclopentylaminoethyl.

The term "cycloalkyl-alkylaminoalkyl" embraces cycloalkyl radicals as described above, attached to an alkylaminoalkyl radical. More preferred are lower cycloalkylalkylaminoalkyl radicals independently having alkyl radicals of one to three carbon atoms.

"Halo" or "halogen" means a halogen atoms selected from F, Cl, Br and I.

"$C_{\alpha-\beta}$-haloalkyl" means a straight or branched alkyl group where $\alpha$ and $\beta$ are carbon atoms indicated in the claims where—at least one—of the hydrogen atoms attached to the alkyl chain are replaced by F, Cl, Br or I e.g., trifluoromethyl, difluoromethyl, pentafluoroethyl, and the like.

The term "hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

The term "heterocyclyl" embraces saturated, partially saturated and unsaturated heteroatom-containing ring radicals, where the heteroatoms are selected from nitrogen, sulfur and oxygen. It does not include rings containing -O-O- or —S—S— groups in the ring system. Preferred heterocyclic radicals include five to ten membered fused or infused radicals. Unless otherwise stated the "heterocyclyl" group may have 1 to 3 substituents such as hydroxyl, halo, haloalkyl, cyano, lower alkyl, lower aralkyl, oxo, lower alkoxy, amino, and lower alkylamino.

Examples of saturated heterocyclic radicals include saturated 3 to 8-membered heteromonocyclic group containing 1 to 4 nitrogen atoms [e.g. pyrrolidinyl, imidazolidinyl, piperidino, piperazinyl]; saturated 3 to 8-membered heteromonocyclic group containing 1 to 2 oxygen atoms and 1 to 3 nitrogen atoms [e.g. morpholinyl]; saturated 3 to 8-membered heteromonocyclic group containing 1 to 2 sulfur atoms and 1 to 3 nitrogen atoms [e.g., thiazolidinyl]. Examples of partially saturated heterocyclyl radicals include dihydrothiophene, dihydropyran, dihydrofuran and dihydrothiazole.

Examples of unsaturated heterocyclic radicals, also termed "heteroaryl" radicals, include unsaturated 5 to 6 membered heteromonocyclyl groups containing 1 to 4 nitrogen atoms, for example, pyrrolyl, pyrrolinyl, imidazolyl, pyrazolyl, 2-pyridinyl, 3-pyridinyl, 4-pyridinyl, pyrimidinyl, pyrazinyl, pyridazinyl, triazolyl [e.g., 4H-1,2,4-triazolyl, 1H-1,2,3-triazolyl, 2H-1,2,3-triazolyl]; unsaturated 3 to 6-membered heteromonocyclic group containing an oxygen atom, for example, pyranyl, 2-furanyl, 3-furanyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolinyl, isoindolinyl, indolizinyl, benzimidazolyl, quinolinyl, isoquinolinyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl].

The term also includes bridged, spiro and oxo-containing heterocyclic rings, such as 1,4-dioxa-8-aza-spiro[4.5]decyl, phthalimidyl, 1,4-dioxa-8-aza-spiro[4.5]decyl, and (1-azabicyclo[2.2.2]oct-3-yl).

More preferred examples of heteroaryl radicals include quinolinyl, isoquinolinyl, imidazolyl, pyridinyl, thienyl, thiazolyl, oxazolyl, furanyl, and pyrazinyl. Even more preferred heteroaryl radicals are 5- or 6-membered heteroaryl, containing one or two heteroatoms selected from sulfur, nitrogen and oxygen, selected from thienyl, furanyl, pyrrolyl, thiazolyl, oxazolyl, imidazolyl, pyrazolyl, isoxazolyl, isothiazolyl, pyridinyl, piperidinyl and pyrazinyl.

The term "heterocyclyloxy" refers to —OR radical where R is optionally substituted heterocyclyl radical is as defined above e.g., piperidinyloxy, and the like.

The term "heterocyclylaminoalkyl" embraces heterocyclyl radicals as described above, attached to an aminoalkyl radical.

The term "heterocyclylalkyl" embraces heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkyl radicals having alkyl portions of one to three carbon atoms. Examples include such radicals as pyridinylmethyl and thienylmethyl.

The term "heterocyclylalkenyl" embraces heterocyclic-substituted alkenyl radicals wherein the alkenyl group has two to six carbon atoms.

The term "heterocyclyl$C_{1-6}$alkylamino$C_{1-6}$alkyl" embraces aminoalkyl radical wherein the alkyl radical has one to six carbon atoms and further wherein the nitrogen atom of the amino group is independently substituted with heterocyclyl$C_{1-6}$alkyl radical as defined herein.

The term "... a saturated 5-, 6- or 7-membered monocyclic or 6-, 7-, 8-, 9-, 10- or 11-membered bicyclic hydrocarbon ring ... in the definition of $R^1$, $R^2$, $R^g$ groups in Formula (I)" means a hydrocarbon ring that do not contain a double bond.

The term "... a partially saturated 5-, 6- or 7-membered monocyclic or 6-, 7-, 8-, 9-, 10- or 11-membered bicyclic hydrocarbon ring ... in the definition of $R^1$, $R^2$, $R^g$ groups in Formula (I)" means a hydrocarbon ring that contain one or more double bonds provided that they are not aromatic.

The term "... a unsaturated 5-, 6- or 7-membered monocyclic or 6-, 7-, 8-, 9-, 10- or 11-membered bicyclic hydrocarbon ring ... in the definition of $R^1$, $R^2$, $R^g$ groups in Formula (I)" means a hydrocarbon ring where at least one of the rings is aromatic.

The phrase "therapeutically-effective" is intended to qualify the amount of compound of the present invention, which will achieve the goal of improvement in disorder severity and the frequency of incidence over treatment of each agent by itself, while avoiding adverse side effects typically associated with alternative therapies. For example, effective pain therapeutic agents relieve the pain sensation of the patient. Alternatively, effective therapeutic agents for the treatment of inflammation minimize the damage from the inflammation, and the like.

The term "treatment" includes therapeutic treatment as well as prophylactic treatment (either preventing the onset of disorders altogether or delaying the onset of a pre-clinically evident stage of disorders in individuals).

The term "comprising" is meant to be open ended, including the indicated component but not excluding other elements.

The specification and claims contain listing of species using the language "selected from ... and ... " and "is ... or ... " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups from the genus.

Compounds of the present invention can possess, in general, one or more asymmetric carbon atoms and are thus capable of existing in the form of optical isomers as well as in the form of racemic or non-racemic mixtures thereof. Unless otherwise indicated, the compounds of the present invention, as depicted or named, may exist as the racemate, a single enantiomer, or any uneven (i.e. non 50/50) mixture of enantiomers, and are all included in the family of compounds of the invention. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column, such as, for example, a CHIRAL-AGP column, optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. Preferred compounds of the invention are those wherein the carbon attached to the nitrogen atom of the triazole ring has an R configuration if it a chiral carbon:

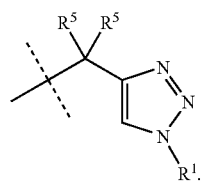

Compounds of the present invention can possess, in general, tautomeric forms, including any enolate anions such as cyclic and acyclic amidine and guanidine groups, heteroatom substituted heterocyclyl groups, and the like, which are illustrated in the following examples. All such forms are within the scope of this invention.

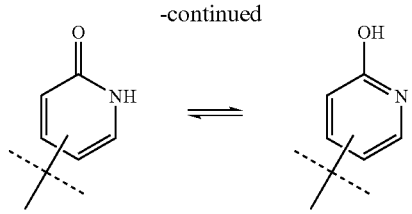

The compounds may also occur in cis- or trans- or E- or Z-double bond isomeric forms. All such isomeric forms of such compounds are included in the present invention. All crystal forms of the compounds described herein are expressly included in the present invention.

The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of the invention may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of the invention include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethylmorpholine, piperazine, piperidine, triethylamine, trimethylamine. All of these salts may be prepared by conventional means from the corresponding compound of the invention by reacting, for example, the appropriate acid or base with the compound of the invention.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as HCl, $H_2SO_4$ and $H_3PO_4$ and such organic acids as oxalic acid, maleic acid, succinic acid and citric acid. Other examples include salts with alkali metals or alkaline earth metals, such as sodium, potassium, calcium or magnesium or with organic bases.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

General Synthetic Procedures

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1994); Rodd's Chemistry of Carbon Compounds, Volumes 1-5 and Supplementals (Elsevier Science Publishers, 1989); Organic Reactions, Volumes 1-40 (John Wiley and Sons, 2003), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (I) where A is a group of formula (a), $R^x$ is hydrogen, $R^3$ and $R^{3a}$ together form oxo, t is 1 and other groups are as defined in the Summary of the Invention can be prepared as shown in Scheme A below.

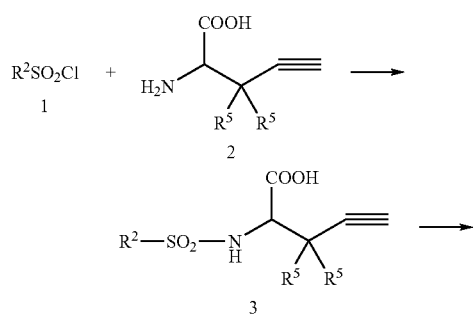

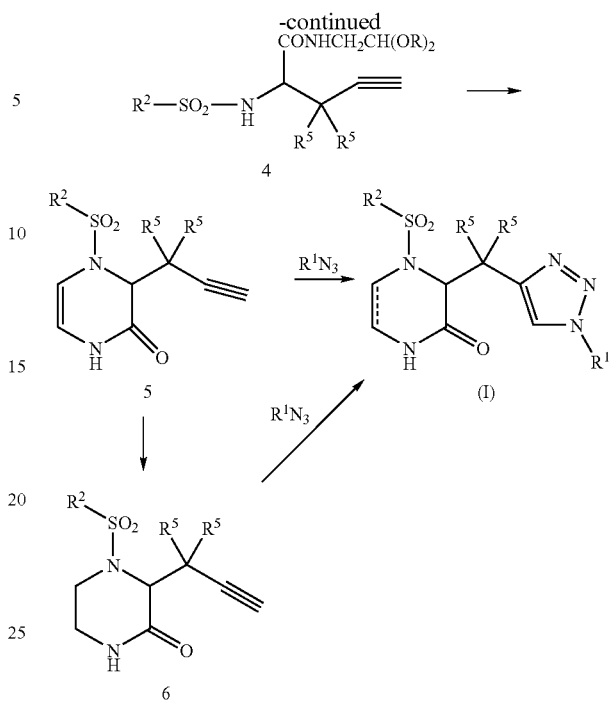

Reaction of a sulfonyl chloride of formula 1 where $R^2$ is as defined in the Summary of the Invention with a propargyl glycine derivative of formula 2 where each $R^5$ is as defined in the Summary of the Invention provides a compound of formula 3. The reaction is carried out in the presence of a base such as sodium carbonate, lithium hydroxide, cesium carbonate, and the like and in a suitable organic solvent such as dioxane, methanol, ethanol, and the like or mixtures of dioxane and water. Compounds of formula I such as benzenesulfonyl chloride, trifluorobenzenesulfonyl chloride, and tolylsulfonyl chloride are commercially available. Compounds of formula 2 are either commercially available or they can be prepared by methods well known in the art. For example, D,L-propargylglycine is commercially available.

Treatment of compound 3 with a dialkoxyalkylamine such as dimethoxyethylamine provides a compound of formula 4. The reaction is carried out in the presence of a coupling agent such as are coupled with the substituted amine 2 using standard peptide coupling conditions coupling agent (e.g., benzotriazol-1-yloxy-trispyrrolidinophosphonium hexafluorophosphate (PyBOP®.), 1-(3-dimethylamino-propyl)-3-ethylcarbodiimide hydrochloride (EDCI), O-(7-azabenzotrizol-1-yl)-1,1,3,3, tetra-methyluronium-hexafluorophosphate (HATU), 0-benzotriazol-1-yl-N,N'N-tetramethyl-uronium hexafluorophosphate (HBTU), 1,3-dicyclohexylcarbodiimide (DCC), or the like) and optionally an appropriate catalyst (e.g., 1-hydroxybenzotriazole (HOBt), 1-hydroxy-7-azabenzotriazole (HOAt), or the like) and non-nucleophilic base (e.g., triethylamine, N-methyl-morpholine, and the like, or any suitable combination thereof) at ambient temperature. Suitable reaction solvents include, but are not limited to, dimethylformamide, methylene chloride, and the like.

Treatment of compound 4 with an acid such as p-TsOH in a suitable organic solvent such as dioxane, and the like provides the corresponding 3,4-dihydropyrazinone derivative of formula 5 which can be reduced to the corresponding pyrazinone derivative 6 with a suitable reducing agent such as triethylsilane in the presence of a suitable acid such as trifluoroacetic acid in a suitable organic solvent such as methylene chloride, and the like.

Treatment of compound 5 or 6 with an azido compound of formula $R^1N_3$ where $R^1$ is as defined in the Summary of the Invention provides a compound of Formula (I). Compounds of formula $R^1N_3$ can be prepared from the corresponding hydroxyl compound of formula $R^1OH$ by treating it diphenylphosphorylazide in the presence of 8-diazabicyclo[5.4.0]undec-7-ene in a suitable organic solvent such as tetrahydrofuran, and the like. It will be readily apparent to a person skilled in the art that compound 5 or 6 can be reacted with an azido compound that is substituted with a precursor group with is then converted to a group within the scope of the invention to provide a compound of Formula (I). For example, a compound of formula 5 or 6 can be reacted with a tetrahydrohydronaphthalene azide wherein the tetrahydronaphthlene ring is substituted with a formyl group to give a precursor compound to (I). The formyl group can then be converted to a basic moiety as discussed in the working examples to provide a compound of Formula (I).

Compounds of Formula (I) where A is a compound of formula (b) can be prepared by reacting compound 5 or 6 with a nitrile oxide of formula $R^1CNO$ where $R^1$ is as defined in the Summary of the Invention under conditions known in the art e.g., see Kozikowski, A. P. *Acc. Chem. Res.* 1984, 17, 410-416.)

Compounds of Formula (I) can be converted to other compounds of Formula (I). For example For example, compounds of formula (I) where $R^3$ and $R^{3a}$ are oxo can be reduced to compounds of formula (I) where $R^3$ and $R^{3a}$ are H.

Alternatively, compounds of Formula (I) where A is a group of formula (a), $R^x$ is hydrogen, $R^3$ and $R^{3a}$ together form oxo, t is 1 and other groups are as defined in the Summary of the Invention can be prepared as shown in Scheme B below.

Scheme B

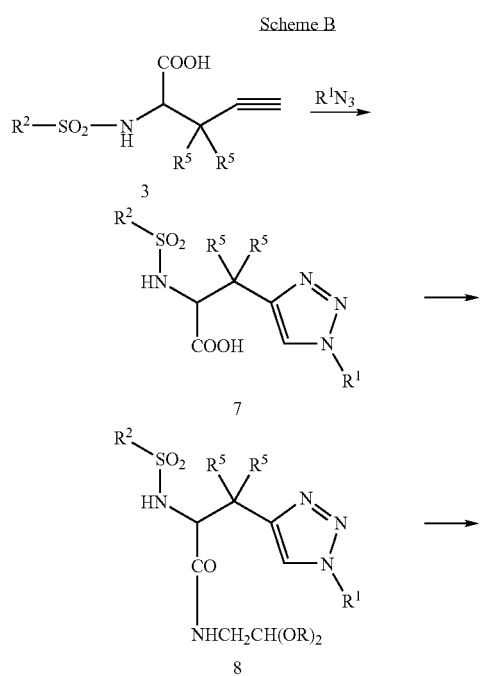

-continued

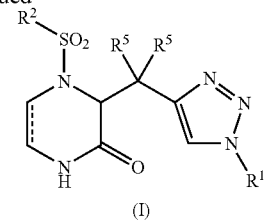

Alternatively, compounds of Formula (I) where A is a group of formula (a), $R^x$ is hydrogen, $R^3$ and $R^{3a}$ together form oxo, t is 1 and other groups are as defined in the Summary of the Invention can be prepared by reacting compound 3 with an azido compound of formula $R^1N_3$ under reaction conditions described above to provide a compound of formula 7 which is then converted to a compound of Formula (I) under the reaction conditions described above.

Compounds of Formula (I) where A is a group of formula (a), $R^x$ is hydrogen, $R^3$ and $R^{3a}$ together form oxo, t is 1 and other groups are as defined in the Summary of the Invention can also be prepared as shown in Scheme C below.

Scheme C

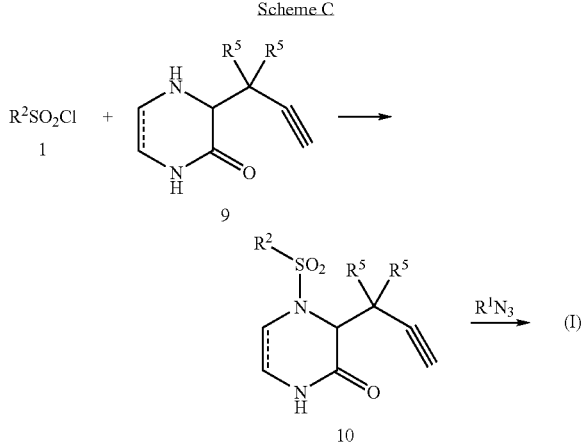

Reaction of a compound of formula 1 with an alkyne of formula 10 provides a compound of formula 10 which is then converted to a compound of Formula (I) as described above. Compounds of formula 10 can be prepared from commercially available starting materials by methods well known in the art. Detailed syntheses of compound of formula 10 are provided in working examples below.

Utility

The compound of Formula (I) are B1 receptor antagonists and hence are useful in the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

Biological Testing

The in vitro binding affinity of the compounds of the invention to the human B1 and B2 bradykinin receptors can be tested using the radioligand binding assay described in Biological Example 1 below. The antagonistic activity of the compounds of the invention for the human B1 and B2 bradykinin receptors can be tested using the calcium flux assay, Rabbit endothelial cell B1-specific $PGI_2$ secretion Assay, and umbilical vein Assay described in Biological Examples 2 and 3 below. The antinociceptive activity of the compounds of the invention was determined using the rat and monkey pain models described in Example 4 below. The antiinflammatory activity of the compounds of the invention was determined using the Green Monkey LPS inflammation model described in Example 5 below.

Pharmaceutical Compositions and Administration

Also embraced within this invention is a class of pharmaceutical compositions comprising the active compounds of the invention in association with one or more non-toxic, pharmaceutically-acceptable carriers and/or diluents and/or adjuvants (collectively referred to herein as "carrier" materials) and, if desired, other active ingredients. The active compounds of the present invention can be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg or 5 to 1000 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.1 and about 50 mg/kg, and more preferably about 0.1 and about 20 mg/kg body weight may be appropriate. The daily dose can be administered in one to four doses per day.

For therapeutic purposes, the active compounds of this invention are ordinarily combined with one or more adjuvants appropriate to the indicated route of administration. If administered; the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily, dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

The present compounds may also be used in combination therapies with opioids and other anti-pain analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists, COX-2 inhibitors such as celecoxib, rofecoxib, valdecoxib, parecoxib, and darecoxib, NSAID's, and sodium channel blockers, among others. More preferred would be combinations with compounds selected from morphine, meperidine, codeine, pentazocine, buprenorphine, butorphanol, dezocine, meptazinol, hydrocodone, oxycodone, methadone, tetrahydrocannibinol, pregabalin, Tramadol [(+) enantiomer], DuP 747, Dynorphine A, Enadoline, RP-60180, HN-11608, E-2078, ICI-204448, acetominophen (paracetamol), propoxyphene, nalbuphine, E-4018, filenadol, mirtentanil, amitriptyline, DuP631, Tramadol [(−) enantiomer], GP-531, acadesine, AKI-1, AKI-2, GP-1 683, GP-3269, 4030W92, tramadol racemate, Dynorphine A, E-2078, AXC3742, SNX-111, ADL2-1294, ICI-204448, CT-3, CP-99,994, and CP-99,994.

Alternatively, the present compounds may also be used in co-therapies with other treatments for inflammation, e.g. steroids, NSAIDs, iNOS inhibitors, p38 inhibitors, TNF inhibitors, 5-lipoxygenase inhibitors, $LTB_4$ receptor antagonists and $LTA_4$ hydrolase inhibitors.

EXAMPLES

In order that the invention described herein may be more readily understood, the following examples illustrate the preparation of compounds of Formula (I) (Examples) and intermediates (References) according to the invention.

It should be understood that these examples are for illustrative purposes only and are not to be construed as limiting this invention in any manner. Unless otherwise noted, all materials were obtained from commercial suppliers and used without further purification. All parts are by weight unless otherwise indicated. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at RT. Synthesis of intermediate compounds is denoted herein as Reference and synthesis of the a compound of Formula (I) is denoted herein as Examples.

The following abbreviations are used:

| | |
|---|---|
| AcOH, HOAc- | acetic acid |
| AIBN- | 2,2'-azobisisobutyronitrile |
| $BH_3 \cdot SMe_2$- | borane-methyl sulfide complex |
| $BH_3$- | borane |
| $Br_2$- | bromine |
| CBS- | Corey-Bakshi-Shibata Catalyst |
| $CCl_4$- | carbon tetrachloride |
| $CH_2Cl_2$- | dichloromethane; DCM |
| $CH_3CN$- | acetonitrile |
| $CHCl_3$- | chloroform |
| DBU- | 1,8-diazabicyclo[5.4.0]undec-7-ene |
| DCE- | 1,2-dichloroethane |
| DMAP- | 4-(dimethylamino)pyridine |
| DMF- | dimethylformamide |
| DMSO- | dimethyl sulfoxide (also known as methyl sulfoxide) |
| DPPA- | diphenylphosphoryl azide |
| EDC, EDCI- | (3-dimethylamino-propyl)-ethyl carbodiimide-HCl salt |
| $Et_2O$- | diethyl ether |
| EtOAc- | ethyl acetate |
| EtOH- | ethanol |
| g- | gram |
| h- | hour |
| $H_2$- | hydrogen |
| $H_2O$- | water |
| $H_2SO_4$- | sulfuric acid |
| $H_3PO_4$- | phosphoric acid |
| HATU- | 0-(7-Azabenzotriazol-1-yl)-N,N,N',N'-tetramethyluronium hexafluorophosphate |
| HCl- | hydrochloric acid |
| $HCO_2H$- | formic acid |
| HOAt- | 1-hydroxy-7-azabenzotriazole |
| HOBt- | 1-hydroxybenzotriazole |
| $Ip_2NEt$, DIEA- | diisopropylethylamine |
| IPA- | isopropanol |
| iPrOH- | isopropanol |
| ISCO- | ISCO liquid chromatography system |
| $K_2CO_3$- | potassium carbonate |
| KCN- | potassium cyanide |
| KOH- | potassium hydroxide |
| LAH- | lithium aluminum hydride |
| LDA- | lithium diisopropylamide |
| LiOH- | lithium hydroxide |
| $Me_2NH$- | dimethylamine |
| MeOH- | methanol |
| $MgSO_4$- | magnesium sulfate |
| min- | minutes |
| mL- | milliliter |
| $N_2$- | nitrogen |
| $NaBH(OAc)_3$- | sodium triacetoxyborohydride |
| $NaBH_4$- | sodium borohydride |
| $NaHCO_3$- | sodium bicarbonate |
| $NaN_3$- | sodium azide |
| NaOAc- | sodium acetate |
| NaOH- | sodium hydroxide |
| NBS- | N-bromosuccinimide |
| $NH_3$- | ammonia |
| $NH_4Cl$- | ammonium chloride |
| $NH_4OH$- | ammonium hydroxide |
| NMM- | N-methylmorpholine |
| NMP- | 1-methyl-2-pyrrolidone |
| $Pd(OH)_2$- | palladium hydroxide |
| Pd/C- | palladium on carbon |
| $PPh_3$- | triphenylphosphine |
| $(PPh_3)_2NiBr_2$- | bis(triphenylphosphine)nickel(II) bromide |
| RT- | room temperature |
| $SiO_2$- | silica |
| $SOCl_2$- | thionyl chloride |
| TEA, $Et_3N$- | triethylamine |
| TFA- | trifluoroacetic acid |
| THF- | tetrahydrofuran |
| TsCl- | p-tosyl chloride |
| TsOH- | p-toluene sulfonic acid |

Synthetic Examples

Reference 1

Synthesis of methyl (R)-5-azido-5,6,7,8-tetrahydro-naphthalene-2-carboxylate and (R)-methyl 4-azido-3,4-dihydro-2H-chromene-7-carboxylate

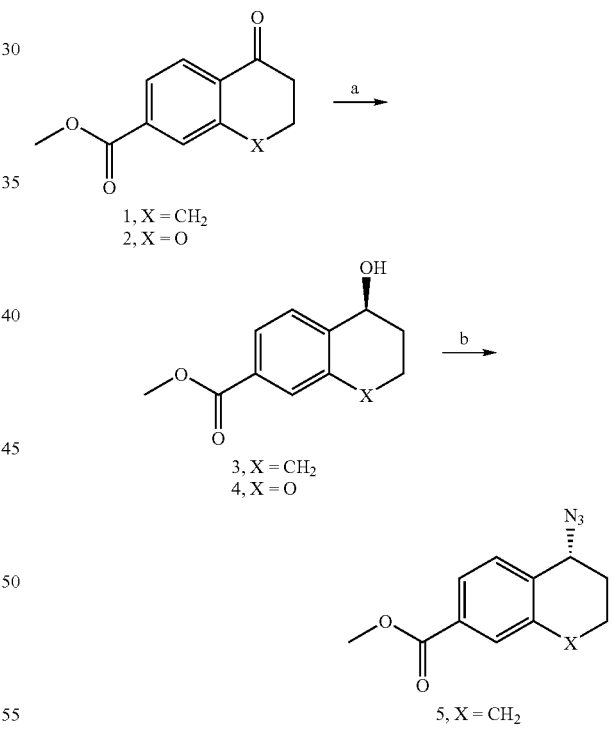

Reagents and Conditions:
a (R)-2-methyl-CBS-oxaborolidine, $BH_3 \cdot DMS$ or (1S,2S)-TsDPEN, [$RuCl_2(\eta^6$-p-cymene)]$_2$, TEA-Formic acid;
b DPPA, DBU.

(i) Synthesis of methyl (S)-5-hydroxy-5,6,7,8-tetrahydronaphthalene-2-carboxylate (3)

To an oven-dried 2 L round-bottomed flask equipped with an argon inlet/outlet and magnetic stirring was added (R)-2- methyl-CBS-oxazaborolidine (7.4 mL of a 1 M solution in toluene, 7.4 mmol, Aldrich). Toluene (190 mL) was added and the reaction mixture was cooled in an ice-salt bath (bath temp.=−10° C.). BH$_3$—SMe$_2$ was added (17 mL, 180 mmol, Aldrich), then 5-oxo-5,6,7,8-tetrahydro-naphthalene-2-carboxylic acid methyl ester (30 g, 150 mmol, Albany Molecular) in 200 mL of THF was added over 5 h using a syringe pump. After the addition was complete, the reaction mixture was stirred for an additional 1 h. The reaction mixture was poured into an addition funnel, and then added to 200 mL of MeOH, cooled in a ice-salt bath, over 30 min at such a rate that the internal temperature was kept below 0° C. The mixture was concentrated in vacuo. Et$_2$O (1 L) was added, and the mixture was washed with 1M H$_3$PO$_4$ (3×), 5% NaHCO$_3$, and brine (ca. 400 mL each wash). The organic layer was dried over MgSO$_4$, filtered and concentrated in vacuo. The residue was dissolved in Et$_2$O again (500 mL), and the mixture was washed with 1M H$_3$PO$_4$ (3×200 mL), satd NaHCO$_3$, and brine. After drying the organic layer over MgSO$_4$, the mixture was filtered and concentrated in vacuo, which gave the title compound as a white-yellow solid. MS (+ion ESI) m/z=207 (MH$^+$), 189 (MH$^+$-H$_2$O).

(ii) Synthesis of (S)-methyl 4-hydroxy-3,4-dihydro-2H-chromene-7-carboxylate (4)

A solution of (1S,2S)-TsDPEN (1.709 g, 4.85 mmol) in isopropanol (5 mL) was added to a 35 mL schlenk-flask and cooled to 0° C. The solution was degassed by three cycles of evacuation/nitrogen refill. Then, [RuCl$_2$(η$^6$-p-cymene)]$_2$ (1.313 g, 2.425 mmol) was added, followed by TEA (1.352 mL, 9.699 mmol). The reaction mixture was heated to 80° C. under N$_2$ for 1 h and cooled. The iso-propanol was removed under a stream of nitrogen, and dissolved in 10 mL acetonitrile. The catalyst solution was added to nitrogen filled 1 L 3-N flask equipped with overhead stirring. 7-Carbomethoxy-4-chromanone (100 g, 485 mmol) and 400 mL acetonitrile was added to the flask, followed by 5:2 formic acid-TEA (50 mL). The reaction mixture was incubated for 24 h at 30° C. An additional portion of formic acid-TEA (5 mL) was added and the reaction mixture stirred for an additional 24 h. The solution was concentrated completely by rotary evaporation. The product was purified by crystallization from 200 mL 2-propanol and 100 mL hexanes. The solids were collected by filtration and washed with cold 2:1 iPrOH-Hex. Final drying of the solids afforded the title compound. MS (m/z): 208.9 (m+H). Chiral HPLC showed the enantiomeric purity to be greater than 98%, when compared to racemic material.

(iii) Synthesis of methyl (R)-5-azido-5,6,7,8-tetrahydro-naphthalene-2-carboxylate (5)

To a 500 mL three-neck round-bottomed flask equipped with argon inlet/outlet, thermometer, and magnetic stirring was added 5(S)-hydroxy-5,6,7,8-tetrahydro-naphthalene-2-carboxylic acid methyl ester (29 g, 140 mmol) in 280 mL of toluene. The reaction mixture was cooled in a ice-salt bath, and DPPA (36 mL, 170 mmol, Aldrich) was added (internal temp.=−4° C.). DBU (25 mL, 170 mmol, Aldrich) was added over 10 min at such a rate that the internal temperature was kept below 1° C. The ice in the bath was allowed to melt, and the reaction continued for 12 h during which time the mixture stopped stirring because a precipitate had formed. Stirring was resumed, and the reaction mixture was stirred at RT for another 11 h. The reaction contents were poured into a 2 L sep funnel, and the lower dark-brown layer was removed. Water (250 mL) was added to the remaining top layer, and the mixture was extracted with Et$_2$O (3×250 mL). The combined organic layers were washed with 1 M H$_3$PO$_4$, water, satd NaHCO$_3$, and brine. The organic layer was dried over MgSO$_4$, filtered and concentrated in vacuo. Purification by silica gel chromatography (330 g Isco Redisep® column, 1:1 hexane-CH$_2$Cl$_2$) of the crude material provided the title compound. MS (+ion ESI) m/z=232 (MH$^+$).

(iv) Synthesis of (R)-methyl 4-azido-3,4-dihydro-2H-chromene-7-carboxylate (6)

To a 3 L three-neck round-bottomed flask equipped with argon inlet/outlet, thermometer, and magnetic stirring was added (S)-methyl 4-hydroxychroman-7-carboxylate (71 g, 340 mmol) in 800 mL of toluene. The reaction vessel was cooled with a ice/salt bath, and treated with a solution of diphenylphosphoryl azide (88 mL, 407 mmol, Aldrich) in 200 mL toluene (internal temp.=−4° C.). After 10 min, a solution of 1,8-diazabicyclo[5.4.0]undec-7-ene (61 mL, 407 mmol, Aldrich) in toluene (350 mL) was added over 30 min (the internal temperature did not exceed 1° C.). The reaction mixture was warmed to room temp and stirred for 40 h. The reaction mixture was diluted with 800 mL EtOAc and washed with 1 M H$_3$PO$_4$, water, 5% NaHCO$_3$, and brine. The organic layer was dried over Na$_2$SO$_4$, filtered and concentrated in vacuo. The residue was purified by silica gel chromatography (10:1 hexane-EtOAc) to provide the title compound. MS (+ion ESI) m/z=234 (MH$^+$).

Reference 2

Synthesis of (R)-1-((4-azidochroman-7-yl)methyl)-4-fluoropiperidine

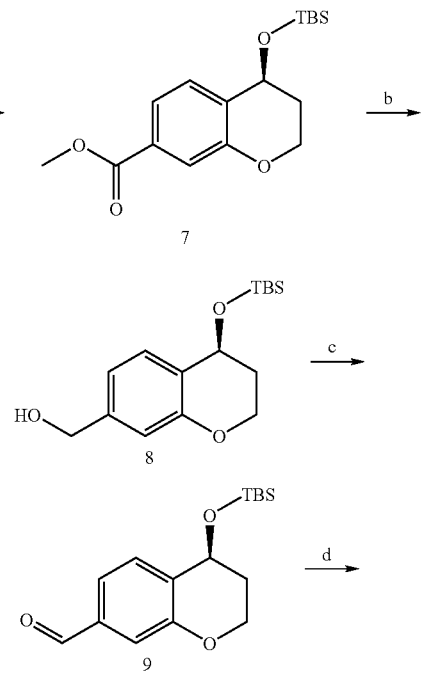

-continued

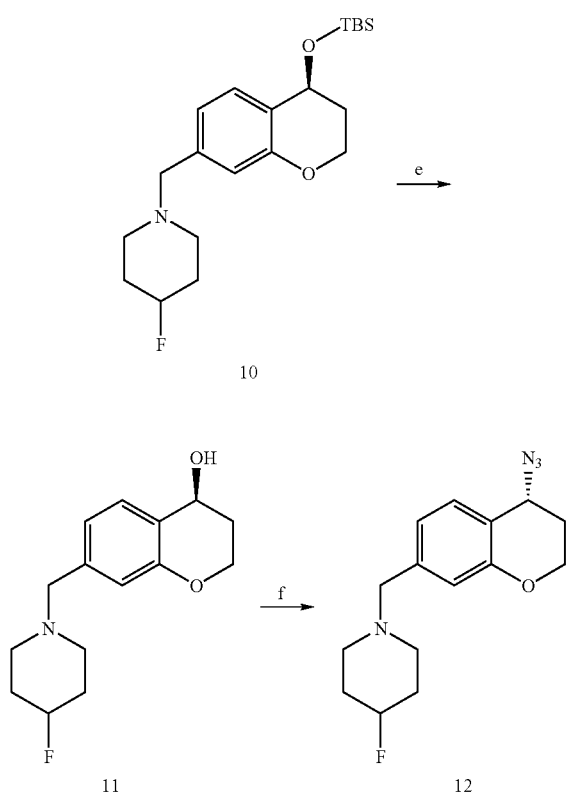

Reagents and Conditions:
a  TBSCl, imidazole;
b  Dibal;
c  MnO₂, CHCl₃;
d  4-fluoropiperidine, NaBH(OAc)₃;
e  TBAF;
f  DPPA, DBU.

Step (i): Synthesis of (S)-methyl 4-(tert-butyldimethylsilyloxy)-3,4-dihydro-2H-chromene-7-carboxylate (7)

A mixture of (S)-methyl-4-hydroxyl-3,4-dihydro-2H-chromene-7-carboxylate (10.2 g, 49.0 mmol), imidazole (3.70 g, 53.9 mmol), and TBSCI (8.12 g, 53.9 mmol) in DMF (100 mL) was stirred for 24 h at RT. The reaction mixture was quenched with H₂O and extracted with ether (3×). The organic extracts were dried over MgSO₄, and concentrated to give a brown oil. $^1$H NMR (400 MHz, CDCl₃): δ 0.74 (s, 15H), 1.81 (m, 1H), 1.91 (m, 1H), 3.87 (s, 3H), 4.02 (m, 1H), 4.11 (m, 1H), 4.67 (t, 5.2 Hz, 1H), 7.09 (s, 1H), 7.11 (d, 7.6 Hz, 1H), 7.23 (d, 7.6 Hz, 1H).

Step (ii): Synthesis of (S)-(4-(tert-butyldimethyloxy)-3,4-dihydro-2H-chromen-7-yl)methanol (8)

To a stirred solution of (S)-methyl 4-(tert-butyldimethylsilyloxy)-3,4-dihydro-2H-chromene-7-carboxylate (32.2 g, 99.9 mmol) in 150 mL toluene was added 1.5M DIBAL-H in toluene dropwise. After 1 h, the reaction mixture was cooled to 0° C. and quenched by the slow addition of 2N HCl. The solution was then extracted with EtOAc (3×), dried over MgSO₄, and concentrated to give a reddish oil. $^1$H NMR (400 MHz, CDCl₃): δ 0.74 (s, 15H), 1.81 (m, 1H), 1.91 (m, 1H), 4.02 (m, 1H), 4.11 (m, 1H), 4.55 (s, 2H), 4.67 (t, 5.2 Hz, 1H), 7.09 (s, 1H), 7.11 (d, 7.6 Hz, 1H), 7.23 (d, 7.6 Hz, 1H).

Step (iii): Synthesis of (S)-4-(tert-butyldimethyloxy)-3,4-dihydro-2H-chromene-7-yl-carbaldehyde (9)

A mixture of (S)-(4-(tert-butyldimethyloxy)-3,4-dihydro-2H-chromen-7-yl)methanol (29.3 g, 99.57 mmol) and MnO₂ in 150 mL CHCl₃ was stirred for 6 h at RT. The solid was removed by filtration. The filtrate was concentrated to afford the title compound as a yellow oil. $^1$H NMR (400 MHz, CDCl₃): δ 0.74 (s, 15H), 1.81 (m, 1H), 1.91 (m, 1H), 4.02 (m, 1H), 4.11 (m, 1H), 4.55 (s, 2H), 4.67 (t, 5.2 Hz, 1H), 7.09 (s, 1H), 7.11 (d, 7.6 Hz, 1H), 7.23 (d, 7.6 Hz, 1H), 9.75 (s, 1H).

Step (iv): Synthesis of (S)-1-((4-(tert-butyldimethylsilyloxy)-3,4-dihydro-2H-chromen-7-yl)methyl)-4-fluoropiperidine (10)

A mixture of (S)-4-(tert-butyldimethyloxy)-3,4-dihydro-2H-chromene-7-yl-carbaldehyde (3.65 g, 12.497 mmol), 4-fluoropiperidine.HBr (5 g, 12 mmol), K₂CO₃ and NaBH(OAc)₃ in MeOH (50 mL) was stirred at RT in 24 h. The methanol was evaporated in vacuo, and the residue taken up in H₂O. The solution was acidified to pH 3 with 1N HCl and washed with EtOAc (discarded). The aqueous layer was neutralized with 1N NaOH, and extracted with CH₂Cl₂ (3×). The combined organic extracts were dried over MgSO₄, and concentrated afford the title compound. MS (m/z): 364.4 (m+H).

Step (v): Synthesis of (S)-7-((4-fluoropiperidin-1-yl)methyl-3,4-dihydro-2H-chromen-4-ol (11)

A mixture of (5)-1-((4-(tert-butyldimethylsilyloxy)-3,4-dihydro-2H-chromen-7-yl)methyl)-4-fluoropiperidine (4.54 g, 12.5 mmol) and TBAF (7.92 g, 37.49 mmol) in THF (50 mL) was stirred for 16 h at RT. The reaction mixture was taken up in H₂O, and extracted with EtOAc (3×). The organic layers were extracted with 10% aqueous HCl. The combined aqueous extracts were neutralized with 2N NaOH, and extracted with CH₂Cl₂ (3×). The combined organic extracts were dried over MgSO₄ and concentrated to give the title compound as a yellow oil. MS (m/z, m+1): 282.4.

Step (vi): Synthesis of (R)-1-((4-azidochroman-7-yl)methyl)-4-fluoropiperidine (12)

A solution of (S)-7-((4-fluoropiperidin-1-yl)methyl-3,4-dihydro-2H-chromen-4-ol (1.9 g, 7.2 mmol) in 20 mL THF was cooled to 0° C. DPPA (2.56 g, 9.31 mmol) was then added dropwise. After 10 minutes, DBU (1.42 g, 9.31 mmol) was added and the reaction mixture was stirred overnight at RT. The THF was removed in vacuo and the residue taken up in H₂O. The aqueous solution was extracted with EtOAc (3×), dried over MgSO₄, and concentrated. The 10 crude was purified by SiO₂ chromatography (30% EtOAc/Hexanes) afford the title compound. MS (m/z, m+1): 291.4.

Starting from compounds 3 and 6 compounds 18-28 (Table 1) were prepared as described below:

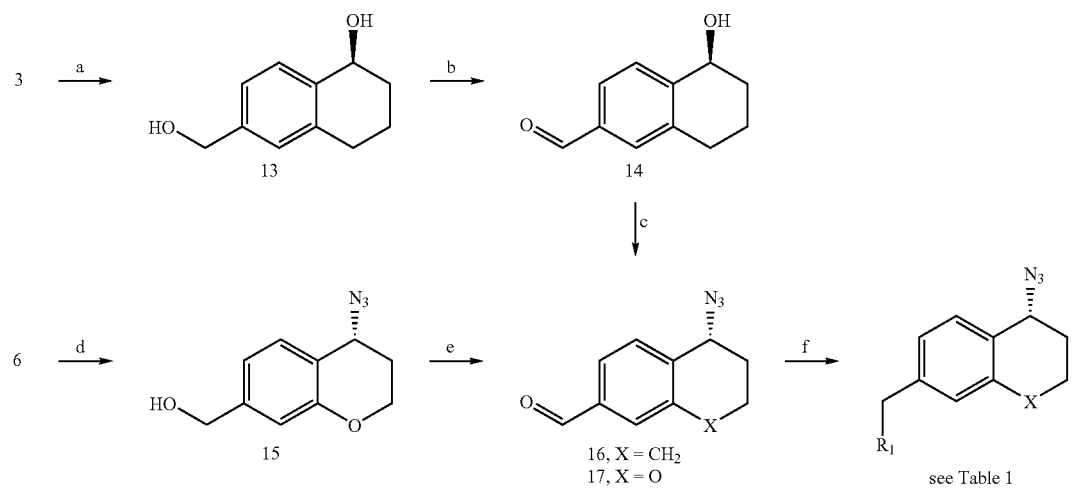

Reagents and Conditions:
a (R)-2-methyl-CBS-oxazaborolidine. BH3•DMS;
b MnO2;
c DPPA, DBU;
d Dibal, THF, 0° C.;
e substituted amine, NaB(OAc)3, HOAc.

TABLE 1

| Compound | X | R |
|---|---|---|
| 18 | O | HN-C(CH3)3 |
| 19 | CH2 | HN-C(CH3)3 |
| 20 | CH2 | piperidinyl (N-linked) |
| 21 | CH2 | HN-CH2-C(CH3)3 |
| 22 | CH2 | NH-cyclopentyl |
| 23 | CH2 | HN-CH2-CH(CH3)2 |
| 24 | CH2 | 4-methylpiperazin-1-yl |
| 25 | CH2 | 4-fluoropiperidin-1-yl |
| 26 | O | piperidin-1-yl |

TABLE 1-continued

| Compound | X | R |
|---|---|---|
| 27 | O | cyclopentyl-NH- |
| 28 | O | 4-fluoropiperidin-1-yl |

Step (i): Synthesis of (S)-6-(hydroxymethyl)-1,2,3,4-tetrahydronaphthalen-1-ol (13)

To an oven-dried 2 L round-bottomed flask equipped with an argon inlet/outlet and magnetic stirring was added (R)-2-methyl-CBS-oxazaborolidine (7.4 mL of a 1 M solution in toluene, 7.4 mmol, Aldrich). Toluene (190 mL) was added and the reaction mixture was cooled in an ice-salt bath (bath temp.=−10° C). $BH_3$—$SMe_2$ was added (17 mL, 180 mmol, Aldrich), then 5-oxo-5,6,7,8-tetrahydro-naphthalene-2-carboxylic acid methyl ester (30 g, 150 mmol, Albany Molecular) in 200 mL of THF was added over 5 h using a syringe pump. After the addition was complete, the reaction mixture was stirred for an additional 1 h. The reaction mixture was allowed to stir for 72 h at RT. The reaction mixture was poured into an addition funnel, and the mixture was added to 200 mL of MeOH, cooled in a ice-salt bath, over 30 min at such a rate that the internal temperature was kept below 0° C. The mixture was concentrated in vacuo to get a solid. $^1$H NMR (400 MHz, DMSO-$d_6$): δ 1.35-1.50 (m, 2H), 1.55-1.75 (m, 2H), 2.30 (s, 1H), 2.35-2.60 (m, 2H), 4.22 (s, 2H), 4.33 (s, 1H), 6.78 (s, 1H), 6.87 (d, 8.0 Hz, 1H), and 7.12 (d, 8.0 Hz, 1H).

Step (ii): Synthesis of (S)-5-hydroxy-5,6,7,8-tetrahydronapthalene-2-carbaldehyde (14)

To a stirred solution of (S)-6-(hydroxymethyl)-1,2,3,4-tetrahydronaphthalen-1-ol (2.5 g, 14 mmol) in $CH_2Cl_2$/MeCN (1:1, 80 mL) was added $MnO_2$ (6.1 g, 70. mmol). The reaction mixture was stirred for 16 h at RT. The solid was filtered off, and the filtrate was concentrated to afford the title compound. MS (m/z): 277.2 (M+H).

Step (iii): Synthesis of (R)-(4-azido-3,4-dihydro-2H-chromen-7-yl)methanol (15)

(R)-Methyl 4-azido-3,4-dihydro-2H-chromene-7-carboxylate (21.50 mmol, 1.0 eq) in 50 mL THF was cooled to 0° C., and treated with DIBAL (63.0 mmol, 3.0 eq). After 2.5 h, the reaction mixture was quenched by adding 50% saturated K-Na tartrate (60 mL). After stirring 1 h at room temperature, the solution was extracted with DCM (4×50 mL). The organic layers were then washed with water (2×50 mL), dried over $MgSO_4$ and concentrated. The residue was purified using $SiO_2$ chromatography (10→80% EtOAc/Hexanes) to afford the title compound.

Step (iv): Synthesis of (R)-5-azido-5,6,7,8-tetrahydronapthalene-2-carbaldehyde (16)

(S)-5-Hydroxy-5,6,7,8-tetrahydronapthalene-2-carbaldehyde (19.73 mmol) was dissolved in 50 mL of toluene and cooled to 0° C. Diphenylphosphoryl azide (29.6 mmol, 1.5 eq) was added, followed by 1,8-diazabicyclo[5.4.0]undec-7-ene (23.07 mmol, 1.2eq). After stirring at room temperature overnight, the solvent was evaporated. The residue was purified by $SiO_2$ chromatography (5-30% ethyl acetate in dichloromethane) to afford the title compound. MS (m/z): 204.2 (M+H).

Step (v): Synthesis of (R)-4-azido-3,4-dihydro-2H-chromene-7-carbaldehyde (17)

To a stirred solution of (R)-(4-azido-3,4-dihydro-2H-chromen-7-yl)methanol (3.293 g, 16.05 mmol) in 50 mL DCM was added manganese dioxide (160.3 mmol, 10.0 eq). The reaction mixture was allowed to stir overnight. A second portion of manganese dioxide (57.84 mmol, 3.5 eq) was added and stirred an additional 4 h. The reaction mixture was filtered and concentrated to yield the aldehyde.

Step (vi): Synthesis of (R)-1-((5-azido-5,6,7,8-tetrahydronaphthalen-2-yl)methyl)piperidine (20)

To a 100 mL flame dry round bottom flask was added (R)-5-azido-5,6,7,8-tetrahydro-naphthalene-2-carbaldehyde (200 mg, 0.99 mmol), piperidine (0.5 mL, 5 mmol), dry DCM (10 mL), HOAc (1 drop), and $CH(OMe)_3$. The resulting mixture was stirred under $N_2$ for 3 h at RT. Then, $NaBH(OAc)_3$ (632 mg, 2.98 mmol) was added and stirred for 20 h. The reaction mixture was quenched with 5% $NaHCO_3$ and concentrated in vacuo. The residue was partitioned between EtOAc and $H_2O$. The organic layer was washed with $H_2O$, brine, dried over $MgSO_4$ and concentrated. The residue was purified by $SiO_2$ (95% DCM:5% MeOH) to afford the title compound. MS (m/z): 271.2 (M+H) (Calc'd for $C_{16}H_{22}N_4$: 270.37).

(R)-1-((4-Azido-3,4-dihydro-2H-chromen-7-yl)methyl)piperidine (18) was synthesized by the procedure described for (20);

Using the same procedure described for (20), and using (R)-4-azido-3,4-dihydro-2H-chromene-7-carbaldehyde afforded (R)-1-((4-Azido-3,4-dihydro-2H-chromen-7-yl)methyl)piperidine (26) MS m/z: 273.6 (M+H) (Calc'd for $C_{15}H_{20}N_4O$–272.35); and Using the same procedure described for (20), and using (R)-4-azido-3,4-dihydro-2H-chromene-7-carbaldehyde afforded (R)-N-((4-Azido-3,4-dihydro-2H-chromen-7-yl)methyl)-cyclopentylamine (27) MS (m/z): 273.3 (M+H) (Calc'd for $C_{15}H_{20}N_4O$–272.35).

Synthesis of (R)-N-((5-azido-5,6,7,8-tetrahydronaphthalen-2-yl)methyl)cyclopentanamine (22)

(R)-5-Azido-5,6,7,8-tetrahydronapthalene-2-carbaldehyde (1 g, 5 mmol) in 10 mL DCM was treated with cyclopentylamine (14.9 mmol, 3 eq), acetic acid (14.9 mmol, 3 eq) and $MgSO_4$. After stirring for 3 d, sodium triacetoxy borohydride (14.9 mmol, 3 eq) was added, and stirred overnight. A 5% solution of $NaHCO_3$ was then added to the thick immulsion, and extracted with DCM (3×). The combined organic layers were washed with 5% $NaHCO_3$ (2×), dried over $MgSO_4$ and concentrated. The residue was purified by $SiO_2$ chromatography (0→20% Methanol, 60→40% DCM, 40% THF) to afford the product. MS (m/z): 271.2 (m+H) (Calc'd. for $C_{16}H_{22}N_4$:270.37).

(R)-N-((5-Azido-5,6,7,8-tetrahydronaphthalen-2-yl)methyl)-2-methylpropan-2-amine (19) MS (m/z): 259.2 (m+H) and (R)-N-((5-Azido-5,6,7,8-tetrahydronaphthalen-2-yl)methyl)-2,2-dimethylpropan-1-amine (21) MS (m/z): 273.3 (m+H);

(R)-1-((4-Azido-3,4-dihydro-2H-chromen-7-yl)methyl)-4-fluoropiperidine (28) MS (m/z): 291.2 (M+H) (Calc'd for $Cl_5H_{19}FN_4O$: 290.31); and (R)-N-((5-Azido-5,6,7,8-tetrahydronaphthalen-2-yl)methyl)-2-methylpropan-1-amine (23) MS (m/z): 259.2 (m+H) were prepared as described above.

(R)-1-((5-Azido-5,6,7,8-tetrahydronaphthalen-2-yl)methyl)-4-methylpiperazine (24) was prepared using the same method described for (22) except the product was purified using $C_{1-8}$ chromatography (10→100% acetonitrile water over 14 min,). Removal of the solvent afforded the product. MS (m/z): 286.2 (m+H);

(R)-1-((5-Azido-5,6,7,8-tetrahydronaphthalen-2-yl)methyl)-4-fluoropiperazine (25) was prepared using the same method described for (22) except the product was purified using $SiO_2$ (40% EtOAc in hexanes) to afford the product. MS (m/z): 289.2 (m+H) (Calc'd for $C_{16}H_{21}FN_4$:288.36).

Reference 3

Synthesis of (R)-methyl 4-(1-azidoethyl)benzoate

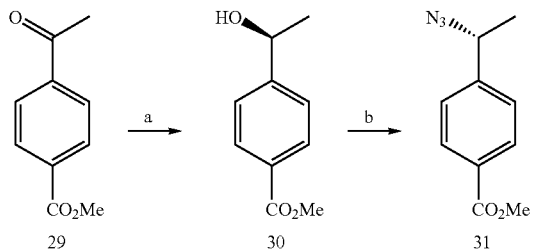

Reagents and Conditions:
a  (R)-2-methyl-CBS-oxazaborolidine, BH$_3$•SMe$_2$;
b  DPPA, DBU.

Step (i): Synthesis of (S)-methyl 4-(1-hydroxyethyl) benzoate (30)

A solution of (R)-2-methyl-CBS-oxazaborolidine (7.5 mL of a 1 M soln in toluene, 7.5 mmol) in toluene (200 mL) was cooled in ice-salt bath (bath temp: −10° C.) under N$_2$. To the solution was added BH$_3$.SMe$_2$ (17.1 mL, 180 mmol) over 3 min. Methyl 4-acetylbenzoate (26.4 g, 148 mmol) in THF (180 mL) was then added over 3 h via syringe pump. The bath temp remained at −10° C. throughout the addition. The reaction mixture was stirred for an additional 30 min, and then MeOH (100 mL) was added over 30 min (bath temp: −10° C.). The ice in the bath was allowed to melt and the reaction mixture was stirred overnight at RT. The reaction mixture was concentrated under reduced pressure, and the residue was diluted with EtOAc (500 mL). The organic solution was washed with 0.1 N HCl aq. (300 mL×4), 5% NaHCO$_3$ (300 mL×2), saturated NaCl (300 mL×2) and dried over Na$_2$SO$_4$. Evaporation of the solvent afforded the title compound. MS (m/z): 181.1 (m+H).

Step (ii): Synthesis of (R)-methyl 4-(1-azidoethyl) benzoate (31)

A solution of (S)-methyl 4-(1-hydroxyethyl)benzoate (24.8 g, 138 mmol) in toluene (300 mL) was cooled in ice-salt bath (bath temp: −10° C.). DPPA (36.3 mL, 168 mmol) was then added dropwise over 15 min (Bath temp was kept at −10° C. during addition). After 5 min, DBU (25.3 mL, 169 mmol) was added over 8 min. The ice in the bath was allowed to melt and the reaction mixture was stirred overnight at RT. The reaction mixture was diluted with EtOAc (200 mL), and washed with 0.1 N HCl aq. (300 mL). The aqueous layer was extracted with EtOAc (100 mL×2) and the combined organic phase was further washed with 0.1N HCl aq. (300 mL×2), 5% NaHCO$_3$ (300 mL×2), and saturated NaCl (300 mL×2). The organic layers was dried over Na$_2$SO$_4$ and concentrated under reduced pressure. The crude product was chromatographed on SiO$_2$ (ISCO: hexane/CH$_2$Cl$_2$=3/1→3/7) to yield the title compound. MS (m/z): 206.2 (m+H).

6-Chloro-4-(R)-azido-3,4-tetrahydro-1-benzothiopyran-1,1 (2H)-dione was synthesized by proceeding as described above.

Reference 4

Synthesis of (R)-2-arylsulfonamidopent-4-ynamides 33-38

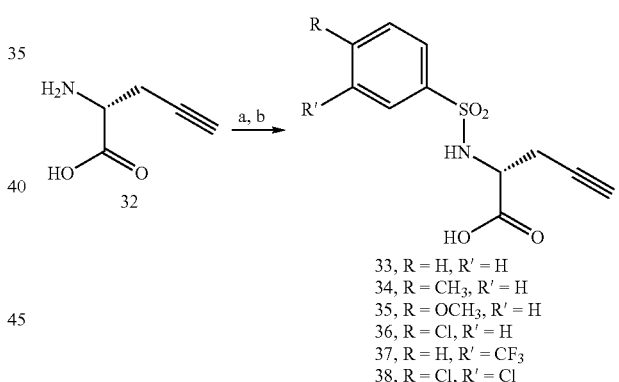

33, R = H, R' = H
34, R = CH$_3$, R' = H
35, R = OCH$_3$, R' = H
36, R = Cl, R' = H
37, R = H, R' = CF$_3$
38, R = Cl, R' = Cl

Reagents and Conditions:
a  D-propargyl alanine, Na$_2$CO$_3$, substituted benzene-sulfonyl chloride;
b  for 37, MeOH, HCl, D-propargyl alanine, Na$_2$CO$_3$, 3-trifluoro-methylbenzene-sulfonyl chloride, LiOH;
c  HOAt, DIPEA, EDCI, NH$_4$Cl.

(i) Synthesis of (R)-(2-benzenesulfonamido)pent-4-ynoic acid (33)

A mixture of d-propargylglycine (32.10 g, 88.46 mmol), Na$_2$CO$_3$ (20.62 g, 194.6 mmol), and benzenesulfonyl chloride (18.74 g, 106.2 mmol) in p-dioxane/H$_2$O (1:1, 200 ml) was stirred overnight at rt. The reaction mixture was concentrated and the ph adjusted to 4.0 with 10% hcl. The aqueous layer was extracted with CHCl$_3$ (3×), dried over mgso$_4$, and concentrated to give the title compound. $^1$H NMR (400 mhz, CDCl$_3$): δ 2.04 (s, 1h), 2.65 (s, 3h), 2.71 (m, 2h), 4.11 (m, 1h), 5.61 (d, 8.4 hz, 1h), 7.61 (m, 3h), 7.88 (m, 2h).

(ii) Synthesis of (R)-2-(4-methylbenzenesulfonamido)pent-4-ynoic acid (34)

Using the same procedure described for 33, d-propargylglycine (5 g, 44 mmol), Na₂CO₃ (9.84 g, 92.9 mmol), and p-TsCl (10.62 g, 48.65 mmol) afforded the title compound. ¹h nmr (400 mhz, cdcl₃): δ 2.04 (s, 1h), 2.65 (s, 3h), 2.71 (m, 2h), 4.11 (m, 1h), 5.61 (d, 8.4 hz, 1h), 7.31 (d, 8.0 hz, 2h), 7.77 (d, 8.0 hz, 2h).

(iii) Synthesis of (R)-4-(4-methoxybenzenesulfonamido)pent-4-ynoic acid (35)

Using the same procedure described for 33, and 4-methoxybenzenesulfonyl chloride afforded the title compound. MS (m/z, m+1): 284.4.

(iv) Synthesis of (R)-4-(4-chlorobenzenesulfonamido)pent-4-ynoic acid (36)

Using the same procedure described for 34, and 4-chlorobenzenesulfonyl chloride afforded the title compound. MS (m/z, m+1): 289.3.

(v) Synthesis of (R)-4-(3-trifluoromethylbenzenesulfonamido)pent-4-ynoic acid (37)

A mixture of D-propargylglycine (13 g, 115 mmol) and 4M HCl in 100 mL p-dioxane and 150 mL MeOH was refluxed for 16 h. The reaction mixture was cooled and concentrated to give a light yellow oil. The crude methyl ester (9.45 g, 57.5 mmol) was dissolved in 150 mL CH₂Cl₂ and treated with pyridine (10.25 g, 126.5 mmol) and cooled to 0° C. To the cooled solution was added 3-trifluoromethylphenylsulfonyl chloride (14.1 g, 57.5 mmol). After stirring for 3 h, H₂O was added and layers were separated. The organic layer was dried over MgSO₄ and concentrated to afford the title compound. ¹H NMR (400 MHz, CDCl₃): δ 2.05 (s, 1H), 2.68 (m, 2H), 3.65 (s, 3H), 4.28 (m, 1H), 6.67 (d, 8.8 Hz, 1H), 7.75 (d, 7.8 Hz, 1H) 7.87 (t, 7.8 Hz, 1H), 8.05 (d, 7.8 Hz, 1H), 8.11 (s, 1H).

(vi) Synthesis of (R)-2-(3,4-dichlorobenzenesulfonamido)pent-4-ynoic acid (38)

(R)-2-Aminopent-4-ynoic acid (16.0 g, 141 mmol) and Na₂CO₃·H₂O (36.8 g, 296 mmol) were dissolved in 500 mL H₂O and 300 mL p-dioxane. To this solution was added 3,4-dichlorobenzene-1-sulfonyl chloride (33.0 g, 134 mmol) dropwise over 25 min. The solution was stirred at RT for 19 h. The solution was then acidified with 5N HCl to pH 1. EtOAc (400 mL) and sat'd NaCl aq. (200 mL) were added and organic layer was separated. The aqueous phase was extracted with EtOAc (200 mL×2), and the combined EtOAc extracts were washed with brine (400 mL×4) and dried over Na₂SO₄. The solvent was removed under reduced pressure and dried in vacuo to yield 38.

Reference 5

Synthesis of (R)-4-arylsulfonamido-3-(prop-2-ynyl) piperazin-2-one derivatives 51-55

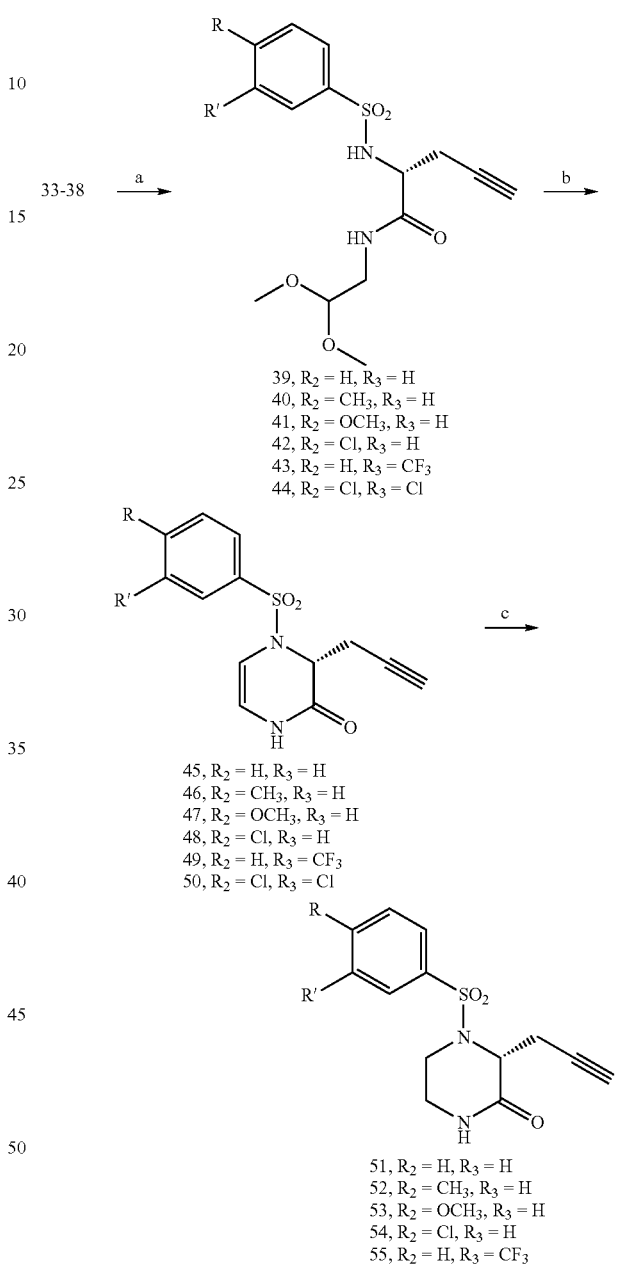

39, R₂ = H, R₃ = H
40, R₂ = CH₃, R₃ = H
41, R₂ = OCH₃, R₃ = H
42, R₂ = Cl, R₃ = H
43, R₂ = H, R₃ = CF₃
44, R₂ = Cl, R₃ = Cl

45, R₂ = H, R₃ = H
46, R₂ = CH₃, R₃ = H
47, R₂ = OCH₃, R₃ = H
48, R₂ = Cl, R₃ = H
49, R₂ = H, R₃ = CF₃
50, R₂ = Cl, R₃ = Cl

51, R₂ = H, R₃ = H
52, R₂ = CH₃, R₃ = H
53, R₂ = OCH₃, R₃ = H
54, R₂ = Cl, R₃ = H
55, R₂ = H, R₃ = CF₃

Reagents and Conditions:
a (2,2-dimethoxyethyl)amine, HOAt, EDCI, DIPEA;
b TsOH, p-dioxane, 60° C.;
c Et₃SiH, TFA, 45° C.

(i) Synthesis of (R)-N-(2.2-dimethoxyethyl)-2-(benzenesulfonamido)pent-4-ynamide (39)

A mixture of (R)-2-(benzenesulfonamido)pent-4-ynoic acid (11.66 g, 46.04 mmol), HOBt (7.46 g, 55.24 mmol), iPr₂NEt (7.13 g, 55.24 mmol), (2,2-dimethoxyethyl)amine (5.81 g, 55.24 mmol), and EDCI (10.53 g, 55.24 mmol) in DMF (100 mL) was stirred for 24 h at RT. The reaction mixture was concentrated and taken up in H$_2$O (100 mL). The aqueous layer was extracted with EtOAc (3×), dried over MgSO$_4$, and concentrated to afford the title compound. $^1$H NMR (400 MHz, CDCl$_3$): δ 2.43 (m, 2H), 2.71 (s, 3H), 2.85 (s, 1H), 2.89 (s, 3H), 2.96 (m, 2H), 3.98 (t, 7.1 Hz, 3H), 4.15 (t, 5.5 Hz, 1H), 7.55 (m, 3H), 7.80 (d, 8.0 Hz, 2H), 7.97 (s, 1H), 8.11 (t, 5.5 Hz, 1H).

(ii) Synthesis of (R)-N-(2,2-dimethoxyethyl)-2-(4-methylbenzenesulfonamido)pent-4-ynamide (40)

A mixture of (R)-2-(4-methylbenzenesulfonamido)pent-4-ynoic acid (11.0 g, 41.2 mmol), HOBt (6.67 g, 49.4 mmol), iPr$_2$NEt (6.40 g, 49.4 mmol), (2,2-dimethoxyethyl)amine (8.70 g, 82.33 mmol), and EDCI (9.5 g, 49 mmol) in DMF (100 mL) was stirred for 24 h at RT. The reaction mixture was concentrated, taken up in H$_2$O, and extracted with EtOAc (3×). The organic extracts were dried over MgSO$_4$ and concentrated to give the title compound. 1H NMR (400 MHz, CDCl$_3$): δ 2.15 (s, 1H), 2.43 (m, 1H), 2.51 (s, 3H), 2.88 (m, 1H), 2.94 (s, 3H), 2.96 (s, 3H), 3.37 (m, 3H), 3.85 (m, 1H), 4.33 (m, 1H), 6.78 (s, 1H), 7.33 (d, 8.0 Hz, 2H), 7.76 (d, 8.0 Hz, 2H), 8.01 (s, 1H).

(iii) Synthesis of (R)-N-(2,2-dimethoxyethyl)-2-(4-methoxylbenzenesulfonamido)pent-4-ynamide (41)

Using the same procedure describe for the synthesis of compound 39, (R)-2-(4-methoxybenznesulfonamido)pent-4-ynoic acid afforded the title compound. $^1$H NMR NMR (400 MHz, CDCl$_3$): δ 2.43 (m, 2H), 2.71 (s, 3H), 2.85 (s, 1H), 2.89 (s, 3H), 2.96 (m, 2H), 3.82 (s, 3H), 3.98 (t, 7.1 Hz, 3H), 4.15 (t, 5.5 Hz, 1H), 7.65 (d, 8.0 Hz, 2H), 7.80 (d, 8.0 Hz, 2H), 7.97 (s, 1H), 8.11 (t, 5.5 Hz, 1H).

(iv) Synthesis of (R)-N-(2,2-dimethoxyethyl)-2-(4-chlorobenzenesulfonamido)pent-4-ynamide (42)

Using the same procedure describe for the synthesis of 39, (R)-2-(4-chlorobenzenesulfonamido)pent-4-ynoic acid afforded the title compound. 1H NMR (400 MHz, CDCl$_3$): δ 2.43 (m, 2H), 2.71 (s, 3H), 2.85 (s, 1H), 2.89 (s, 3H), 2.96 (m, 2H), 3.98 (t, 7.1 Hz, 3H), 4.15 (t, 5.5 Hz, 1H), 7.65 (d, 8.0 Hz, 2H), 7.80 (d, 8.0 Hz, 2H), 7.97 (s, 1H), 8.11 (t, 5.5 Hz, 1H).

(v) Synthesis of (R)-N-(2.2-dimethoxyethyl)-2-(3-trifluoromethylbenzenesulfonamido)-pent-4-ynamide (43)

Using the same procedure describe for the synthesis of 39, (R)-2-(3-trifluoromethylbenzenesulfonamido)pent-4-ynoic acid afforded the title compound. $^1$H NMR (300 MHz, CDCl$_3$): δ 2.05 (s, 1H), 2.65 (m, 2H), 2.85 (s, 3H), 2.96 (s, 3H), 3.35 (m, 2H), 3.96 (t, 6.3 Hz, 1H), 4.32 (t, 5.4 Hz, 1H), 6.86 (t, 5.4 Hz, 1H), 7.68 (t, 7.8 Hz, 1H), 7.82 (d, 7.8 Hz, 1H), 7.97 (s5; 1H), 8.03 (d, 7.8 Hz, 1H), 8.11 (s, 1H).

(vi) Synthesis of (R)-2-(3,4-dichlorobenzenesulfonamido)-N-(2,2-dimethoxyethyl)pent-4-ynamide (44)

To a solution of 1 (35.9 g, 111 mmol), 2,2-dimethoxyethylamine (13.2 mL, 122 mmol) and HOBt (18.2 g, <5% H$_2$O, 128 mmol) in DMF (200 mL) under N$_2$ was added EDCI.HCl (24.8 g, 129 mmol). The reaction mixture was stirred for 20 h at RT. EtOAc (500 mL) was added and washed with 5% NaHCO$_3$ (500 mL×2), and the combined aqueous layer was back-extracted with EtOAc (200 mL×2). The combined EtOAc extracts were washed with 5% NaHCO$_3$ (500 mL×2), 0.1N HCl (500 mL×2), brine (500 mL ×3), and dried over Na$_2$SO$_4$. The solvent was removed under reduced pressure and dried in vacuo to yield the title compound.

(vii) Synthesis of (R)-4-(benzenesulfonyl)-3-(prop-2-ynyl)-3,4-dihydropyrazin-2(1H)-one (45)

A mixture of (R)-N-(2,2-dimethoxyethyl)-2-(benzenesulfonamido)pent-4-ynamide (10.55 g, 30.99 mmol) and p-toluenesulfonic acid (1.47 g, 7.75 mmol) p-dioxane (100 mL) was heated to 60° C. for 36 h. The reaction mixture was cooled, concentrated and taken up in EtOAc. After the organic mixture had stirred, a precipitate had formed that was filtered to afford the product as a tan solid. $^1$H NMR (300 MHz, DMSO-d$_6$): δ 2.98 (s, 1H), 3.35 (d, 7.0 Hz, 2H), 4.35 (t, 7.0 Hz, 1H), 5.98 (m, 2H), 7.71 (m, 5H), 9.65 (s, 1H).

(viii) Synthesis of (R)-4-(4-methylbenzenesulfonyl)-3-(prop-2-ynyl)-3,4-dihydropyrazin-2(1H)-one (46)

A mixture of (R)-N-(2,2-mimethoxyethyl)-2-(4-methylbenzenesulfonamido)pent-4-ynamide (5.0 g, 14 mmol) and p-toluenesulfonic acid (0.67 g, 3.5 mmol) in dioxane (70 mL) was heated to 60° C. for 72 h. The reaction mixture was cooled, concentrated, and taken up in EtOAc. A solid had formed that was filtered and dried to afford the title compound. $^1$H NMR (300 MHz, CDCl$_3$): δ 2.07 (s, 1H), 2.45 (s, 3H), 2.67 (d, 6.7 Hz, 2H), 4.65 (t, 6.7 Hz, 1H), 5.82 (t, 5.1 Hz, 1H), 6.15 (d, 5.1 Hz, 1H), 7.14 (s, 1H), 7.35 (d, 8.3 Hz, 2H), 7.72 (d, 8.3 Hz, 2H).

(ix) Synthesis of (R)-4-(4-methoxylbenzenesulfonyl)-3-(prop-2-ynyl)-3,4-dihydropyrazin-2(1H)-one (47)

Using the procedure described for compound 45, (R)-N-(2,2-dimethoxyethyl)-2-(4-methoxybenzenesulfonamido) pent-4-ynamide afforded the title compound as a tan solid. $^1$H NMR (300 MHz, DMSO-d6): δ 2.45 (m, 2H), 2.96 (s, 1H), 3.89 (s, 3H), 4.38 (t, 7.0 Hz, 1H), 5.98 (m, 2H), 7.09 (d, 8.3 Hz, 2H), 7.76 (d, 8.3 Hz, 2H), 9.65 (d, 5.4 Hz, 1H).

(x) Synthesis of (R)-4-(4-chlorobenzenesulfonyl)-3-(prop-2-ynyl)-3 4-dihydropyrazin-2(1)-one (48)

Using the procedure described for 45, (R)-N-(2,2-dimethoxyethyl)-2-(4-chlorobenzenesulfonamido)pent-4-ynamide afforded the title compound as a tan solid. 1H NMR (300 MHz, DMSO-d$_6$): δ 2.98 (s, 1H), 3.35 (d, 7.0 Hz, 2H), 4.35 (t, 7.0 Hz, 1H), 5.98 (d, 5.4 Hz, H), 6.01 (t, 5.4 Hz, 1H), 7.71 (d, 8.0 Hz, 2H), 7.81 (d, 8.0 Hz, 2H), 9.65 (s, 1H).

(xi) Synthesis of (R)-N-(2,2-dimethoxyethyl)-2-(3-trifluoromethylbenzenesulfonamido)-pent-4-ynamide (49)

Using the procedure described for compound 45, (R)-N-(2,2-dimethoxyethyl)-2-(3-trifluoromethylbenzenesulfonamido)pent-4-ynamide afforded the title compound as a brown oil. $^1$H NMR (300 MHz, CDCl$_3$): δ 2.05 (s, 1H), 2.65 (m, 2H), 2.85 (s, 3H), 2.96 (s, 3H), 3.35 (m, 2H), 3.96 (t, 6.3 Hz, 1H), 4.32 (t, 5.4 Hz, 1H), 6.86 (t, 5.4 Hz, 1H), 7.68 (t, 7.8 Hz, 1H), 7.82 (d, 7.8 Hz, 1H), 7.97 (s, 1H), 8.03 (d, 7.8 Hz, 1H), 8.11 (s, 1H).

(xii) Synthesis of (R)-4-(3,4-dichlorobenzenesulfonyl)-3-(prop-2-ynyl)-3,4-dihydropyrazin-2(1H)-one (50)

A solution of (R)-2-(3,4-dichlorobenzenesulfonamido)-N-(2,2-dimethoxyethyl)pent-4-ynamide (36.7 g, 89.6 mmol) in 500 mL p-dioxane was treated with TsOH.H$_2$O (5.11 g, 26.9 mmol). The reaction was heated to 60° C. for 7 h and then at 80° C. for 19 h. The mixture was cooled to room temperature and concentrated under reduced pressure. The residue was diluted with 400 mL EtOAc stirred with 400 mL 5% NaHCO$_3$. The resulting precipitate was filtered and washed with H$_2$O. The solid was suspended in hot EtOH and cooled to rt. The solid was collected by filtration, washed with EtOH and dried in vacuo to yield the title compound.

(xiii) Synthesis of (R)-4-(benzenesulfonyl)-3-(prop-2-ynyl)piperazin-2-one (51)

To a stirred mixture of (R)-4-(benzenesulfonyl)-3-(Prop-2-ynyl)-3,4-dihydropyrazin-2(1H)-one (2.7 g, 9.77 mmol) and Et$_3$SiH (16 mL, 97.7 mmol) in CH$_2$Cl$_2$ (30 mL) was added TFA (16.7 g, 147 mmol). The reaction mixture was refluxed for 24 h and cooled. The mixture was concentrated and triturated with ether. The solid was filtered and air-dried to afford the title compound. $^1$H NMR (300 MHz, CDCl$_3$): δ 2.02 (s, 1H), 2.45 (s, 3H), 2.85 (m, 1H), 2.97 (m, 1H), 3.24 (m, 2H), 3.81 (m, 2H), 4.48 (t, 4.7 Hz, 1H), 6.47 (s, 1H), 7.55 (m, 3H), 7.78 (d, 8.3 Hz, 2H).

(xiv) Synthesis of (R)-4-(4-methylbenzenesulfonyl)-3-(Prop-2-ynyl)piperazin-2-one (52)

To a stirred mixture of (R)-4-(4-methylbenzenesulfonyl)-3-(prop-2-ynyl)-3,4-dihydropyrazin-2(1H1)-one (10.0 g, 34.5 mmol) and Et$_3$SiH (55 mL, 345 mmol) in 100 mL CH$_2$Cl$_2$ was added TFA (59 g, 517 mmol). The reaction mixture was refluxed for 16 h. The solution was concentrated and purified by SiO$_2$ (2% MeOH/CH$_2$Cl$_2$) to give an off white solid. $^1$H NMR (300 MHz, CDCl$_3$): δ 2.02 (s, 1H), 2.45 (s, 3H), 2.85 (m, 1H), 2.97 (m, 1H), 3.24 (m, 2H), 3.81 (m, 2H), 4.48 (t, 4.7 Hz, 1H), 6.47 (s, 1H), 7.41 (d, 8.3 Hz, 2H), 7.78 (d, 8.3 Hz, 2H).

(xv) Synthesis of (R)-4-(4-methoxylbenzenesulfonyl)-3-(prop-2-ynyl)piperazin-2-one (53)

Using the procedure described for compound 51, (R)-4-(4-methoxylbenzenesulfonyl)-3-(prop-2-ynyl)-3,4-dihydropyrazin-2(1H)-one afforded the title compound as a tan solid. $^1$H NMR (300 MHz, DMSO-d6): δ 2.65 (m, 1H), 2.86 (m, 2H), 2.90 (s, 1H), 3.05 (m, 1H), 3.61 (m, 2H), 3.87 (s, 3H), 4.25 (t, 5.4 Hz, 1H), 7.08 (d, 8.3 Hz, 2H), 7.81 (d, 8.3 Hz, 2H), 8.06 (s, 1H).

(xvi) Synthesis of (R)-4-(4-chlorobenzenesulfonyl)-3-(prop-2-ynyl)piperazin-2-one (54)

Using the procedure described for compound 51, (R)-4-(4-chlorobenzenesulfonyl)-3-(prop-2-ynyl)-3,4-dihydropyrazin-2(1H)-one afforded the title compound as a tan solid. $^1$H NMR (300 MHz, CDCl$_3$): δ 2.02 (s, 1H), 2.45 (s, 3H), 2.85 (m, 1H), 2.97 (m, 1H), 3.24 (m, 2H), 3.81 (m, 2H), 4.48 (t, 4.7 Hz, 1H), 6.47 (s, 1H), 7.55 (d, 8.0 Hz, 2H), 7.78 (d, 8.0 Hz, 2H).

(xvii) Synthesis of (R)-3-(prop-2-ynyl)-4-(3-(trifluoromethyl)benzenesulfonyl)piperazin-2-one (55)

Using the procedure described for compound 51, (R)-4-(3-trifluoromethylbenzenesulfonyl)-3-(prop-2-ynyl)-3,4-dihydropyrazin-2(1H)-one afforded the title compound as a tan solid.

Reference 6

Synthesis of (R)-3-(prop-2-ynyl)-4-tosyl-3,4-dihydropyrido[3,2-b]pyrazin-2(1H)-one

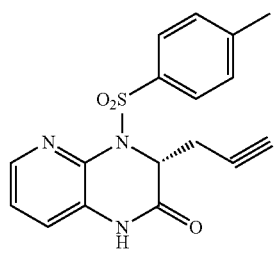

Step (i): Synthesis of (R)-methyl 2-(3-nitropyridin-2-ylamino)pent-4-ynoate (R)-1-methoxy-1-oxopent-4-yn-2-aminium chloride (6.16 g, 38 mmol) in DMSO (100 mL) added 2-chloro-3-nitropyridine (9.0 g, 56 mmol) and then 2-chloro-3-nitropyridine (9.0 g, 56 mmol). The reaction mixture was stirred for 5 d. EtOAC (500 mL) was added and the diluted reaction mixture was washed with 4×brine (200 mL), dried, evaporated to give 10 g of crude material which was purified by column chromatograph (silica gel, 20-100% hex/tolune, EtOAc) to give the title compound.

Step (ii): Synthesis of (R)-3-(prop-2-ynyl)-3,4-dihydropyrido[3,2-b]pyrazin-2(1H)-one To (R)-methyl 2-(3-nitropyridin-2-ylamino)pent-4-ynoate (2.6 g, 10 mmol) in MeOH (60 mL) was added ammonium chloride (2.8 g, 52 mmol) in water (50 mL) and iron (2.7 g, 48 mmol) and the reaction mixture was heated to reflux for 8 h. The reaction mixture was cooled to room temperature and Et$_3$N (1.3 mL) was added. After 10 h, EtOAc (100 mL) was added and the mixture was stirred for 2 h. The solution was decanted and evaporated. Water (15 mL) was added and the reaction mixture was filtered and washed with water to give colored solid.

Step (iii): Synthesis of (R)-3-(prop-2-ynyl)-4-tosyl-3,4-dihydropyrido[3,2-b]pyrazin-2(1H)-one To (R)-3-(prop-2-ynyl)-3,4-dihydropyrido[3,2-b]pyrazin-2(1H)-one (0.42 g, 2244 μmol) in pyridine was added p-toluenesulfonyl chloride (642 mg, 3365 μmol). The reaction mixture was stirred for 7 h and then EtOAc was added. The organic layer was separated, washed with brine, brine/5mL 10% HCl, dried, evaporated to give 0.52 g of solid. Purification by column chromatograph (DCM to 20% EtOAc/DCM) gave the title compound. MS 342 (M+1).

Reference 7

Synthesis of 2-(4-(2-azidoethyl)phenyl)-4,5-dihydro-1H-imidazole

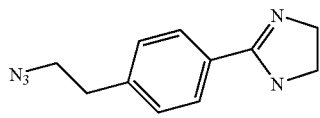

was prepared according to the procedures described in PCT application publication Nos. WO2004054584A1 and WO2004083173A2.

Reference 8

Synthesis of 5-azido-2-(2-(tert-butyldiphenylsilyloxy)ethyl)-5,6,7,8-tetrahydroquinazoline

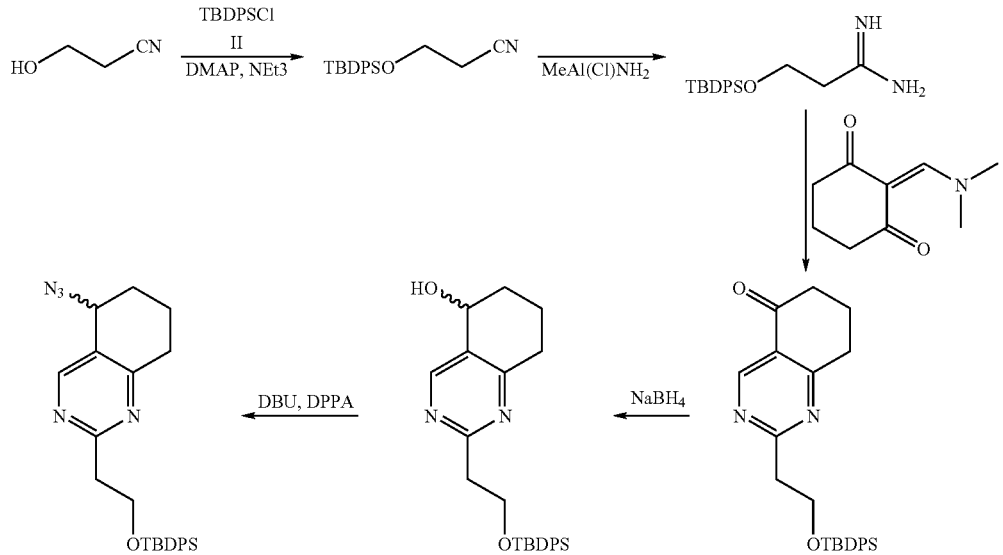

Step (i): Synthesis of 3-(tert-butyldiphenylsilyloxy)-propanenitrile

To a solution of 3-hydroxypropanenitrile (7.1 g, 0.1 mol) and DMAP (1.22 g, 0.01 mmol) in dry DCM (30 mL) at room temperature was added $NEt_3$ (30.3 g, 0.3 mol), followed by TBDPSCl (27.5 g, 0.1 mol). A lot of white solid appeared. After stirring at room temperature overnight, the reaction mixture was quenched with sat. $NH_4Cl$ solution, extracted with DCM, dried over $Na_2SO_4$, and evaporated in vacuo. Flash chomatography ($SiO_2$, hexane/EtOAc=100:2 to 100:5 to 100:10) of the crude material gave the title compound as a white solid.

Step (ii): Synthesis of 3-(tert-butyldiphenylsilyloxy)-propanamidine

To a suspension of $NH_4Cl$ (5.35 g, 0.1 mol) in dry benzene (60 mL) at 0° C. was slowly added a solution of trimethylaluminum in toluene (50 mL of 2 M). After the addition was complete, the reaction mixture was allowed to warm up to room temperature and was stirred for 2 h until gas evolution had ceased. A solution of 3-(tert-butyldiphenylsilyloxy)propanenitrile (9.27 g, 0.03 mol) in dry benzene (20 mL) was added to the aluminum amide reagent and the resulting mixture was heated up to 80° C. for 20 h. The reaction mixture was slowly cooled to room temperature and then carefully poured into a slurry of 300 mL of DCM and 200 g of silica gel. It was then filtered and washed thoroughly with MeOH/DCM (1:2). After concentration, flash chomatography ($SiO_2$, EtOAc to EtOAc/MeOH=100:20 to 100:30 to EtOAc/2M $NH_3$ in MeOH=100:30) gave the title compound as a white solid.

Step (iii): Synthesis of 2-(2-(tert-butyldiphenylsilyloxy)ethyl)-7,8-dihydroquinazolin-5(6H)-one A solution of 3-(tert-butyldiphenylsilyloxy)propanamidine (25 g, 77 mmol) and 2-((dimethylamino)methylene)cyclohexane-1,3-dione (12.8 g, 77 mmol) in dry EtOH (400 mL) was heated at 80° C. for 3 h. After cooling to room temperature, the solvent was evaporated. Flash chomatography ($SiO_2$, EtOAc/hexane=1:1) gave the title compound as a white solid.

Step (iv): Synthesis of 2-(2-(tert-butyldiphenylsilyloxy)ethyl)-5,6,7,8-tetrahydro-quinazolin-5-ol A solution of 2-(2-(tert-butyldiphenylsilyloxy)ethyl)-7,8-dihydroquinazolin-5(6H)-one (2.16 g, 5 mmol) in 30 mL of dry MeOH was treated with $NaBH_4$ (189 mg, 5 mmol). After 5 min, the reaction was quenched with 5 mL of sat. $NH_4Cl$ solution. The MeOH was evaporated and the residue was extracted with DCM, dried over $Na_2SO_4$ and evaporated. Flash chomatography ($SiO_2$, DCM to EtOAc) gave the desired product as a white solid.

Step (v): Synthesis of 5-azido-2-(2-(tert-butyldiphenylsilyloxy)ethyl)-5,6,7,8-tetrahydro-quinazoline To a solution of 2-(2-(tert-butyldiphenylsilyloxy)ethyl)-5,6,7,8-tetrahydro-quinazolin-5-ol (2.0 g, 4.63 mmol) in 25 mL of toluene at −10° C. was added DPPA (1.2 mL, 5.56 mmol). To this stirred solution was then added DBU (0.83 mL, 5.56 mmol) dropwise while keeping the temperature below 0° C. After stirring at room temperature for 16 h, the reaction was evaporated to dryness and directly submitted to flash chomatography (SiO$_2$, hexane/DCM=1:2) to afford the title compound as a white solid.

Example 1

Synthesis of (R)-3-((1-((R)-3,4-dihydro-2H-chromen-4-yl)-1H-1,2,3-triazol-4-yl)methyl)-4-(4-methylbenzenesulfonyl)-3,4-dihyropyrazin-2(1H)-one derivatives 60-62

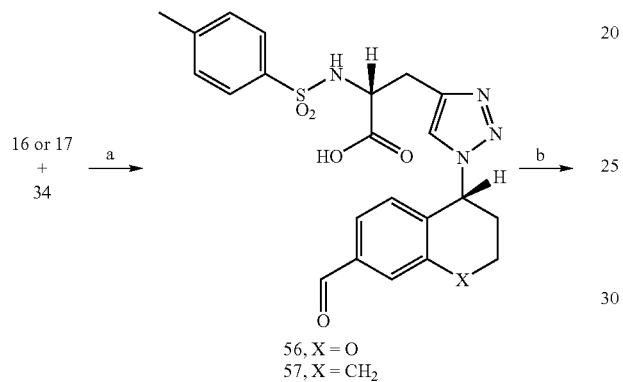

56, X = O
57, X = CH$_2$

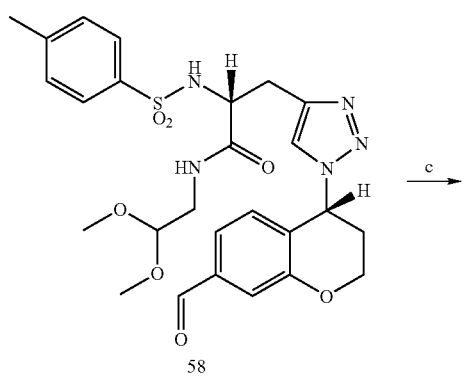

58

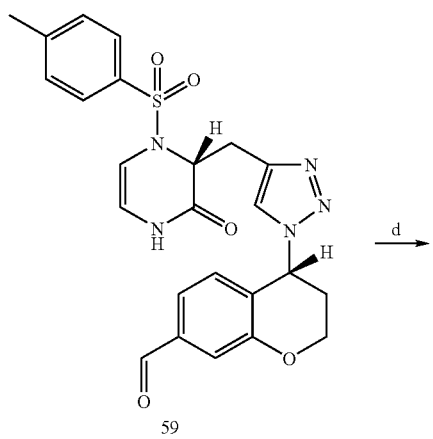

59

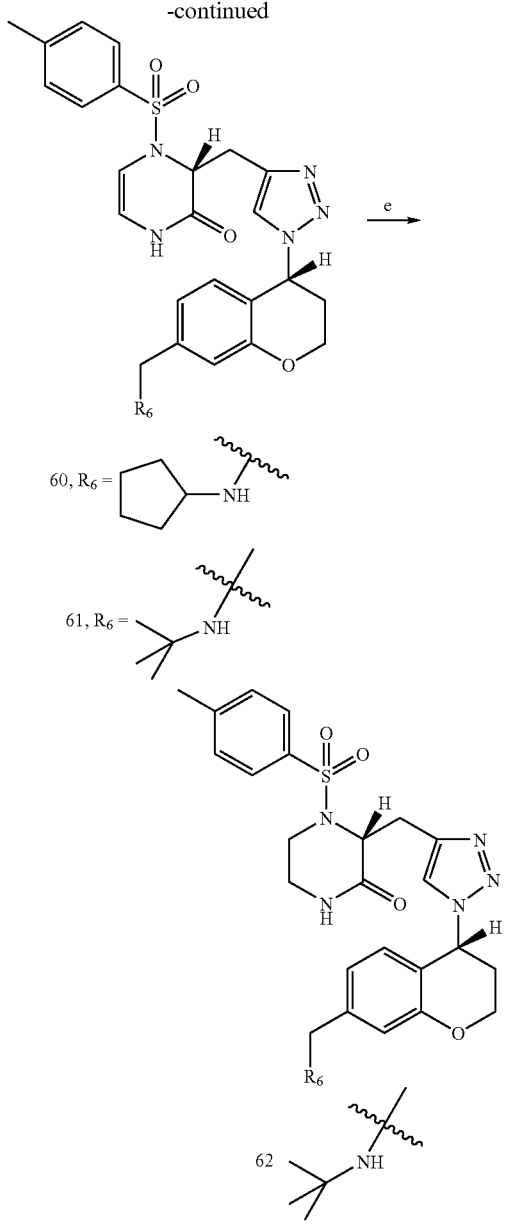

60, R$_6$ =

61, R$_6$ =

62

Reagents and Conditions:
a  Sodium ascorbate, CuSO$_4$•5H2O, t-BuOH/water;
b  (2,2-dimethoxyethyl)amine, HOAt, DIPEA;
c  TsOH, 60° C.;
d  substituted amine, NaBH(OAc)$_3$, HOAc;
e  H$_2$, 10% Pd on C.

Step (i): Synthesis of (R)-3-(1-((R)-7-formyl-3,4-dihydro-2H-chromen-4-yl)-1H-1,2,3-triazol-4-yl)-2-(4-methylbenzenesulfonamido)propanoic acid (56)

To a stirred mixture of (R)-2-(4-methylbenezenesulfonamido)pent-4-ynoic acid (1.32 g, 4.92 mmol) and (R)-4-azido-3,4-dihydro-2H-chromen-7-carbaldehyde (1.01 g, 4.92 mmol) in 20 mL t-BuOH was added sodium ascorbate (0.10 g, 0.49 mmol in 500 μL H$_2$O) and CuSO$_4$.5 H$_2$O (0.13 g, 0.49 mmol in 500 μL H$_2$O). An additional portion of H$_2$O (5 mL) was added, and the reaction was stirred for 24 h at RT. The reaction mixture was diluted with H$_2$O, and a precipitate had formed. The yellow solid was filtered and air-dried to afford the title compound. MS (m/z): 472.3 (m+H).

Using the same method described for 56, (R)-5-azido-5,6,7,8-tetrahydronapthalene-2-carbaldehyde afforded (R)-3-(1-((R)-6-formyl-1,2,3,4-tetrahydronaphthalen-1-yl)-1H-1,2,3-triazol-4-yl)-2-(4-methylphenylsulfonamido)propanoic acid (57)

Step (ii): Synthesis of (R)-4-(4-(((R)-3-oxo-1-(4-methylbenzenesulfonamido)-1,2,3,4-tetra-hydropyrazin-2-yl)methyl)-1H-1,2,3-triazol-1-yl)-3,4-dihydro-2H-chromene-7-carbaldehyde (58)

A mixture of (R)-3-(1-(R)-7-formylchroman-4-yl)-1H-1,2,3-triazol-4-yl)-2-(4-methylbenzenesulfonamido)propanoic acid (1.24 g, 2.66 mmol), HOAt (0.43 g, 3.19 mmol), i-Pr₂NEt (0.70 g, 5.3 mmol), (2,2-dimethoxy)ethylamine (0.33 g, 2.7 mmol), and EDCI (0.61 g, 3.2 mmol) in 20 mL DMF was stirred for 24 h at RT. The reaction mixture was concentrated, taken up in H₂O and extracted with EtOAc (3×). The combined extracts were dried over MgSO₄, concentrated to afford 83. The brown oil was dissolved in dioxane (30 mL), treated with p-toluenesulfonic acid (0.4 g) and heated to 60° C. for 36 h. The reaction mixture was cooled, concentrated and taken up in H₂O. The formed solid was filtered and purified by SiO₂ (3% MeOH/CH₂Cl₂) to give a yellow solid.

Step (iii): Synthesis of (R)-3-((1-((R)-7-((N-(cyclopentyl)amino)methyl-3,4-dihydro-2H-chromen-4-yl)-1H-1,2,3-triazol-4-yl)methyl)-4-(4-methylbenzenesulfonyl)-3,4-dihydro-pyrazin-2(1H)-one (60)

Using the procedure described for 61, cyclopentylamine afforded the title compound. MS (m/z): 563.4 (m+H).

Step (iv): Synthesis of (R)-3-((1-((R)-7-(((2,2-dimethylethyl)amino)methyl-3,4-dihydro-2H-chromen-4-yl)-1H-1,2,3-triazol-4-yl)methyl)-4-(4-methylbenzenesulfonyl)-3,4-dihydro-pyrazin-2(1H)-one (61)

A mixture of (R)-4-(4-(((R)-3-oxo-1-(4-methylbenzenesulfonyl)-1,2,3,4-tetra-hydropyrazin-2-yl)methyl)-1H-1,2,3-triazol-1-yl)-3,4-dihydro-2H-chromene-7-carbaldehyde (0.22 g, 0.45 mmol) and t-BuNH₂ in 10 mL of 1,2-dichloroethane was heated to 80° C. in a sealed tube for 30 min. The reaction mixture was cooled, and successively treated with NaBH(OAc)₃ and HOAc (1 drop). The reaction mixture was heated to 60° C. for 16 h. The mixture was cooled, taken up in H₂O and extracted with CHCl₃ (3×). The combined extracts were dried over MgSO₄, concentrated, and washed with ether to afford the title compound. MS (m/z): 551.4 (m+H).

Step (v): Synthesis of (R)-3-((1-((R)-7-((N-(2,2-dimethylethyl)amino)methyl-3,4-dihydro-2H-chromen-4-yl)-1H-1,2,3-triazol-4-yl)methyl)-4-(4-methylbenzenesulfonyl)piperazin-2-one, TFA salt (62)

A solution of (R)-3-((1-((R)-7-((N-(2,2-dimethylethyl)amino)methyl-3,4-dihydro-2H-chromen-4-yl)-1H-1,2,3-triazol-4-yl)methyl)-4-(4-methylbenzenesulfonyl)-3,4-dihydro-pyrazin-2(1H)-one (0.15 g, 0.27 mmol) in 2 mL MeOH was treated with 10% Pd/C (20 mg) and hydrogenated (balloon) overnight at RT. The catalyst was filtered, and the filtrate was concentrated. The residue was purified by reverse phase HPLC to afford a white solid. MS (m/z): 553.4 (m+H).

Example 2

Synthesis of (R)-3-((1-((R)-1,2,3,4-tetrahydronaphthalen-1-yl)-1H-1,2,3-triazol-4-yl)methyl)-4-(4-methylbenzenesulfonyl)-3,4-dihydropyrazin-2(1H)-one derivatives 64-65

46 + 16 —a→

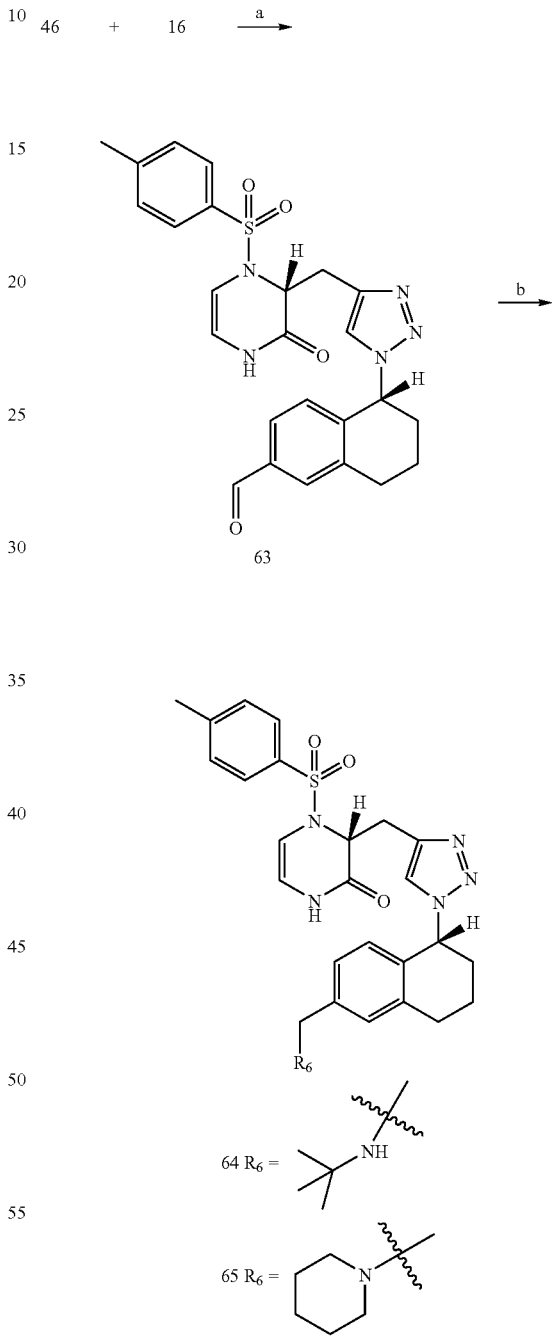

Reagents and conditions:
a sodium ascorbate, CuSO₄·5H₂O, t-BuOH/water;
b substituted amine, NaBH(OAc)₃, HOAc.

Step (i): Synthesis of (R)-5(4-(((R)-3-oxo-1-(4-methylbenzenesulfonyl)-1,2,3,4-tetra-hydropyrazin-2-yl)methyl)-1H-1,2,3-triazol-1-yl)-5,6,7,8-tetrahydronaphthalen-2-carbaldehyde (63)

(R)-3-(Prop-2-ynyl)-4-(4-methylbenzenesulfonyl)-3,4-dihydropyrazin-2(1H)-one (2.5 mmol, 1.0 eq) and (R)-5-azido-5,6,7,8-tetrahydronaphthalene-2-carbaldehyde (2.5 mmol, 1 eq) were placed in t-BuOH to stir. An aqueous solution of sodium ascorbate (600 μL, 0.1 eq) was added, followed by the addition of an aqueous solution of $CuSO_4.5H_2O$ (600 μL, 0.1 eq). The reaction mixture was allowed to stir overnight. The solvents were removed and the residue was purified by $SiO_2$ (1 to 5% MeOH in DCM) to afford the title compound. MS (m/z): 492.4 (m+H).

Step (ii): Synthesis of (R)-3-((1-((R)-6-((2,2-dimethylethylamino)methyl)-1,2,3,4-tetrahydronaphthalen-1-yl)-1H-1,2,3-triazol-4-yl)methyl)-4-(4-methylbenzenesulfonyl)-3,4-dihydropyrazin-2(1H)-one (64)

(R)-5-(4-(((R)-3—Oxo-1-(4-methylbenzenesulfonyl)-1,2,3,4-tetrahydropyrazin-2-yl)-methyl)-1H-1,2,3-triazol-1-yl)-5,6,7,8-tetrahydronaphthalene-2-carbaldehyde (1.1 mmol, 1 eq) was dissolved in DCE and treated with 4 Å powdered molecular sieves. To the solution was added t-butyl amine (3.2 mmol, 3.0 eq) and AcOH (3.2 mmol, 3.0 eq). The reaction stirred at RT overnight. $NaBH(OAc)_3$ (3.3 mmol, 3.0 eq) was added and after 3 h, the solvent was removed and the residue was purified by $SiO_2$ to afford amine the title compound (MS (m/z): 549.3 (m+H)).

Using the procedure described for 64 but substituting t-butylamine with piperidine afforded (R)-3-((1-((R)-6-(piperidin-1-ylmethyl)-1,2,3,4-tetrahydronaphthalen-1-yl)-1H-1,2,3-triazol-4-yl)methyl)-4-(4-methylbenzenesulfonyl)-3,4-dihydropyrazin-2(1H)-one (65). MS (m/z): 575.1 (m+H)).

Example 3

Synthesis of (R)-4-(3,4-dichlorobenzenesulfonyl)-3-((1-((R)-1-(4-(piperidin-1-ylmethyl)-phenyl)ethyl)-1H-1,2,3-triazol-4-yl)methyl)-3,4-dihydropyrazin-2(1H)-one

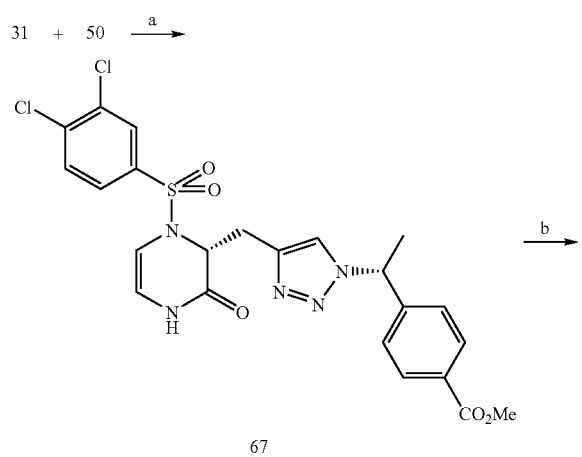

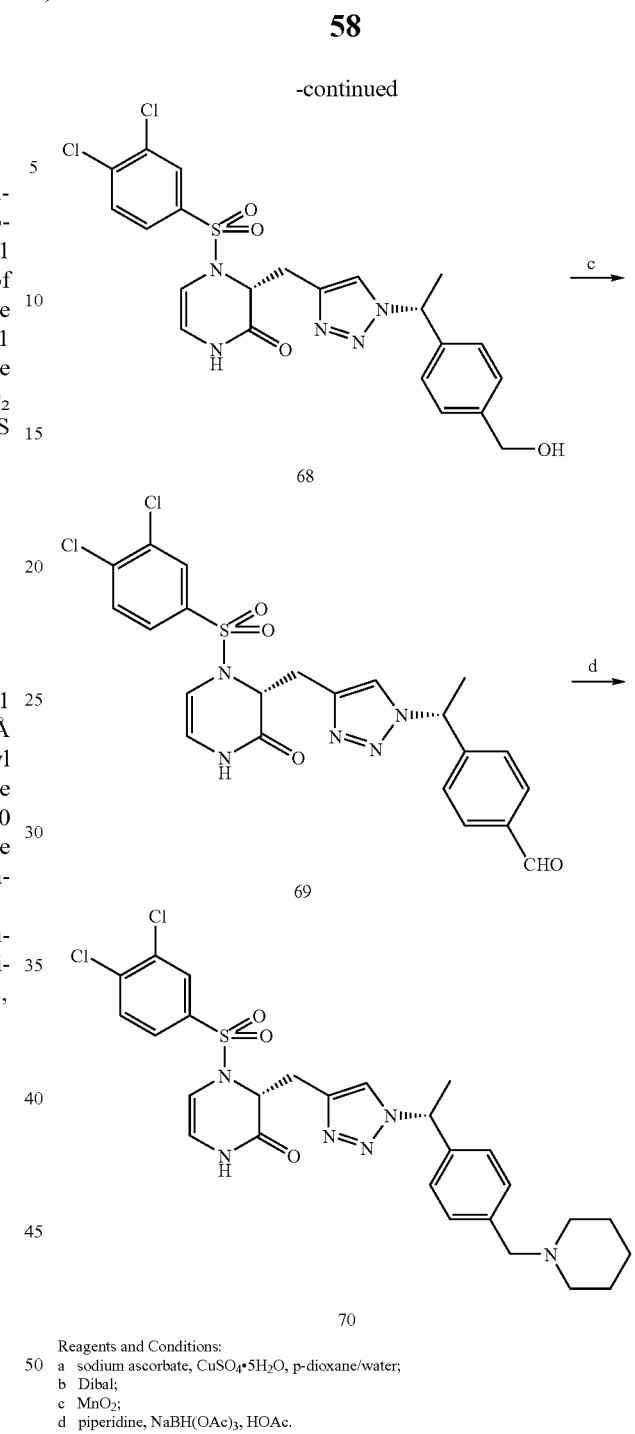

Reagents and Conditions:
a  sodium ascorbate, $CuSO_4·5H_2O$, p-dioxane/water;
b  Dibal;
c  $MnO_2$;
d  piperidine, $NaBH(OAc)_3$, HOAc.

Step (i): Synthesis of methyl 4-((R)-1-(4-(((R)-1-(3,4-dichlorobenzenesulfonyl)-3-oxo-1,2,3,4-tetrahydropyrazin-2-yl)methyl)-1H-1,2,3-triazol-1-yl)ethyl)benzoate (67)

To a solution of (R)-4-(3,4-dichlorobenzenesulfonyl)-3-(prop-2-ynyl)-3,4-dihydro-pyrazin-2(1H)-one (1.46 g, 4.24 mmol) and (R)-methyl 4-(1-azidoethyl)benzoate (0.870 g, 4.24 mmol) in dioxane (80 mL) and tert-butanol (120 mL) were added $CuSO_4.5H_2O$ (1.11 g, 4.46 mmol in 8.0 mL $H_2O$) and sodium-L-ascorbate (0.880 g, 4.44 mmol in 8.0 mL $H_2O$). After 5 min, $H_2O$ (40 mL) was added and the reaction mixture was stirred for 16 h. The solvent was concentrated to approximately 40 mL under reduced pressure and diluted with 200 mL EtOAc. The layers were separated and the aqueous layer was extracted with EtOAc (1×100 mL). The extracts were washed with 5% NaHCO$_3$ (200 mL×2), brine (200 mL×2), dried over Na$_2$SO$_4$ and concentrated under reduced pressure. The crude product was chromatographed on silica (100% CH$_2$Cl$_2$ to 10% MeOH in CH$_2$Cl$_2$) to yield the title compound.

Step (ii): Synthesis of (R)-4-(3,4-Dichlorobenzenesulfonyl)-3-((1-((R)-1-(4-(hydroxymethyl)-phenyl)ethyl)-1H-1,2,3-triazol-4-yl)methyl)-3,4-dihydropyrazin-2(1H)-one (68)

Methyl 4-((R)-1-(4-(((R)-1-(3,4-dichlorobenzenesulfonyl)-3-oxo-1,2,3,4-tetrahydro-pyrazin-2-yl)methyl)-1H-1,2,3-triazol-1-yl)ethyl)benzoate (1.38, 2.51 mmol) was dissolved in CH$_2$Cl$_2$ (200 mL) and cooled to −78° C. under N$_2$. Dibal (1.5M solution in toluene, 8.4 mL, 12.6 mmol) was then added over 10 min. After 30 min, the cold bath was removed and the reaction was stirred for 4 h. To the solution was added MeOH (20 mL), followed by Na$_2$SO$_4$ (25.1 g) and saturated NH$_4$Cl (2.5 mL). The reaction mixture was stirred overnight. The solids were removed by filtration, and washed with CH$_2$Cl$_2$/MeOH (10/1). The filtrate was concentrated and the residue was chromatographed on silica (100% CH$_2$Cl$_2$ to 5% MeOH in CH$_2$Cl$_2$) to yield the title compound.

Step (iii): Synthesis of 4-((R)-1-(4-(((R)-1-(3 4-dichlorobenzenesulfonyl)-3-oxo-1,2,3,4-tetra-hydropyrazin-2-yl)methyl)-1H-1,2,3-triazol-1-yl)ethyl)benzaldehyde (69)

To a solution of (R)-4-(3,4-dichlorobenzenesulfonyl)-3-((1-((R)-1-(4-(hydroxymethyl)-phenyl)ethyl)-1H-1,2,3-triazol-4-yl)methyl)-3,4-dihydropyrazin-2(1H)-one (0.461 g, 0.882 mmol) in CH$_2$Cl$_2$ (100 mL) was added MnO$_2$ (1.92 g, 22.1 mmol). After 1.5 h, MeOH (20 mL) was added. After the reaction mixture had stirred for 15 min, it was filtered through Celite and the solid was washed with CH$_2$Cl$_2$/MeOH (10/1). The solvent was removed under reduced pressure and dried in vacuo to yield the title compound.

Step (iv): Synthesis of (R)-4-(3,4-dichlorobenzenesulfonyl)-3-((1-((R)-1-(4-(piperidin-1-ylmethyl)phenyl)ethyl)-1H-1,2,3-triazol-4-yl)methyl)-3.4-dihydropyrazin-2(1H)-one (70)

To a solution of 4-((R)-1-(4-(((R)-1-(3,4-dichlorobenzenesulfonyl)-3-oxo-1,2,3,4-tetra-hydropyrazin-2-yl)methyl)-1H-1,2,3-triazol-1-yl)ethyl)benzaldehyde (0.150 g, 0.288 mmol) and piperidine (0.10 mL, 1.01 mmol) in 1,2-dichloroethane (10 mL) was added NaBH(OAc)$_3$ (0.126 g, 0.594 mmol). After 18 h, the solution was diluted with 60 mL EtOAc and washed with 5% NaHCO$_3$ (60 mL×2), brine (60 mL×2), dried over Na$_2$SO$_4$ and concentrated under reduced pressure. The crude product was chromatographed on SiO$_2$ (100% CH$_2$Cl$_2$ to 5% 2N methanolic NH$_3$ in CH$_2$Cl$_2$) to yield the title compound.

Example 4

Synthesis of Ciompounds of Formula (I) Using Parallel Synthesis Method

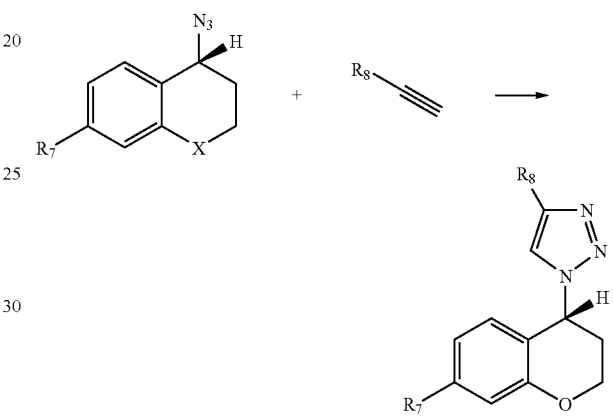

see Table 4

Using the Bohdan Miniblock system, the azide-containing compounds (1.0 eq) in 1 mL t-BuOH were charged to a 2 mL reaction vessel. The alkyne-containing compounds (1.1 eq) were then added. Sodium ascorbate (66.1 μM in H$_2$O) followed by an aqueous solution of CuSO4.5H$_2$O (66.1 M). The reactions were placed on an orbital shaker and allowed to swirl for 3 days. The reactions were purified by loading onto a Agilent AccuBOND II SCX cartridge that had previously been rinsed with MeOH and H$_2$O. The cartridge was washed with MeOH, and the product eluted with 2 M ammonia in MeOH. The solvents were removed using a Genevac to afford the desired product.

| No. | Name | Structure | Mass |
|---|---|---|---|
| 71 | (R)-3-((1-((R)-6-((cyclopentyl-amino)methyl)-1,2,3,4-tetra-hydronaphthalen-1-yl)-1H-1,2,3-triazol-4-yl)methyl)-4-tosyl-3,4-dihydropyrazin-2(1H)-one | 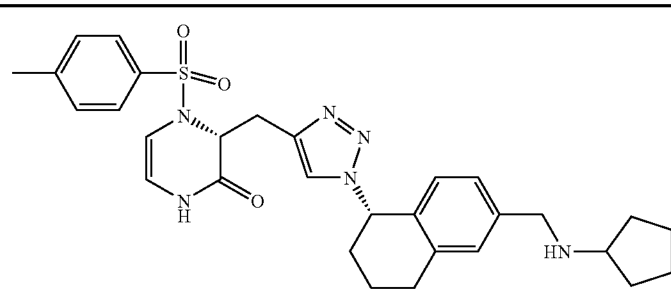 | C$_{30}$H$_{36}$N$_6$O$_3$S<br>Calcd: 560.26<br>Found: 561.3,<br>(M + H) |

-continued

| No. | Name | Structure | Mass |
|---|---|---|---|
| 72 | (R)-3-((1-((R)-6-((4-fluoro-piperidin-1-yl)methyl)-1,2,3,4-tetrahydronaphthalen-1-yl)-1H-1,2,3-triazol-4-yl)methyl)-4-(phenylsulfonyl)-3,4-dihydro-pyrazin-2(1H)-one | 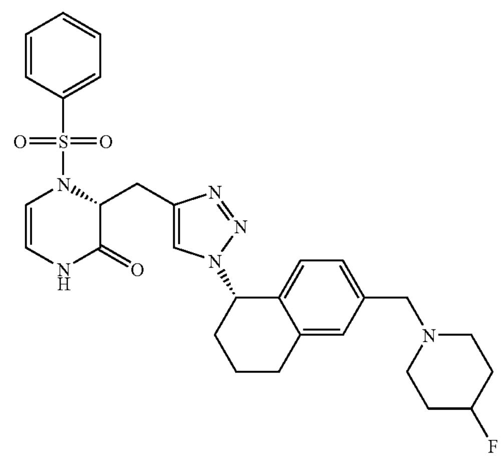 | $C_{29}H_{33}FN_6O_3S$, Calcd: 564.23 Found: 565.2 (M + H) |
| 73 | (R)-4-(4-chlorophenyl-sulfonyl)-3-((1-((R)-6-((4-fluoro-piperidin-1-yl)methyl)-1,2,3,4-tetrahydro-naphthalen-1-yl)-1H-1,2,3-triazol-4-yl)methyl)piperazin-2-one | 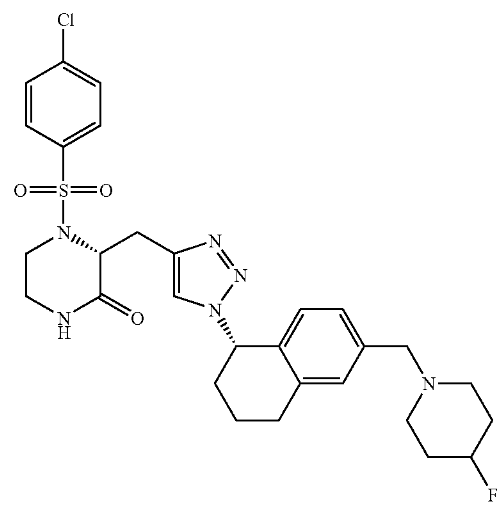 | $C_{29}H_{34}ClFN_6O_3S$ Calcd: 600.21 Found: 601.2 (M + H) |
| 74 | (R)-3-((1-((R)-6-((4-fluoro-piperidin-1-yl)methyl)-1,2,3,4-tetrahydronaphthalen-1-yl)-1H-1,2,3-triazol-4-yl)methyl)-4-(4-methoxyphenylsulfonyl)-piperazin-2-one | 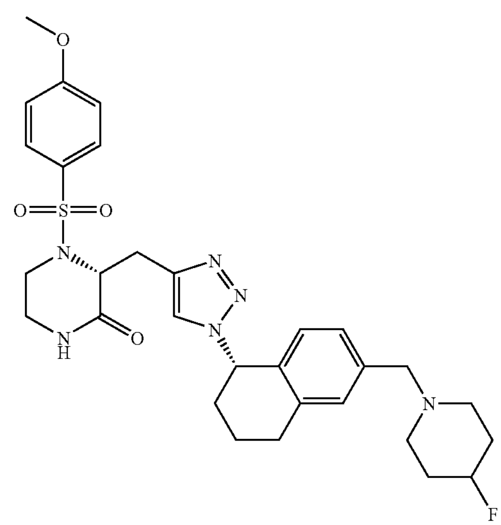 | $C_{30}H_{37}FN_6O_4S$, Calcd: 596.26 Found: 597.3 (M + H) |

| No. | Name | Structure | Mass |
|---|---|---|---|
| 75 | (R)-4-(4-chlorophenyl-sulfonyl)-3-((1-((R)-6-((4-fluoro-piperidin-1-yl)methyl)-1,2,3,4-tetrahydronaphthalen-1-yl)-1H-1,2,3-triazol-4-yl)methyl)-3,4-dihydropyrazin-2(1H)-one | 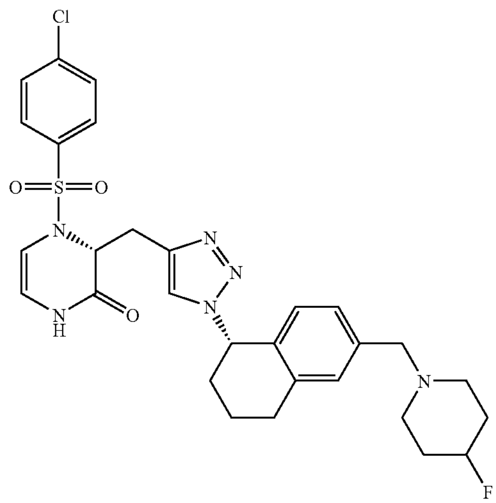 | $C_{29}H_{32}ClFN_6O_3S$ Calcd: 598.19 Found: 599.1 (M + H) |
| 122 | (R)-3-((1-((R)-6-((4-fluoro-piperidin-1-yl)methyl)-1,2,3,4-tetrahydronaphthalen-1-yl)-1H-1,2,3-triazol-4-yl)methyl)-4-(4-methoxyphenylsulfonyl)-3,4-dihydropyrazin-2(1H)-one | 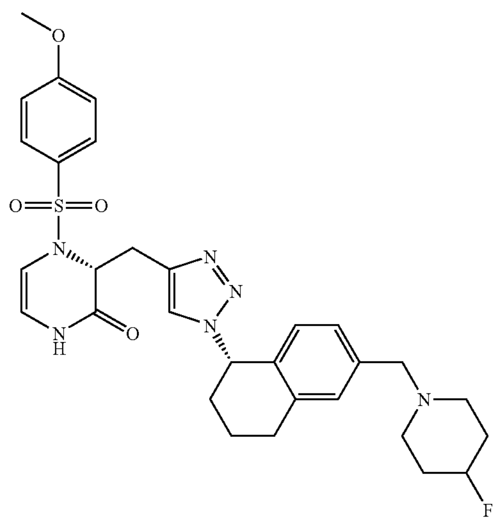 | $C_{30}H_{35}FN_6O_4S$, Calcd: 594.24 Found: 595.2 (M + H) |
| 77 | (R)-3-((1-((R)-6-((cyclopentyl-amino)methyl)-1,2,3,4-tetrahydronaphthalen-1-yl)-1H-1,2,3-triazol-4-yl)methyl)-4-(phenylsulfonyl)piperazin-2-one | 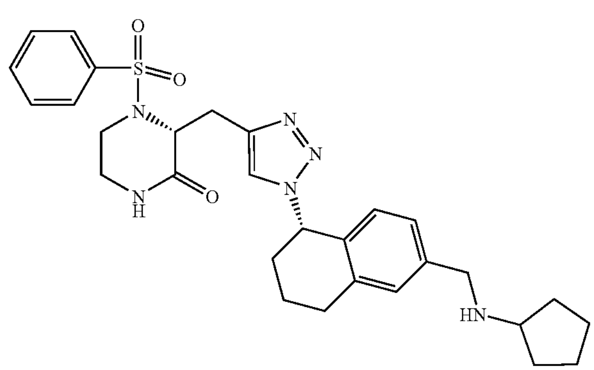 | $C_{29}H_{36}N_6O_3S$, Calcd: 548.26 Found: 549.3 (M + H) |

-continued

| No. | Name | Structure | Mass |
|---|---|---|---|
| 78 | (R)-3-((1-((R)-6-((cyclopentyl-amino)methyl)-1,2,3,4-tetra-hydronaphthalen-1-yl)-1H-1,2,3-triazol-4-yl)methyl)-4-(3-(trifluoromethyl)phenyl-sulfonyl)-3,4-dihydropyrazin-2(1H)-one | 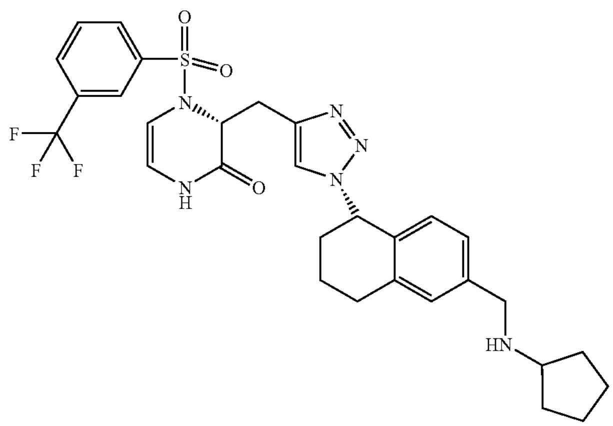 | $C_{30}H_{33}F_3N_6O_3S$, Calcd: 614.23 Found: 615.0 (M + H) |
| 79 | (R)-3-((1-((R)-6-((cyclopentyl-amino)methyl)-1,2,3,4-tetrahydro-naphthalen-1-yl)-1H-1,2,3-triazol-4-yl)methyl)-4-(phenylsulfonyl)-3,4-dihydro-pyrazin-2(1H)-one | 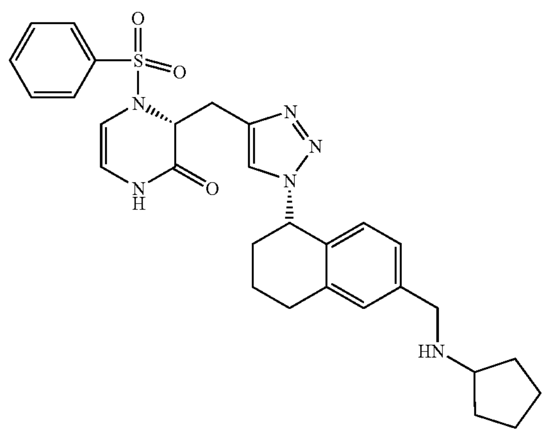 | $C_{29}H_{34}N_6O_3S$, Calcd: 546.24 Found: 547.2 (M + H) |
| 80 | (R)-4-(4-chlorophenyl-sulfonyl)-3-((1-((R)-6-((cyclopentyl-amino)methyl)-1,2,3,4-tetra-hydronaphthalen-1-yl)-1H-1,2,3-triazol-4-yl)methyl)piperazin-2-one | 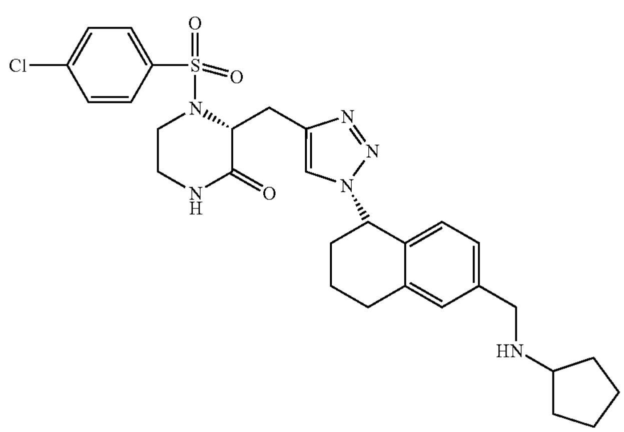 | $C_{29}H_{35}ClN_6O_3S$, Calcd: 582.22 Found: 583.2 (M + H) |

| No. | Name | Structure | Mass |
| --- | --- | --- | --- |
| 81 | (R)-3-((1-((R)-6-((cyclopentyl-amino)methyl)-1,2,3,4-tetra-hydronaphthalen-1-yl)-1H-1,2,3-triazol-4-yl)methyl)-4-(4-methoxyphenylsulfonyl)-piperazin-2-one | 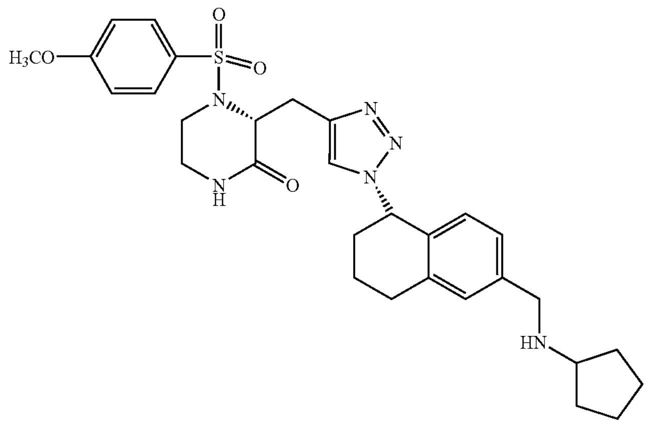 | $C_{30}H_{38}N_6O_4S$, Calcd: 578.27 Found: 579.3 (M + H) |
| 82 | (R)-4-(4-chlorophenyl-sulfonyl)-3-((1-((R)-6-((cyclopentylamino)-methyl)-1,2,3,4-tetrahydro-naphthalen-1-yl)-1H-1,2,3-triazol-4-yl)methyl)-3,4-dihydropyrazin-2(1H)-one | 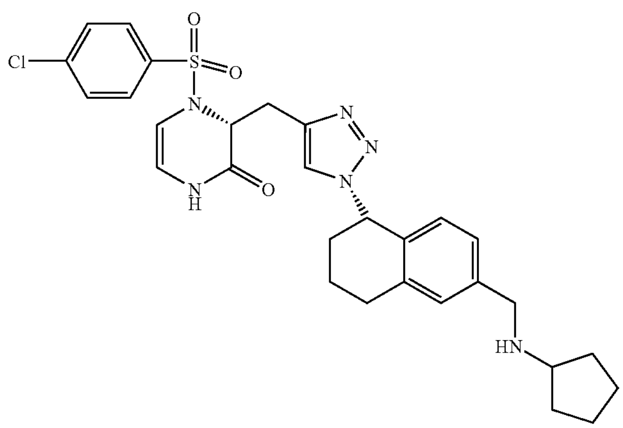 | $C_{29}H_{33}ClN_6O_3S$, Calcd: 580.2 Found: 581.1 (M + H) |
| 83 | (R)-3-((1-((R)-6-((cyclopentyl-amino)methyl)-1,2,3,4-tetra-hydronaphthalen-1-yl)-1H-1,2,3-triazol-4-yl)methyl)-4-(4-methoxyphenylsulfonyl)-3,4-dihydropyrazin-2(1H)-one | 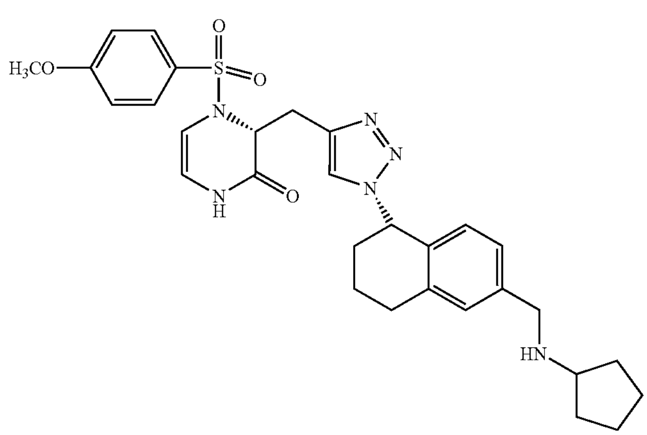 | $C_{30}H_{36}N_6O_4S$, Calcd: 576.25 Found: 577.2 (M + H) |

| No. | Name | Structure | Mass |
|---|---|---|---|
| 84 | (R)-3-((1-((R)-6-((tert-butyl-amino)methyl)-1,2,3,4-tetra-hydronaphthalen-1-yl)-1H-1,2,3-triazol-4-yl)methyl)-4-(phenyl-sulfonyl)piperazin-2-one | 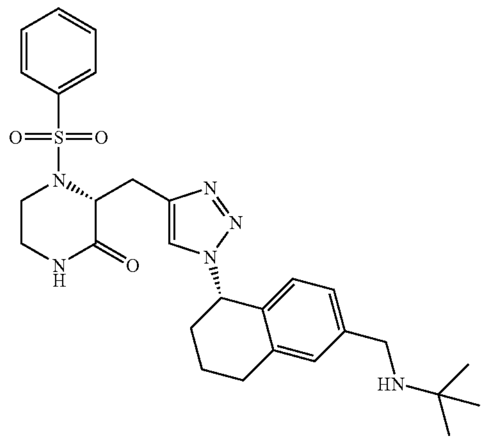 | $C_{28}H_{36}N_6O_3S$, Calcd: 536.26 Found: 537.3 (M + H) |
| 85 | (R)-3-((1-((R)-6-((tert-butyl-amino)methyl)-1,2,3,4-tetra-hydronaphthalen-1-yl)-1H-1,2,3-(trifluoromethyl)phenyl-sulfonyl)-3,4-dihydropyrazin-2(1H)-one | 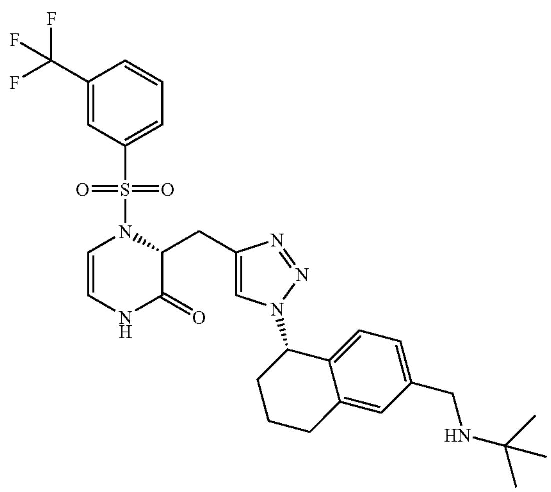 | $C_{29}H_{33}F_3N_6O_3S$, Calcd: 602.23 Found: 603.3 (M + H) |
| 86 | (R)-3-((1-((R)-6-((tert-butyl-amino)methyl)-1,2,3,4-tetrahydro-naphthalen-1-yl)-1H-1,2,3-triazol-4-yl)methyl)-4-(phenylsulfonyl)-3,4-dihydropyrazin-2(1H)-one | 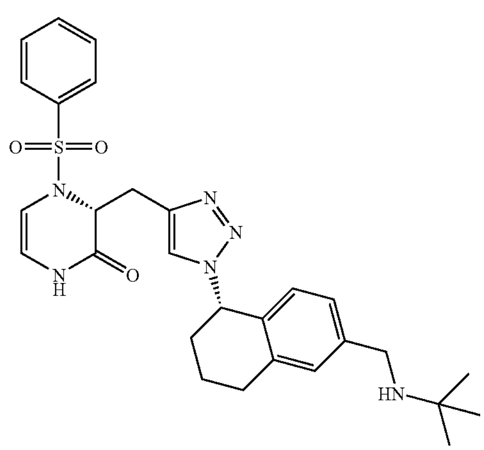 | $C_{28}H_{34}N_6O_3S$, Calcd: 534.24 Found: 535.2 (M + H) |

| No. | Name | Structure | Mass |
|---|---|---|---|
| 87 | (R)-3-((1-((R)-6-((tert-butyl-amino)methyl)-1,2,3,4-tetrahydro-naphthalen-1-yl)-1H-1,2,3-triazol-4-yl)methyl)-4-(4-chlorophenyl-sulfony)piperazin-2-one | 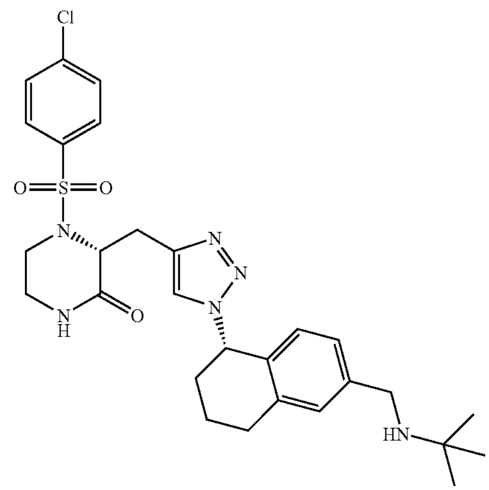 | $C_{28}H_{35}ClN_6O_3S$, Calcd: 570.22 Found: 571.2 (M + H) |
| 88 | (R)-3-((1-((R)-6-((tert-butyl-amino)methyl)-1,2,3,4-tetrahydro-naphthalen-1-yl)-1H-1,2,3-triazol-4-yl)methyl)-4-(4-methoxy-phenyl-sulfonyl)piperazin-2-one | 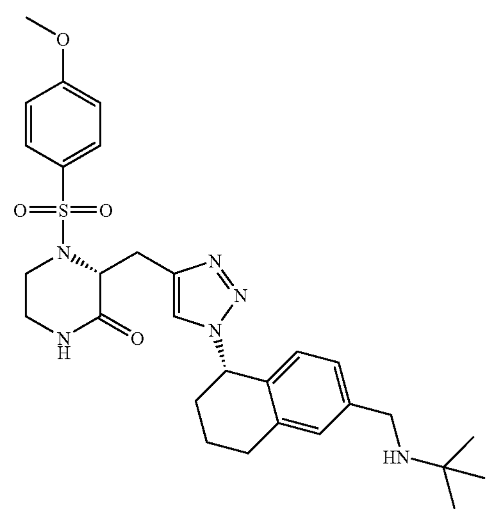 | $C_{29}H_{38}N_6O_4S$, Calcd: 566.27 Found: 567.2 (M + H) |
| 89 | (R)-3-((1-((R)-6-((tert-butyl-amino)methyl)-1,2,3,4-tetrahydro-naphthalen-1-yl)-1H-1,2,3-triazol-4-yl)methyl)-4-(4-chlorophenyl-sulfonyl)-3,4-dihydropyrazin-2(1H)-one | 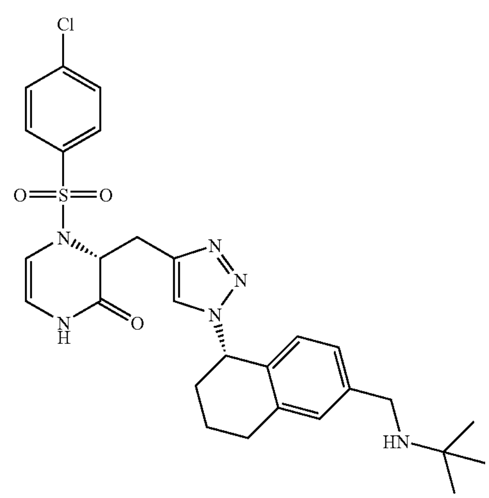 | $C_{29}H_{33}ClN_6O_3S$, Calcd: 568.2 Found: 569.1 (M + H) |

| No. | Name | Structure | Mass |
|---|---|---|---|
| 90 | (R)-3-((1-((R)-6-((tert-butyl-amino)methyl)-1,2,3,4-tetra-hydronaphthalen-1-yl)-1H-1,2,3-triazol-4-yl)methyl)-4-(4-methoxyphenylsulfonyl)-3,4-dihydropyrazin-2(1H)-one | 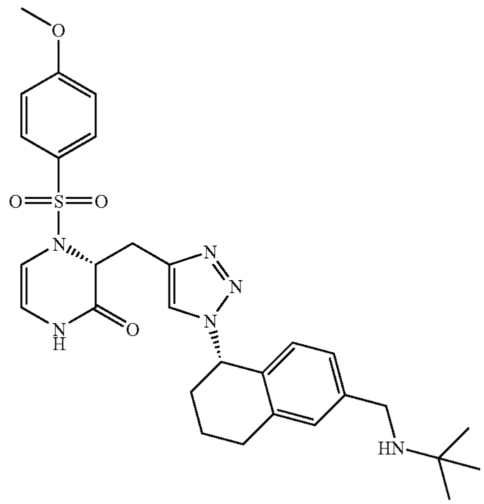 | $C_{29}H_{36}N_6O_4S$, Calcd: 564.25 Found: 565.2 (M + H) |
| 91 | (R)-3-((1-((R)-6-((neopentyl-amino)methyl)-1,2,3,4-tetra-hydronaphthalen-1-yl)-1H-1,2,3-triazol-4-yl)methyl)-4-tosyl-3,4-dihydropyrazin-2(1H)-one | 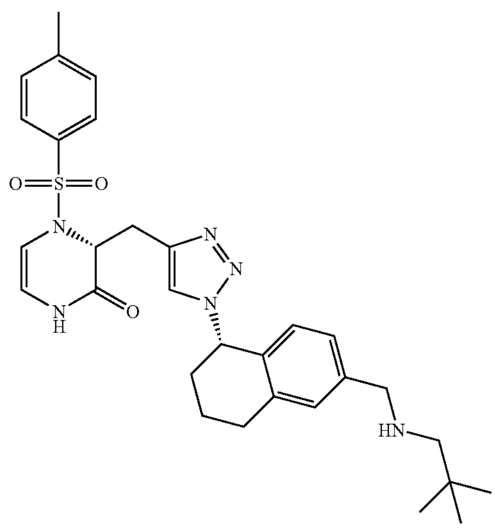 | $C_{30}H_{38}N_6O_3S$, Calcd: 562.27 Found: 563.1 (M + H) |
| 92 | (R)-3-((1-((R)-6-((neopentyl-amino)methyl)-1,2,3,4-tetra-hydronaphthalen-1-yl)-1H-1,2,3-triazol-4-yl)methyl)-4-(phenylsulfonyl)piperazin-2-one | 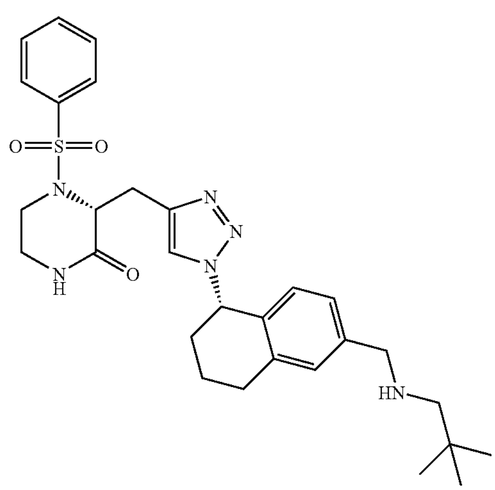 | $C_{29}H_{38}N_6O_3S$, Calcd: 550.27 Found: 551.2 (M + H) |

-continued

| No. | Name | Structure | Mass |
|---|---|---|---|
| 93 | (R)-3-((1-((R)-6-((neopentyl-amino)methyl)-1,2,3,4-tetra-hydronaphthalen-1-yl)-1H-1,2,3-triazol-4-yl)methyl)-4-(3-(trifluoromethyl)phenyl-sulfonyl)-3,4-dihydropyrazin-2(1H)-one | 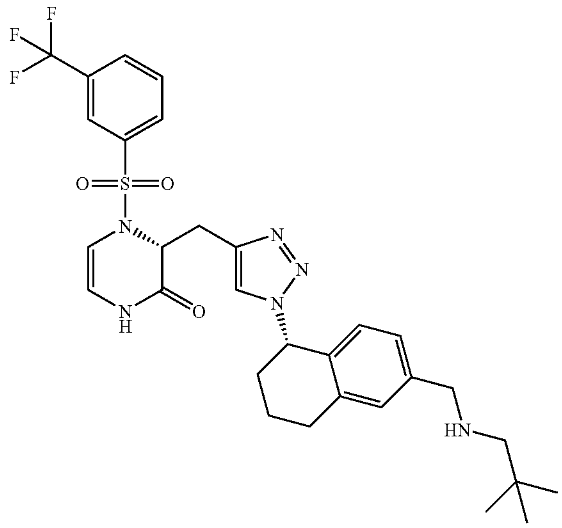 | $C_{30}H_{35}F_3N_6O_3S$, Calcd: 616.24 Found: 617.1 (M + H) |
| 94 | (R)-3-((1-((R)-6-((neopentyl-amino)methyl)-1,2,3,4-tetra-hydronaphthalen-1-yl)-1H-1,2,3-triazol-4-yl)methyl)-4-(phenylsulfonyl)-3,4-dihydro-pyrazin-2(1H)-one | 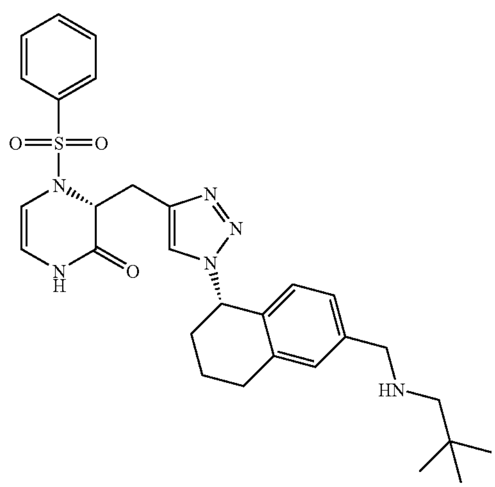 | $C_{29}H_{36}N_6O_3S$, Calcd: 548.26 Found: 549.3 (M + H) |
| 96 | (R)-4-(4-chlorophenylsulfonyl)-3-((1-((R)-6-((neopentylamino)-methyl)-1,2,3,4-tetra-hydronaphthalen-1-yl)-1H-1,2,3-triazol-4-yl)methyl)-piperazin-2-one | 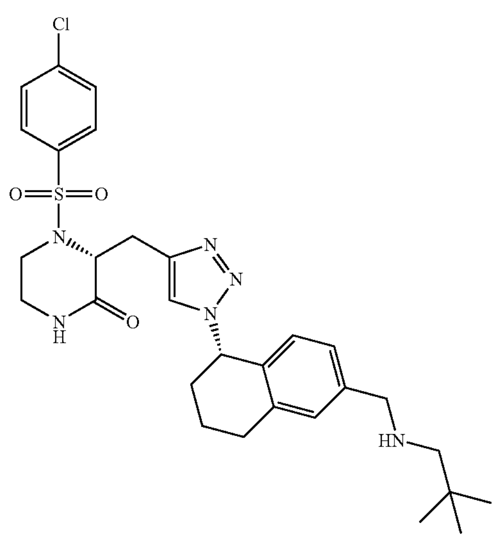 | $C_{29}H_{37}ClN_6O_3S$, Calcd: 584.23 Found: 585.0 (M + H) |

-continued

| No. | Name | Structure | Mass |
|---|---|---|---|
| 97 | (R)-4-(4-chlorophenyl-sulfonyl)-3-((1-((R)-6-((neopentylamino)-methyl)-1,2,3,4-tetra-hydronaphthalen-1-yl)-1H-1,2,3-triazol-4-yl)methyl)-3,4-dihydropyrazin-2(1H)-one | 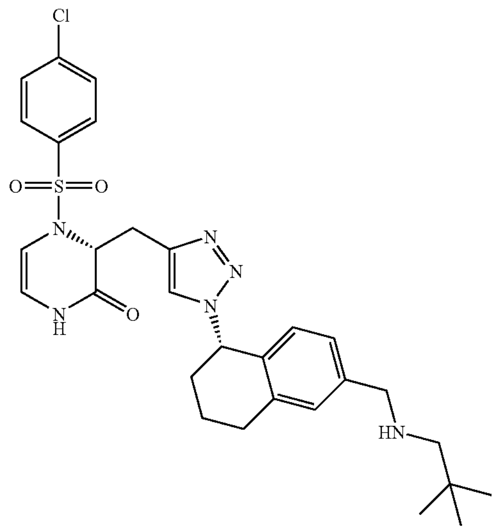 | $C_{29}H_{35}ClN_6O_3S$, Calcd: 582.22 Found: 583.2 (M + H) |
| 98 | (R)-4-(4-methoxyphenyl-sulfonyl)-3-((1-((R)-6-((neopentylamino)methyl)-1,2,3,4-tetrahydronaphthalen-1-yl)-1H-1,2,3-triazol-4-yl)methyl)-3,4-dihydro-pyrazin-2(1H)-one | 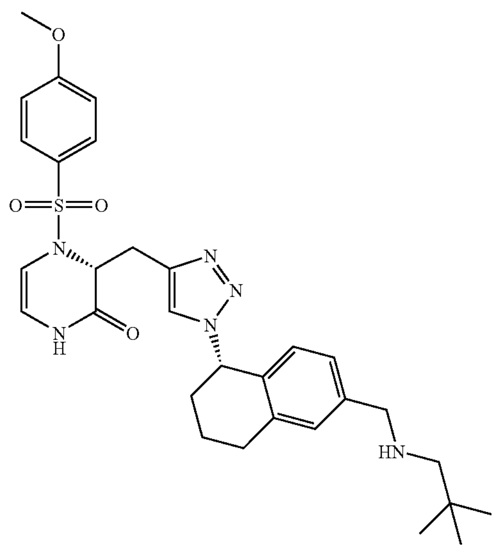 | $C_{30}H_{38}N_6O_4S$, Calcd: 578.27 Found: 579.3 (M + H) |
| 99 | (R)-3-((1-((R)-6-((4-methyl-piperazin-1-yl)methyl)-1,2,3,4-tetrahydronaphthalen-1-yl)-1H-1,2,3-triazol-4-yl)methyl)-4-tosyl-3,4-dihydropyrazin-2(1H)-one | 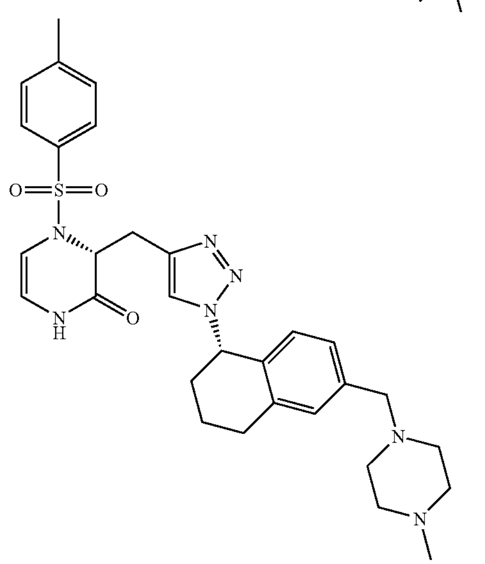 | $C_{30}H_{37}N_7O_3S$, Calcd: 575.27 Found: 576.3 (M + H) |

-continued

| No. | Name | Structure | Mass |
|---|---|---|---|
| 100 | (R)-3-((1-((R)-6-((4-methyl-piperazin-1-yl)methyl)-1,2,3,4-tetrahydronaphthalen-1-yl)-1H-1,2,3-triazol-4-yl)methyl)-4-(phenylsulfonyl)piperazin-2-one | 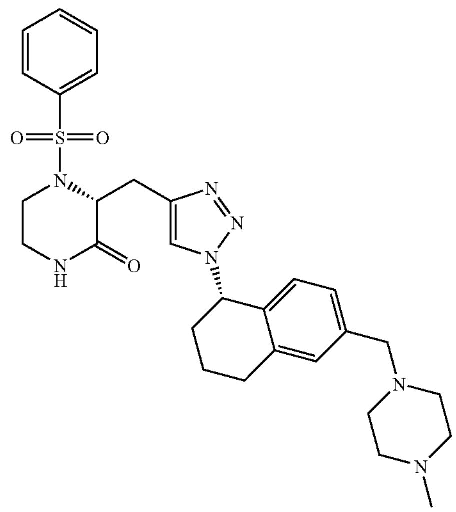 | $C_{29}H_{37}N_7O_3S$, Calcd: 563.27 Found: 564.2 (M + H) |
| 101 | (R)-3-((1-((R)-6-((4-methyl-piperazin-1-yl)methyl)-1,2,3,4-tetrahydronaphthalen-1-yl)-1H-1,2,3-triazol-4-yl)methyl)-4-(3-(trifluoromethyl)phenylsulfonyl)-3,4-dihydropyrazin-2(1H)-one | 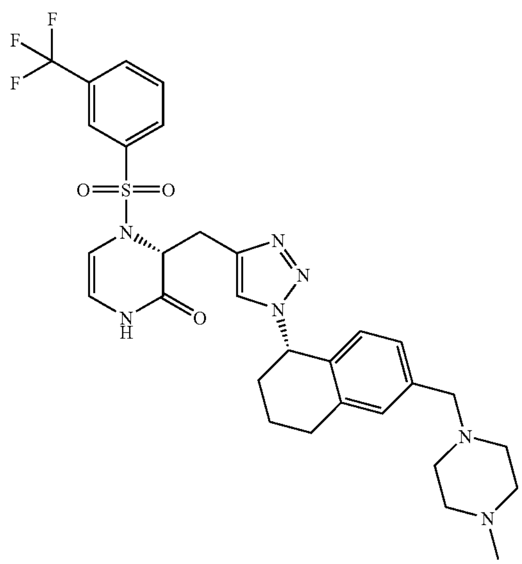 | $C_{30}H_{34}F_3N_7O_3S$, Calcd: 629.24 Found: 630.3 (M + H) |
| 102 | (R)-3-((1-((R)-6-((4-methyl-piperazin-1-yl)methyl)-1,2,3,4-tetrahydronaphthalen-1-yl)-1H-1,2,3-triazol-4-yl)methyl)-4-(phenylsulfonyl)-3,4-dihydropyrazin-2(1H)-one | 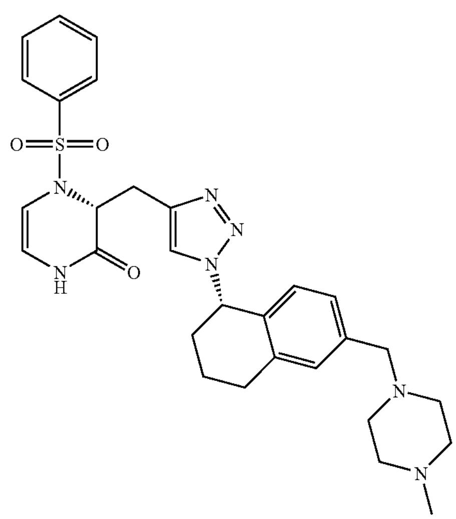 | $C_{29}H_{35}N_7O_3S$, Calcd: 561.25 Found: 562.2 (M + H) |

-continued

| No. | Name | Structure | Mass |
|---|---|---|---|
| 103 | (R)-4-(4-chlorophenyl-sulfonyl)-3-((1-((R)-6-((4-methylpiperazin-1-yl)methyl)-1,2,3,4-tetrahydro-naphthalen-1-yl)-1H-1,2,3-triazol-4-yl)methyl)piperazin-2-one | 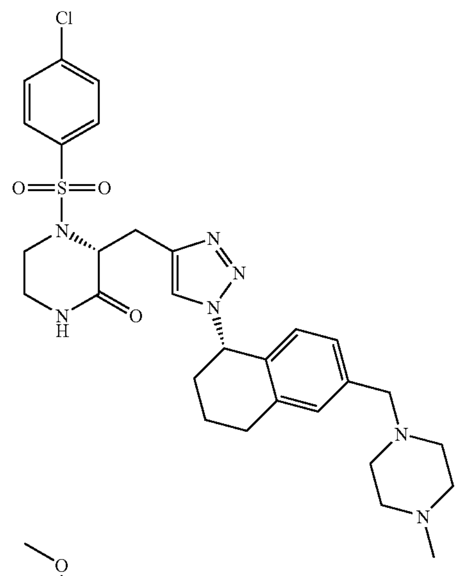 | $C_{29}H_{36}ClN_7O_3S$, Calcd: 597.23 Found: 598.2 (M + H) |
| 104 | (R)-4-(4-methoxyphenyl-sulfonyl)-3-((1-((R)-6-((4-methylpiperazin-1-yl)methyl)-1,2,3,4-tetrahydronaphthalen-1-yl)-1H-1,2,3-triazol-4-yl)methyl)-piperazin-2-one | 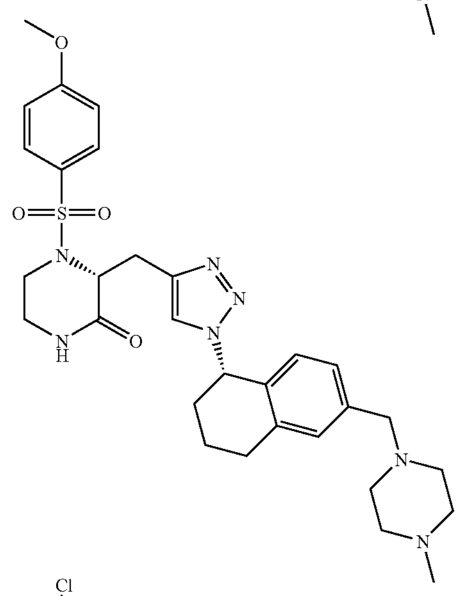 | $C_{30}H_{39}N_7O_4S$, Calcd: 593.28 Found: 594.2 (M + H) |
| 105 | (R)-4-(4-chlorophenyl-sulfonyl)-3-((1-((R)-6-((4-methylpiperazin-1-yl)methyl)-1,2,3,4-tetrahydro-naphthalen-1-yl)-1H-1,2,3-triazol-4-yl)methyl)-3,4-dihydropyrazin-2(1H)-one | 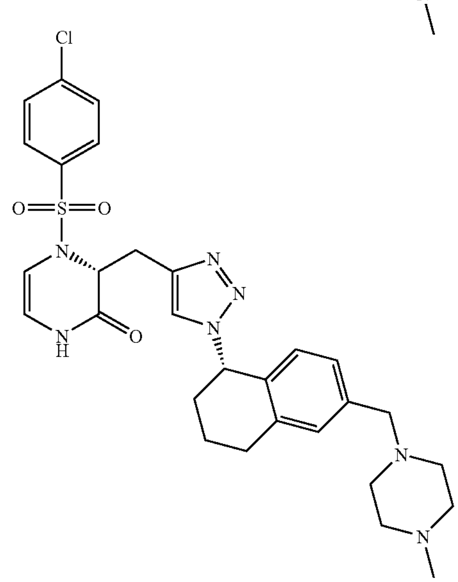 | $C_{29}H_{34}ClN_7O_3S$, Calcd: 595.21 Found: 596.1 (M + H) |

| No. | Name | Structure | Mass |
|-----|------|-----------|------|
| 106 | (R)-4-(4-methoxyphenyl-sulfonyl)-3-((1-((R)-6-((4-methylpiperazin-1-yl)methyl)-1,2,3,4-tetrahydronaphthalen-1-yl)-1H-1,2,3-triazol-4-yl)methyl)-3,4-dihydropyrazin-2(1H)-one | 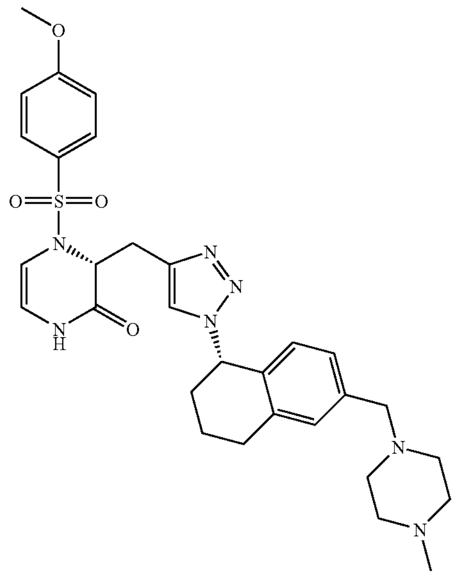 | C$_{30}$H$_{37}$N$_7$O$_4$S, Calcd: 591.26 Found: 592.2 (M + H) |
| 107 | (R)-3-((1-((R)-6-((isobutyl-amino)methyl)-1,2,3,4-tetrahydro-naphthalen-1-yl)-1H-1,2,3-triazol-4-yl)methyl)-4-tosyl-3,4-dihydropyrazin-2(1H)-one | 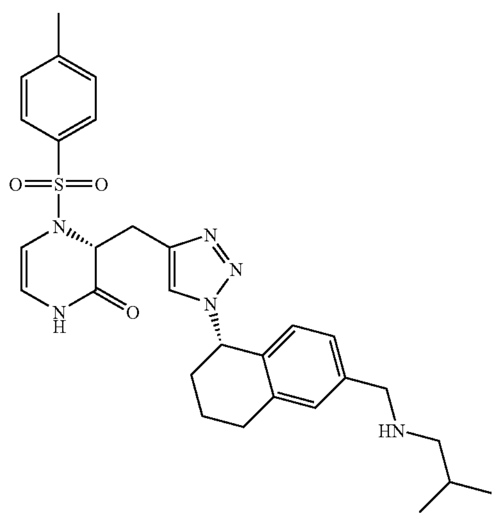 | C$_{29}$H$_{36}$N$_6$O$_3$S, Calcd: 548.26 Found: 549.3 (M + H) |
| 108 | (R)-3-((1-((R)-6-((isobutyl-amino)methyl)-1,2,3,4-tetra-hydronaphthalen-1-yl)-1H-1,2,3-triazol-4-yl)methyl)-4-(phenyl-sulfonyl)piperazin-2-one | 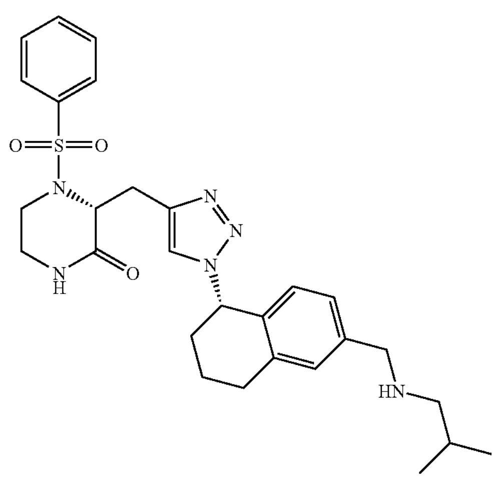 | C$_{28}$H$_{36}$N$_6$O$_3$S, Calcd: 536.26 Found: 537.3 (M + H) |

| No. | Name | Structure | Mass |
|---|---|---|---|
| 109 | (R)-3-((1-((R)-6-((isobutyl-amino)methyl)-1,2,3,4-tetra-hydronaphthalen-1-yl)-1H-1,2,3-triazol-4-yl)methyl)-4-(3-(trifluoromethyl)phenylsulfonyl)-3,4-dihydropyrazin-2(1H)-one | 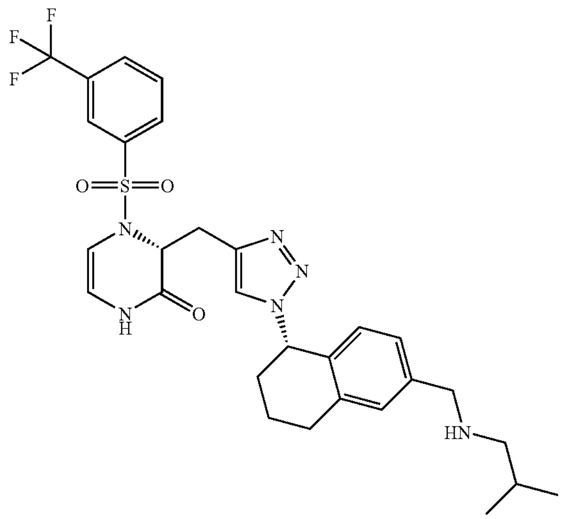 | $C_{29}H_{33}F_3N_6O_3S$, Calcd: 602.23 Found: 603.0 (M + H) |
| 110 | (R)-3-((1-((R)-6-((isobutyl-amino)methyl)-1,2,3,4-tetrahydro-naphthalen-1-yl)-1H-1,2,3-triazol-4-yl)methyl)-4-(phenylsulfonyl)-3,4-dihydropyrazin-2(1H)-one | 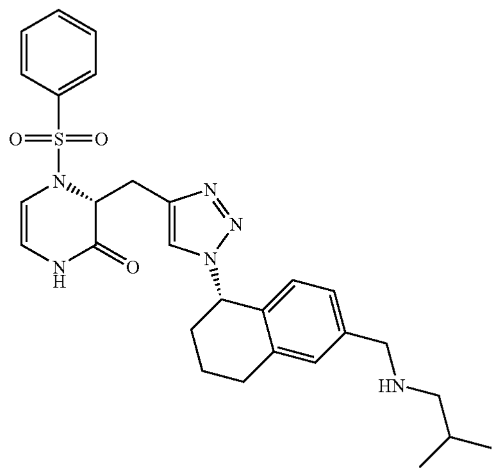 | $C_{28}H_{34}N_6O_3S$, Calcd: 534.24 Found: 535.2 (M + H) |
| 111 | (R)-4-(4-chlorophenyl-sulfonyl)-3-((1-((R)-6-((isobutylamino)-methyl)-1,2,3,4-tetrahydro-naphthalen-1-yl)-1H-1,2,3-triazol-4-yl)methyl)piperazin-2-one | 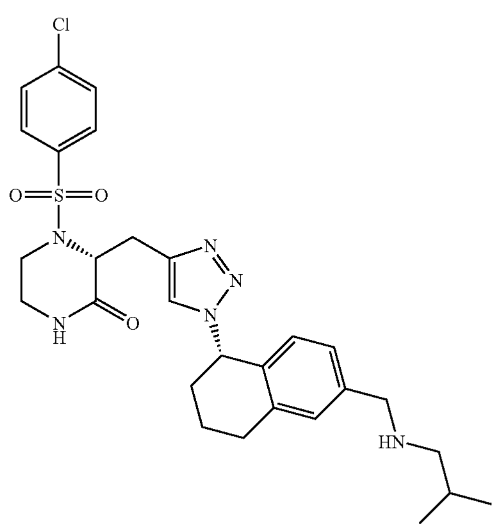 | $C_{28}H_{35}ClN_6O_3S$, Calcd: 570.22 Found: 571.2 (M + H) |

| No. | Name | Structure | Mass |
|---|---|---|---|
| 112 | (R)-3-((1-((R)-6-((isobutyl-amino)methyl)-1,2,3,4-tetrahydro-naphthalen-1-yl)-1H-1,2,3-triazol-4-yl)methyl)-4-(4-methoxy-phenylsulfonyl)piperazin-2-one | 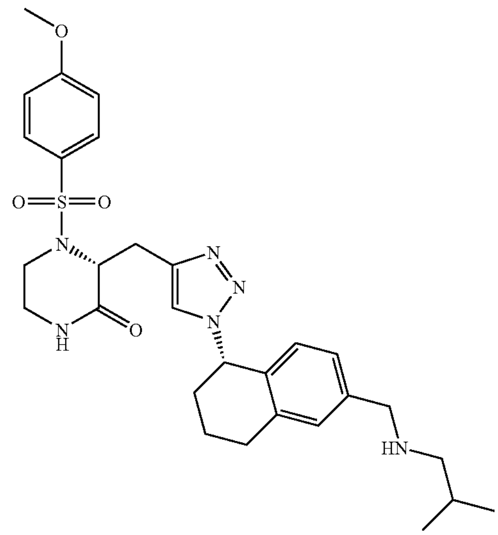 | $C_{29}H_{38}N_6O_4S$, Calcd: 566.27 Found: 567.3 (M + H) |
| 113 | (R)-4-(4-chlorophenyl-sulfonyl)-3-((1-((R)-6-((isobutylamino)-methyl)-1,2,3,4-tetrahydro-naphthalen-1-yl)-1H-1,2,3-triazol-4-yl)methyl)-3,4-dihydropyrazin-2(1H)-one | 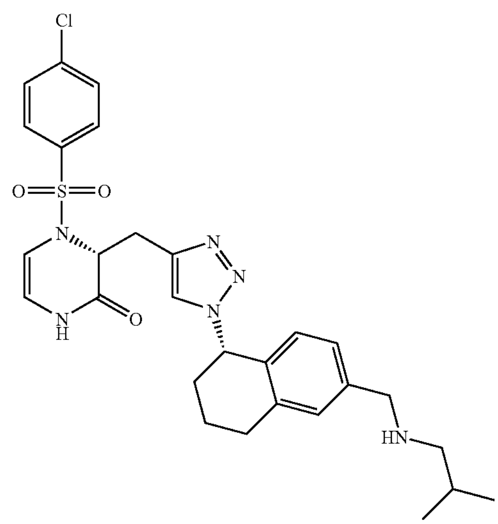 | $C_{28}H_{33}ClN_6O_3S$, Calcd: 568.2 Found: 569.1 (M + H) |
| 114 | (R)-3-((1-((R)-6-((isobutyl-amino)methyl)-1,2,3,4-tetra-hydronaphthalen-1-yl)-1H-1,2,3-triazol-4-yl)methyl)-4-(4-methoxyphenylsulfonyl)-3,4-dihydropyrazin-2(1H)-one | 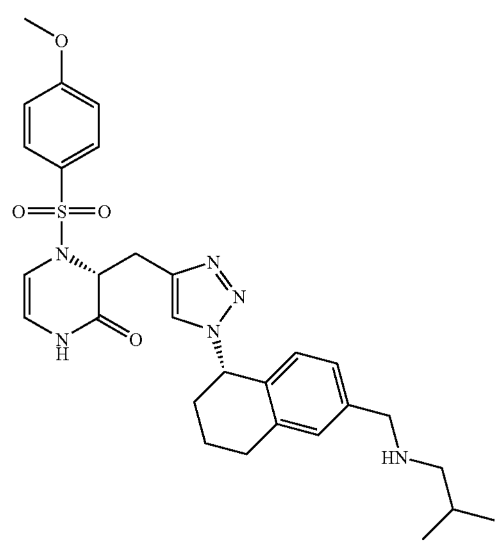 | $C_{29}H_{36}N_6O_4S$, Calcd: 564.25 Found: 565.2 (M + H) |

| No. | Name | Structure | Mass |
|---|---|---|---|
| 115 | (R)-3-((1-((R)-6-((4-fluoro-piperidin-1-yl)methyl)-1,2,3,4-tetrahydronaphthalen-1-yl)-1H-1,2,3-triazol-4-yl)methyl)-4-tosyl-3,4-dihydropyrazin-2(1H)-one | 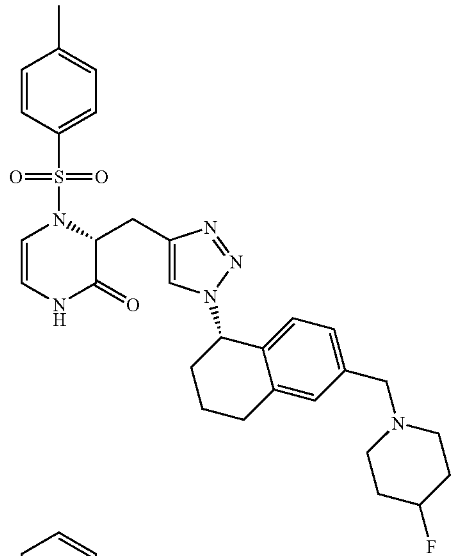 | $C_{30}H_{35}FN_6O_3S$, Calcd: 578.25 Found: 579.0 (M + H) |
| 116 | (R)-3-((1-((R)-6-((4-fluoro-piperidin-1-yl)methyl)-1,2,3,4-tetrahydronaphthalen-1-yl)-1H-1,2,3-triazol-4-yl)methyl)-4-(phenylsulfonyl)piperazin-2-one | 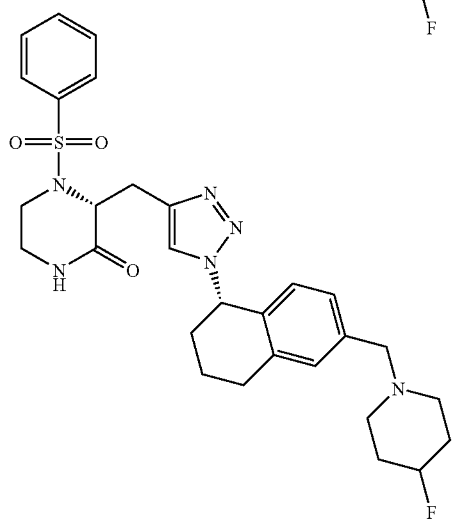 | $C_{29}H_{35}FN_6O_3S$, Calcd: 566.25 Found: 567.3 (M + H) |
| 117 | (R)-3-((1-((R)-6-((4-fluoro-piperidin-1-yl)methyl)-1,2,3,4-tetrahydronaphthalen-1-yl)-1H-1,2,3-triazol-4-yl)methyl)-4-(3-(trifluoro-methyl)phenylsulfonyl)-3,4-dihydropyrazin-2(1H)-one | 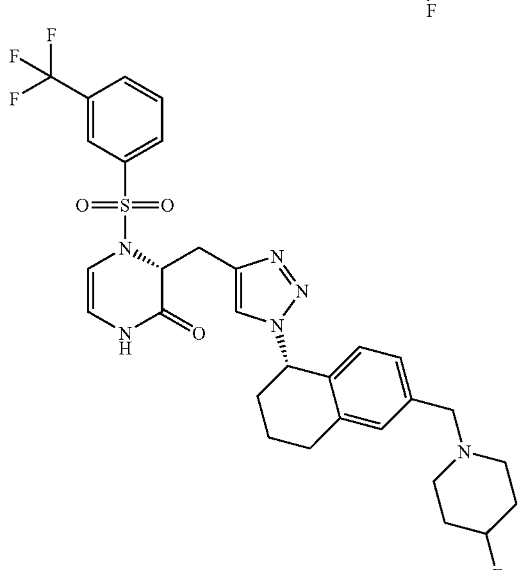 | $C_{30}H_{32}F_4N_6O_3S$, Calcd: 632.22 Found: 633.0 (M + H) |

Example 5

Synthesis of (R)-3-((1-(4-(4,5-dihydro-1H-imidazol-2-yl)phenethyl)-1H-1,2,3-triazol-4-yl)methyl)-4-tosylpiperazin-2-one

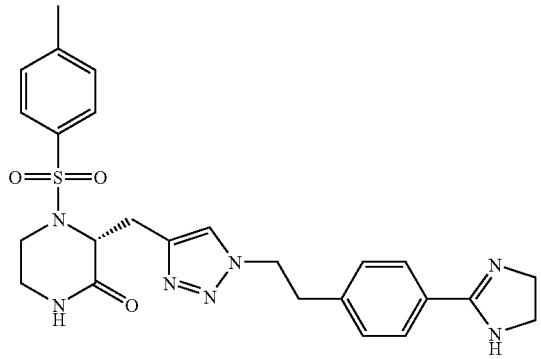

Step (i): Synthesis of (R)-4-(2-(4-((3-oxo-1-tosylpiperazin-2-yl)methyl)-1H-1,2,3-triazol-1-yl)ethyl)benzonitrile To a solution of (R)-3-(prop-2-ynyl)-4-tosylpiperazin-2-one (292 mg, 1 mmol) and 4-(2-azidoethyl)benzonitrile (172 mg, 1 mmol) in dioxane (3 mL) and t-BuOH (4 mL) was added a solution of copper(2+) sulfate, pentahydrate (249 mg, 1 mmol) in 0.5 mL of water, followed with a solution of (+)-sodium 1-ascorbate (198 mg, 1 mmol) in 0.5 mL of water. The resulting solution was stirred at room temperature for 2 h. The reaction was diluted with EtOAc, washed with brine, dried over $Na_2SO_4$, and evaporated to dryness. Flash chromatography ($SiO_2$, EtOAc to EtOAc/MeOH=100:10 to 100:15) afforded the title compound as a white solid.

Step (ii): Synthesis of (R)-3-((1-(4-(4,5-dihydro-1H-imidazol-2-yl)phenethyl)-1H-1,2,3-triazol-4-yl)methyl)-4-tosylpiperazin-2-one (R)-4-(2-(4-((3-oxo-1-tosylpiperazin-2-yl)methyl)-1H-1,2,3-triazol-1-yl)ethyl)benzonitrile (135 mg) was azeotroped with benzene and was dissolved in anhydrous EtOH (10 mL).

To this solution dry HCl was bubbled through for 60 min at 0° C. The solvent was evaporated to dryness under high vacuum to give a yellow solid. This yellow solid was dissolved in dry EtOH (10 mL) and ethylene diamine (0.4 mL) was added and the resulting solution was stirred at RT overnight. The solvent was evaporated to dryness under high vacuum. Flash chromatography ($SiO_2$, EtOAc/2M $NH_3$ in MeOH=100:15 to 100:30) afforded the title compound as a white solid.

Example 6

Synthesis of (R)-4-(3,4-dichlorophenylsulfonyl)-3-((1-((R)-3-isobutyl-1,2,3,4,7,8,9,10-octahydrobenzo[f]isoquinolin-7-yl)-1H-1,2,3-triazol-4-yl)methyl)-3,4-dihydropyrazin-2(1H)-one

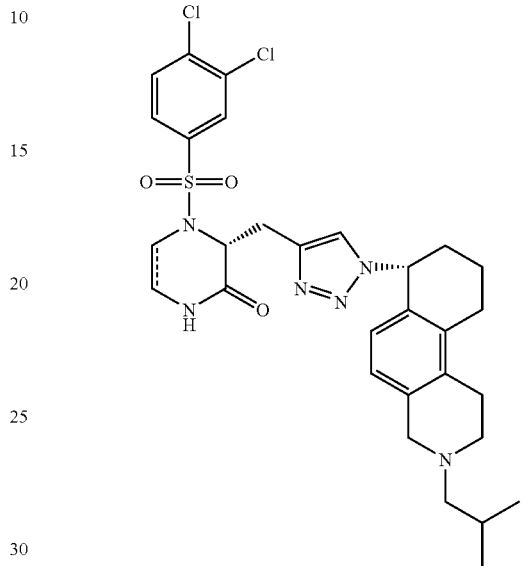

Step (i): Synthesis of (R)-4-(3,4-dichlorophenylsulfonyl)-3-((1-((R)-3-(2,2,2-trifluoroacetyl)-1,2,3,4,7,8,9,10-octahydrobenzo[f]isoquinolin-7-yl)-1H-1,2,3-triazol-4-yl)methyl)-3,4-dihydropyrazin-2(1H)-one To a solution of (R)-4-(3,4-dichlorophenylsulfonyl)-3-(prop-2-ynyl)-3,4-dihydropyrazin-2(1H)-one (345 mg, 1 mmol) and (R)-1-(7-azido-1,2,7,8,9,10-hexahydrobenzo[f]isoquinolin-3(4H)-yl)-2,2,2-trifluoroethanone (324 mg, 1 mmol) in dioxane (3 mL) and t-BuOH (4 mL) was added a solution of copper(2+) sulfate, pentahydrate (249 mg, 1 mmol) in water (0.5 mL), followed by a solution of (+)-sodium 1-ascorbate (198 mg, 1 mmol) in water (0.5 mL). The resulting solution was stirred at room temperature for 16 h. The reaction was diluted with EtOAc, washed with brine, dried over $Na_2SO4$, and evaporated to dryness. Flash chromatography ($SiO_2$, EtOAc/hexane=2:1 to pure EtOAc) afforded the title compound as a white solid.

Step (ii): Synthesis of (R)-4-(3,4-dichlorophenylsulfonyl)-3-((1-((R)-1,2,3,4,7,8,9,10-octahydrobenzo[t]isoquinolin-7-yl)-1H-1,2,3-triazol-4-yl)methyl)-3,4-dihydropyrazin-2(1H)-one To a solution of (R)-4-(3,4-dichlorophenylsulfonyl)-3-((1-((R)-3-(2,2,2-trifluoroacetyl)-1,2,3,4,7,8,9,10-octahydrobenzo[f]isoquinolin-7-yl)-1H-1,2,3-triazol-4-yl)methyl)-3,4-dihydropyrazin-2(1H)-one (540 mg, 0.807 mmol) in a mixture of solvents (THF/MeOH/H2O=3:3:1, 7 mL) was added $K_2CO_3$ (223 mg, 1.62 mmol). After stirring at RT for 2 h, the solvent was evaporated to dryness and the residue was submitted to flash chromatography ($SiO_2$, EtOAc/2M $NH_3$ in MeOH=100:15 to 100:20 to 100:25 to 100:30) to give the title compound as a white solid.

Step (iii): Synthesis of (R)-4-(3,4-dichlorophenylsul-
fonyl)-3-((1-((R)-3-isobutyl-1,2,3,4,7,8,9,10-octahy-
drobenzo[f]isoquinolin-7-yl)-1H-1,2,3-triazol-4-yl)
methyl)-3,4-dihydropyrazin-2(1H)-one To a solution of ((R)-4-(3,4-dichlorophenylsulfonyl)-3-
((1-((R)-1,2,3,4,7,8,9,10-octahydrobenzo[f]isoquinolin-7-
yl)-1H-1,2,3-triazol-4-yl)methyl)-3,4-dihydropyrazin-2
(1H)-one (220 mg, 0.384 mmol) and isobutyraldehyde (83
mg, 1.15 mmol) in 3 mL of 1,2-dichloroethane was added
sodium triacetoxyborohydride (163 mg, 0.768 mmol) and the
resulting solution was stirred at RT overnight. The reaction
mixture was quenched with sat. $NaHCO_3$, extracted with
EtOAc, dried over Na2SO4, filtered and evaporated to dry-
ness. Flash chromatography ($SiO_2$, EtOAc to EtOAc/
MeOH=100:7 to 100:12 to 100:14) afforded the title com-
pound as a white solid.

Example 7

Synthesis of (R)-4-(3,4-dichlorophenylsulfonyl)-3-
((1-((R)-2-isobutyl-1,2,3,4,6,7,8,9-octahydrobenzo
[g]isoquinolin-6-yl)-1H-1,2,3-triazol-4-yl)methyl)-3,
4-dihydropyrazin-2(1H)-one

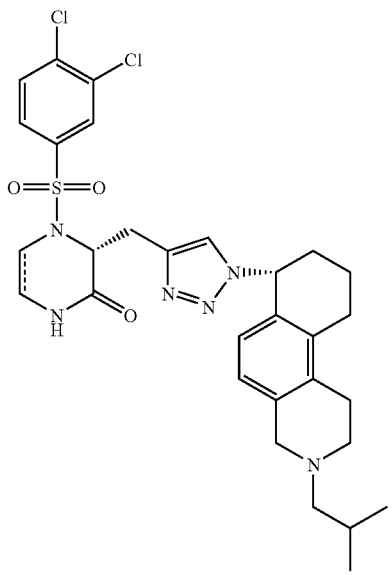

Step (i): Synthesis of (R)-4-(3,4-dichlorophenylsul-
fonyl)-3-((1-((R)-2-(2,2,2-trifluoroacetyl)-1,2,3,4,6,
7,8,9-octahydrobenzo[g]isoquinolin-6-yl)-1H-1,2,3-
triazol-4-yl)methyl)-3,4-dihydropyrazin-2(1H)-one To a solution of (R)-4-(3,4-dichlorophenylsulfonyl)-3-
(prop-2-ynyl)-3,4-dihydropyrazin-2(1H)-one (345 mg, 1
mmol) and (R)-1-(6-azido-3,4,6,7,8,9-hexahydrobenzo[g]
isoquinolin-2(1H)-yl)-2,2,2-trifluoroethanone (324 mg, 1
mmol) in dioxane (3 mL) and t-BuOH (4 mL) was added a
solution of copper(2+) sulfate, pentahydrate (249 mg, 1
mmol) in water (0.5 mL), followed by a solution of (+)-
sodium l-ascorbate (198 mg, 1 mmol) in water (0.5 mL). The
resulting solution was stirred at room temperature for 16.

The reaction was diluted with EtOAc, washed with brine,
dried over $Na_2SO_4$, and evaporated to dryness. Flash chro-
matography ($SiO_2$, EtOAc/hexane=2:1 to pure EtOAc)
afforded the title compound as a white solid.

Step (ii): Synthesis of (R)-4-(3,4-dichlorophenylsul-
fonyl)-3-((1-((R)-1,2,3,4,6,7,8,9-octahydrobenzo[g]
isoquinolin-6-yl)-1H-12,3-triazol-4-yl)methyl)-3,4-
dihydropyrazin-2(1H)-one To a solution of (R)-4-(3,4-dichlorophenylsulfonyl)-3-((1-
((R)-2-(2,2,2-trifluoroacetyl)-1,2,3,4,6,7,8,9-octahy-
drobenzo[g]isoquinolin-6-yl)-1H-1,2,3-triazol-4-yl)me-
thyl)-3,4-dihydropyrazin-2(1H)-one (450 mg, 0.673 mmol)
in a mixture of solvents (THF/MeOH/$H_2O$=3:3:1, 7 mL)) was
added $K_2CO_3$ (186 mg, 1.345 mmol). After stirring at RT for
2 hs, the solvent was evaporated to dryness and the residue
was submitted to flash chromatography ($SiO_2$, EtOAc/2M
$NH_3$ in MeOH=100:15 to 100:20 to 100:25 to 100:30) to give
the title compound as a white solid.

Step (iii): Synthesis of (R)-4-(3,4-dichlorophenylsul-
fonyl)-3-((1-((R)-2-isobutyl-1,2,3,4,6,7,8,9-octahy-
drobenzo[g]isoquinolin-6-yl)-1H-1,2,3-triazol-4-yl)
methyl)-3,4-dihydropyrazin-2(1H)-one To a solution of (R)-4-(3,4-dichlorophenylsulfonyl)-3-((1-
((R)-1,2,3,4,6,7,8,9-octahydrobenzo[g]isoquinolin-6-yl)-
1H-1,2,3-triazol-4-yl)methyl)-3,4-dihydropyrazin-2(1H)-
one (160 mg, 0.28 mmol) and isobutryaldehyde (60 mg, 0.84
mmol) in 3 mL of 1,2-dichloroethane was added Sodium
triacetoxyborohydride (119 mg, 0.56 mmol) and the resulting
solution was stirred at RT overnight. The reaction mixture
was quenched with sat. $NaHCO_3$, extracted with EtOAc,
dried over $Na_2SO_4$, filtered and evaporated to dryness. Flash
chromatography ($SiO_2$, EtOAc to EtOAc/MeOH=100:7 to
100:12 to 100:14) afforded the title compound) as a white
solid.

Example 8

Synthesis of (R)-2-((1-((R)-6-(piperidin-1-ylmethyl)-
1,2,3,4-tetrahydronaphthalen-1-yl)-1H-1,2,3-triazol-
4-yl)methyl)-1-tosyl-1,2-dihydropyrido[2,3-]
pyrazin-3(4H)-one

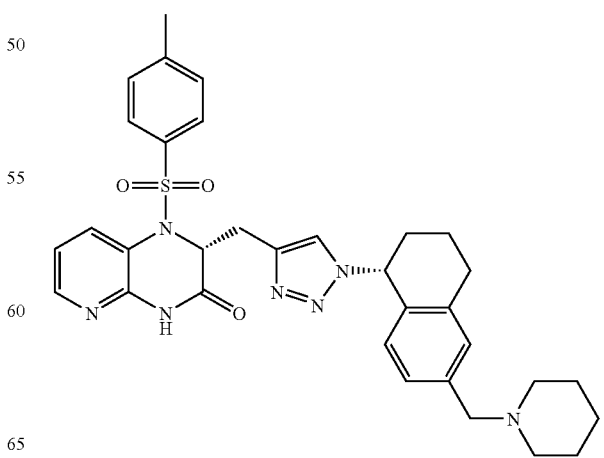

Step (i): Synthesis of 3-fluoro-2-nitropyridine

A solution of sodium nitrite (20 g, 288 mmol) in water (40 mL) was added dropwise to a stirred mixture of 2-nitropyridine-3-amine (40 g, 288 mmol) in 34% fluoroboric acid (140 mL). During addition the temperature was maintained between −8 C to −2° C. After 0.5 h, the suspension was filtered and the solid washed with 34% fluoroboric acid (35 mL), ether (80 mL) and dried at room temperature under high vacuum for 12 h to give 52 g of an orange brown solid of the fluoroborate salt. The dry solid was decomposed by heating to 120° C. After decomposition the remaining oil was treated with a solution of 10% sodium hydrogenocarbonate (80 mL) and the mixture was extracted with dichloromethane. The combined extracts were dried over sodium sulfate, filtered and the solvent removed over under reduced pressure to yield the title compound as a pale yellow solid.

Step (ii): Synthesis of (R)-methyl 2-(2-nitropyridin-3-ylamino)pent-4-ynoate To a mixture of 3-fluoro-2-nitropyridine (860 mg, 6.05 mmol) and (R)-methyl 2-aminopent-4-ynoate (1.924 g, 15.131 mmol) in DMF was added triethylamine (2.55 ml, 18.16 mmol) and the resulting solution was stirred over the weekend. The reaction mixture was quenched with sat. NaHCO$_3$, extracted with EtOAc/hexane=2:1, washed with brine, dried over Na$_2$SO$_4$ and the solvent was evaporated. Flash chromatography (SiO$_2$, DCM to DCM/EtOAc=3:1 to 2:1) afforded the title compound as a pale yellow solid.

Step (iii): Synthesis of (R)-2-(prop-2-ynyl)-1,2-dihydropyrido[2,3-b]pyrazin-3(4H)-one A suspension of (R)-methyl 2-(2-nitropyridin-3-ylamino) pent-4-ynoate (220 mg, 0.883 mmol), iron (296 mg, 5.30 mmol) and NH$_4$Cl in 10 mL of MeOH was heated to reflux for 4 h. After cooling to room temperature, 0.5 mL of NEt$_3$ was added and the solution was stirred overnight. The solvent was evaporated and the residue was redissolved with EtOAc and filtered through a pad of silica gel. The filtrate was evaporated to dryness the title compound that was used directly in the next step.

Step (iv): Synthesis of (R)-2-(prop-2-ynyl)-1-tosyl-1,2-dihydropyrido[2,3-b]pyrazin-3(4H)-one A solution of (R)-2-(prop-2-ynyl)-1,2-dihydropyrido[2,3-b]pyrazin-3(4H)-one (150 mg, 0.8 mmol) (300 mg of crude from last step) and 4-methylbenzene-1-sulfonyl chloride (229 mg, 1.20 mmol) in pyridine (3 mL) was stirred at room temperature for 3 h. The reaction mixture was treated with 10 % HCl (5 mL) and extracted with ethyl acetate, dried over Na$_2$SO$_4$ and evaporated. Flash chromatography (SiO$_2$, DCM to DCM/ethyl acetate=4:1 to 3:1 to 2:1 to 1:1) gave the title compound as a white solid.

Step (v): Synthesis of (R)-2-((1-((R)-6-(piperidin-1-ylmethyl)-1,2,3,4-tetrahydro-naphthalen-1-yl)-1H-1,2,3-triazol-4-yl)methyl)-1-tosyl-1,2-dihydropyrido[2,3-b]pyrazin-3(4H)-one To a solution of (R)-2-(prop-2-ynyl)-1-tosyl-1,2-dihydropyrido[2,3-b]pyrazin-3(4H)-one (210 mg, 0.615 mmol) and (R)-1-((5-azido-5,6,7,8-tetrahydronaphthalen-2-yl)methyl) piperidine (183 mg, 0.677 mmol) in dioxane (3 mL) and t-BuOH (4 mL) was added a solution of copper(2+) sulfate, pentahydrate (43.0 µl, 0.615 mmol) in water (1 mL), followed by a solution of (+)-sodium 1-ascorbate (122 mg, 615 µmol). The resulting solution was stirred at room temperature overnight. The reaction was diluted with EtOAc, washed with brine, dried over Na$_2$SO$_4$, and evaporated to dryness. Flash chromatography (SiO$_2$, EtOAc to EtOAc/2M NH3 in MeOH=100:5 to 100:10 to 100:15) of the residue afforded the title compound as a white solid.

Proceeding as described above, but substituting 2-fluoronitrobenzene for 3-fluoro-2-nitropyridine the following compounds of Formula (I) can be prepared.

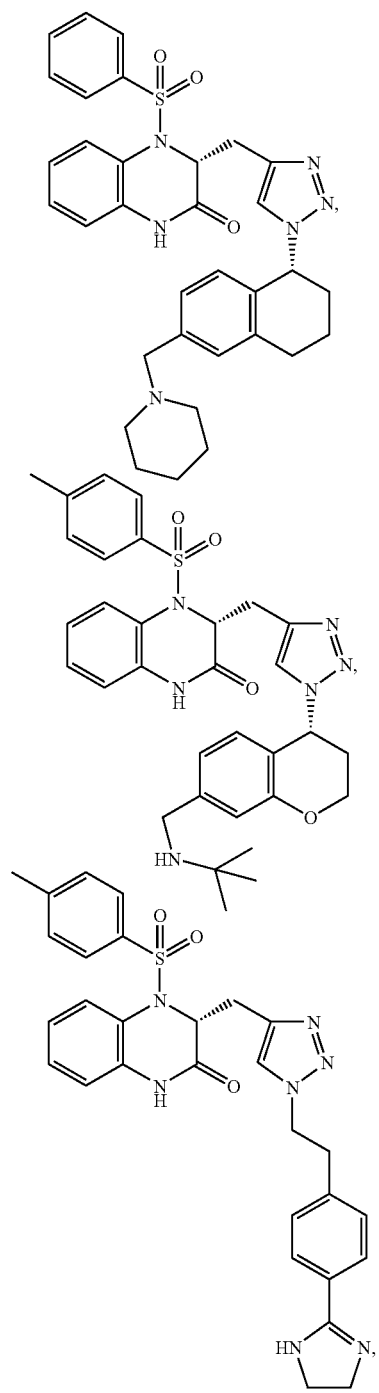

97
-continued
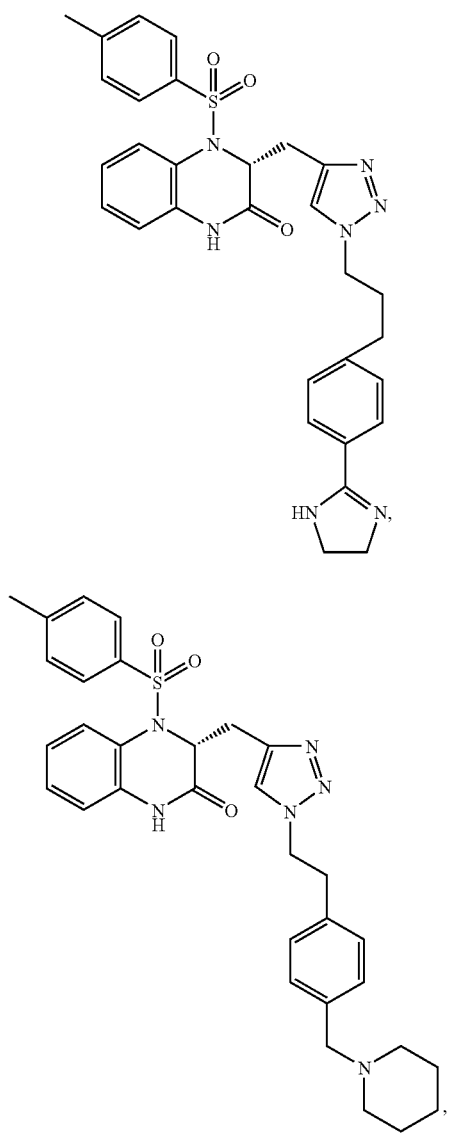
98
-continued
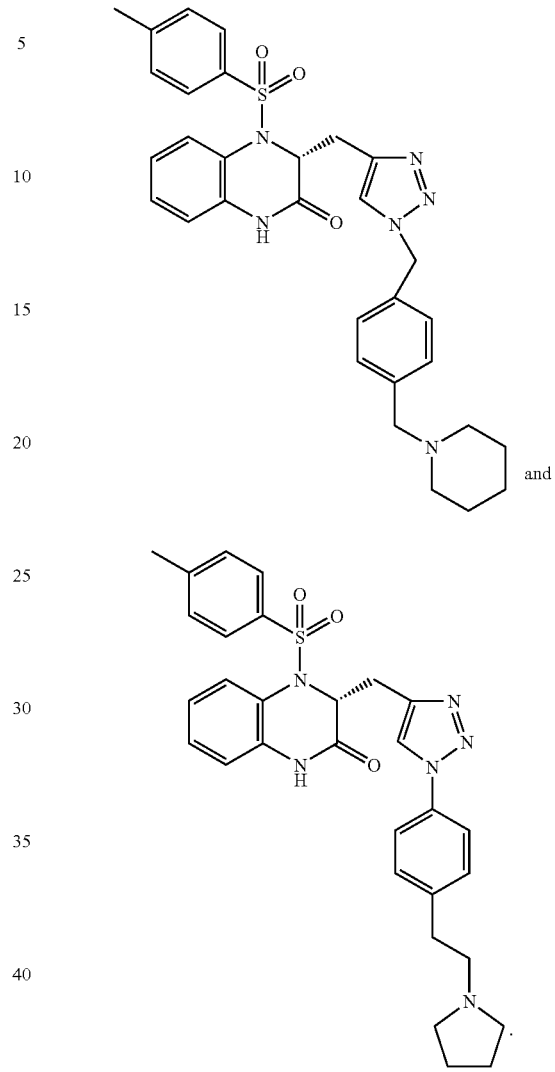
and
Following the procedures described above, the following compounds were prepared:
| Compound Name | Structure | MS data (M + 1) |
| --- | --- | --- |
| (R)-3-((1-((R)-6-bromo-2,2'-spiro-cyclopentylchroman-4-yl)-1H-1,2,3-triazol-4-yl)methyl)-4-(3,4-dichloro-phenylsulfonyl)-3,4-dihydropyrazin-2(1H)-one | 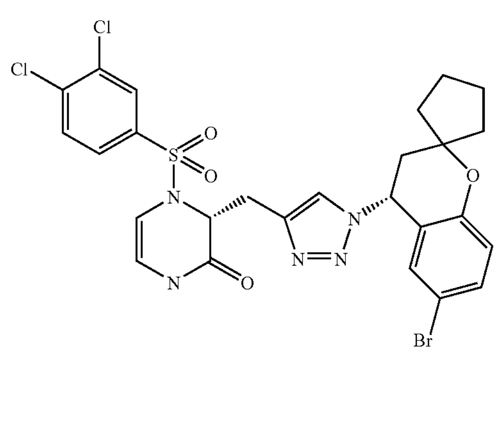 | |

-continued

| Compound Name | Structure | MS data (M + 1) |
|---|---|---|
| (R)-3-((1-((R)-6-chloro-1,1-dioxothiochroman-4-yl)-1H-1,2,3-triazol-4-yl)methyl)-4-(3,4-dichlorophenylsulfonyl)-3,4-dihydropyrazin-2(1H)-one | | Calcd. 602.905<br>Found: 603.9 |
| (R)-4-(3,4-dichlorophenyl-sulfonyl)-3-((1-((R)-1,2,3,4,7,8,9,10-octahydro-benzo[f]isoquinolin-7-yl)-1H-1,2,3-pyrazin-2(1H)-one | 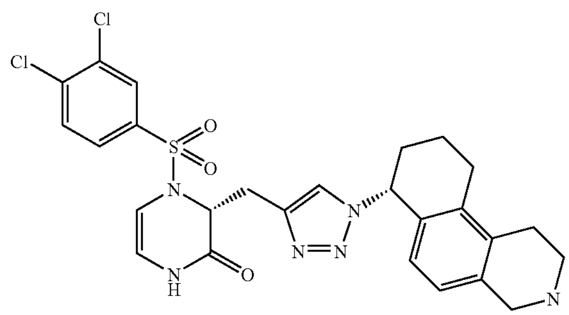 | Calcd. 573.502<br>Found: 573.1 |
| (R)-4-(3,4-dichlorophenyl-sulfonyl)-3-((1-((R)-1,2,3,4,6,7,8,9-octahydro-benzo[g]isoquinolin-6-yl)-1H-1,2,3-triazol-4-yl)methyl)-3,4-dihydro-pyrazin-2(1H)-one | 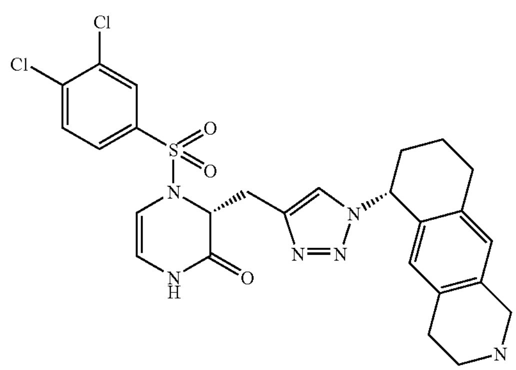 | Calcd. 573.502<br>Found: 573.1 |
| (R)-4-(3,4-dichlorophenylsulfonyl)-3-((1-((S)-2-(2-hydroxyethyl)-5,6,7,8-tetrahydroquinazolin-5-yl)-1H-1,2,3-triazol-4-yl)methyl)-3,4-dihydro-pyrazin-2(1H)-one | 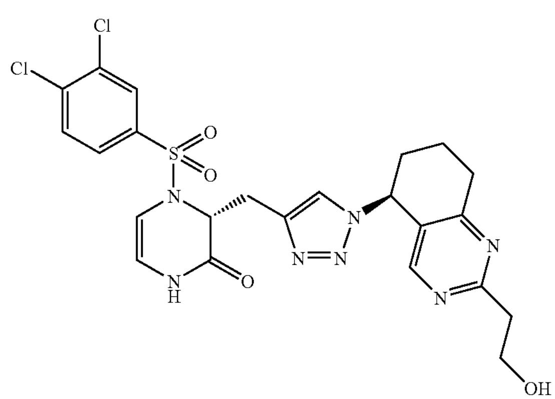 | |

-continued

| Compound Name | Structure | MS data (M + 1) |
|---|---|---|
| (R)-4-(3,4-dichlorophenylsulfonyl)-3-((1-((R)-2-(2-hydroxyethyl)-5,6,7,8-tetrahydroquinazolin-5-yl)-1H-1,2,3-triazol-4-yl)methyl)-3,4-dihydropyrazin-2(1H)-one | | |
| (R)-4-(3,4-dichlorophenyl-sulfonyl)-3-((1-((R)-3-isobutyl-1,2,3,4,7,8,9,10-octahydro-benzo[f]isoquinolin-7-yl)-1H-1,2,3-triazol-4-yl)methyl)-3,4-dihydropyrazin-2(1H)-one | | Calcd. 629.61<br>Found: 629.1 |
| (S)-4-(3,4-dichlorophenyl-sulfonyl)-3-((1-((S)-2-(piperidin-1-yl)ethyl)-5,6,7,8-tetrahydroquinazolin-5-yl)-1H-1,2,3-triazol-4-yl)methyl)-3,4-dihydropyrazin-2(1H)-one | | Calcd. 631.585<br>Found: 631.1 |

| Compound Name | Structure | MS data (M + 1) |
|---|---|---|
| (R)-4-(3,4-dichlorophenyl-sulfonyl)-3-((1-((S)-2-(2-(piperidin-1-yl)ethyl)-5,6,7,8-tetrahydroquinazolin-5-yl)-1H-1,2,3-triazol-4-yl)methyl)-3,4-dihydropyrazin-2(1H)-one | 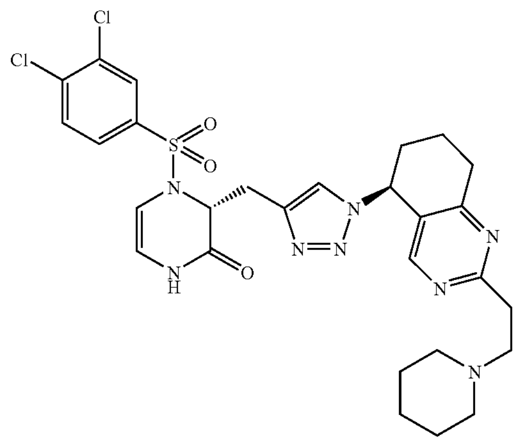 | Calcd. 631.585<br>Found: 631.1 |
| (R)-4-(3,4-dichlorophenyl-sulfonyl)-3-((1-((R)-2-(2-(piperidin-1-yl)ethyl)-5,6,7,8-tetrahydroquinazolin-5-yl)-1H-1,2,3-triazol-4-yl)methyl)-3,4-dihydropyrazin-2(1H)-one | 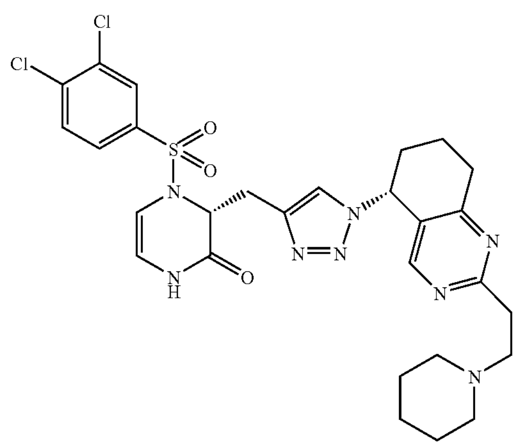 | Calcd. 631.585<br>Found: 631.1 |
| (S)-4-(3,4-dichlorophenyl-sulfonyl)-3-((1-((R)-2-(2-(piperidin-1-yl)ethyl)-5,6,7,8-tetrahydroquinazolin-5-yl)-1H-1,2,3-triazol-4-yl)methyl)-3,4-dihydropyrazin-2(1H)-one | 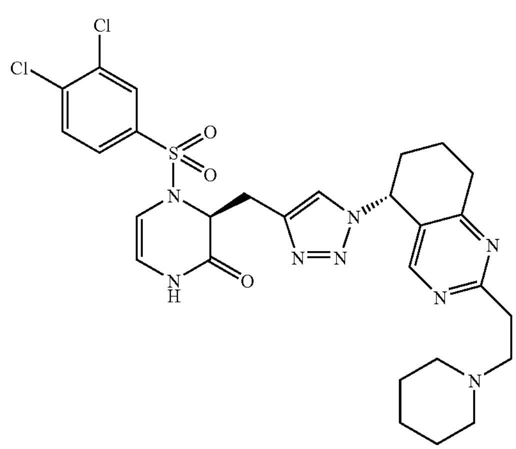 | Calcd. 631.585<br>Found: 631.1 |

-continued

| Compound Name | Structure | MS data (M + 1) |
| --- | --- | --- |
| (R)-methyl 5-(4-(((R)-3-oxo-1-tosylpiperazin-2-yl)methyl)-1H-1,2,3-triazol-1-yl)-5,6,7,8-tetrahydro-naphthalene-2-carboxylate | 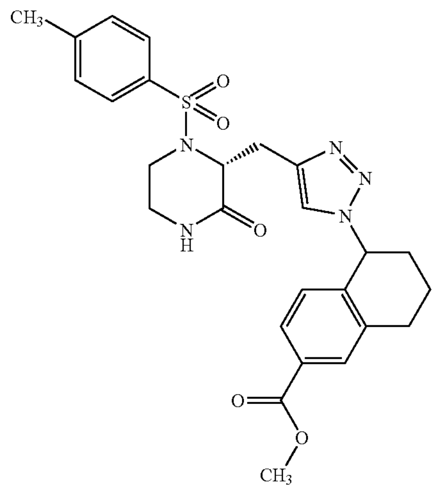 | Calcd. 523.611<br>Found: 524.2 |
| (S)-4-(3,4-dichlorophenyl-sulfonyl)-3-((1-((S)-2-(2-(4-methylpiperidin-1-yl)ethyl)-5,6,7,8-tetrahydroquinazolin-5-yl)-1H-1,2,3-triazol-4-yl)methyl)-3,4-dihydropyrazin-2(1H)-one | 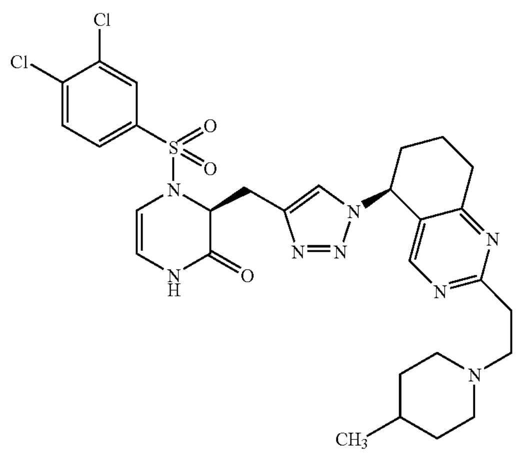 | Calcd. 645.61<br>Found: 645.1 |
| (R)-4-(3,4-dichlorophenyl-sulfonyl)-3-((1-((S)-2-(2-(4-methylpiperidin-1-yl)ethyl)-5,6,7,8-tetrahydroquinazolin-5-yl)-1H-1,2,3-triazol-4-yl)methyl)-3,4-dihydropyrazin-2(1H)-one | 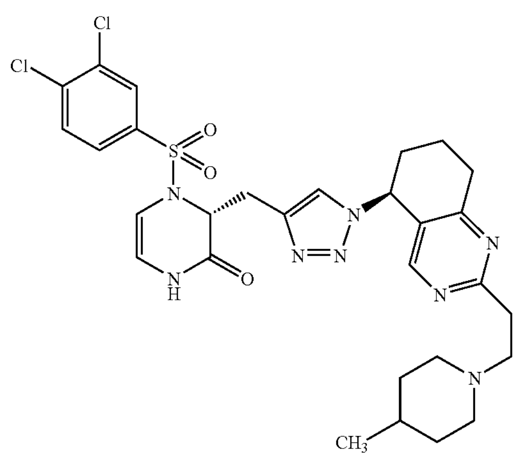 | Calcd. 645.61<br>Found: 645.1 |

| Compound Name | Structure | MS data (M + 1) |
| --- | --- | --- |
| (S)-4-(3,4-dichlorophenyl-sulfonyl)-3-((1-((R)-2-(2-(4-methylpiperidin-1-yl)ethyl)-5,6,7,8-tetrahydroquinazolin-5-yl)-1H-1,2,3-triazol-4-yl)-methyl)-3,4-dihydropyrazin-2(1H)-one | 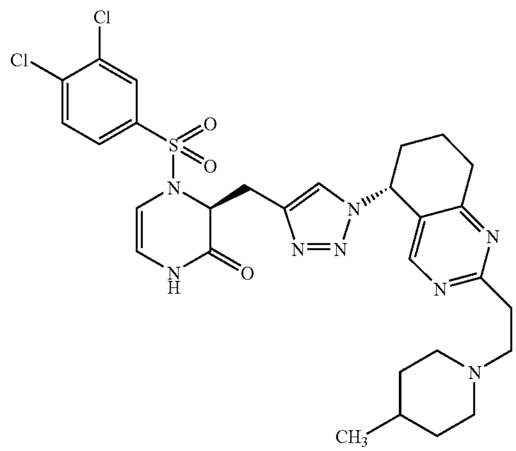 | Calcd. 645.61<br>Found: 645.1 |
| (R)-4-(3,4-dichlorophenyl-sulfonyl)-3-((1-((R)-2-(2-(4-methylpiperidin-1-yl)ethyl)-5,6,7,8-tetrahydroquinazolin-5-yl)-1H-1,2,3-triazol-4-yl)-methyl)-3,4-dihydropyrazin-2(1H)-one | 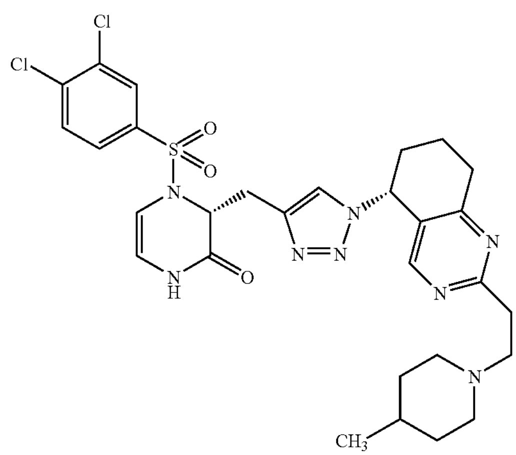 | Calcd. 645.61<br>Found: 645.1 |
| (R)-3-((1-((R)-6-(hydroxymethyl)-1,2,3,4-tetrahydronaphthalen-1-yl)-1H-1,2,3-triazol-4-yl)methyl)-4-tosyl-3,4-dihydropyrazin-2(1H)-one | 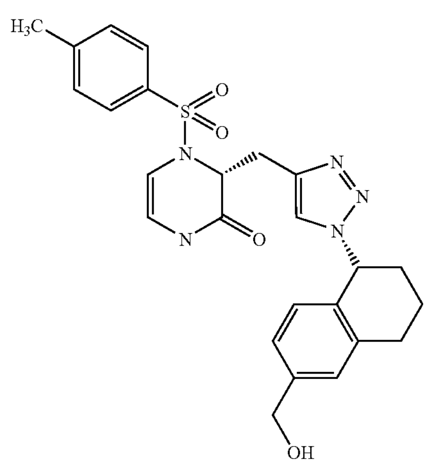 | |

| Compound Name | Structure | MS data (M + 1) |
| --- | --- | --- |
| (R)-3-((1-((R)-6-(((S)-2-(hydroxymethyl)pyrrolidin-1-yl)methyl)-1,2,3,4-tetrahydronaphthalen-1-yl)-1H-1,2,3-triazol-4-yl)methyl)-4-tosyl-3,4-dihydropyrazin-2(1H)-one | 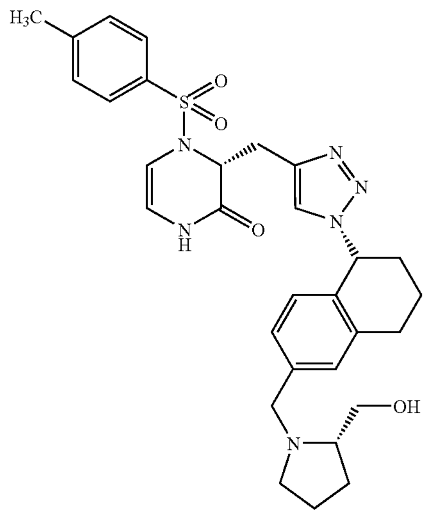 | Calcd. 576.718<br>Found: 577.2 |
| (R)-3-((1-((R)-6-(((R)-2-(hydroxymethyl)pyrrolidin-1-yl)methyl)-1,2,3,4-tetrahydro-naphthalen-1-yl)-1H-1,2,3-triazol-4-yl)methyl)-4-tosyl-3,4-dihydropyrazin-2(1H)-one | 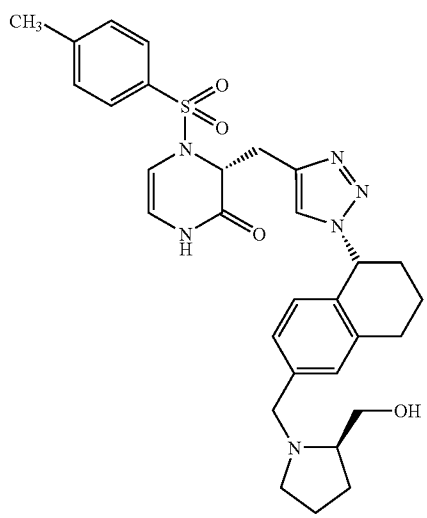 | Calcd. 576.718<br>Found: 577.2 |
| (R)-3-((1-((R)-6-(piperidin-1-yl-methyl)-1,2,3,4-tetrahydro-naphthalen-1-yl)-1H-1,2,3-triazol-4-yl)methyl)-4-tosyl-3,4-dihydropyrazin-2(1H)-one | 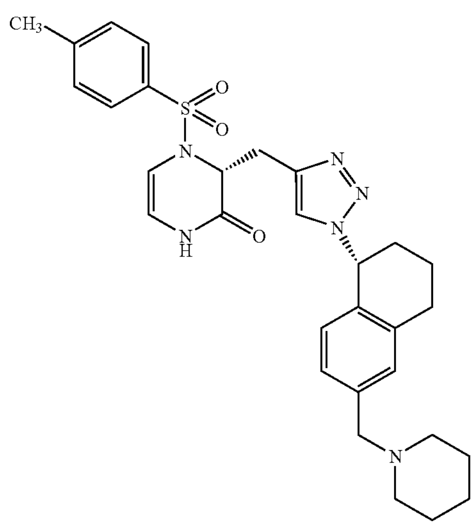 | Calcd. 560.719<br>Found: 561.2 |

-continued

| Compound Name | Structure | MS data (M + 1) |
|---|---|---|
| (R)-2-((1-((R)-6-(piperidin-1-ylmethyl)-1,2,3,4-tetrahydro-naphthalen-1-yl)-1H-1,2,3-triazol-4-yl)methyl)-1-tosyl-1,2-dihydro-pyrido[2,3-b]pyrazin-3(4H)-one | 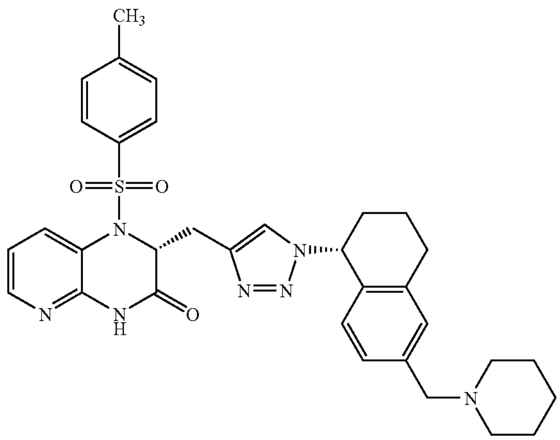 | Calcd. 611.767<br>Found: 612.2 |
| (R)-3-((1-((R)-6-(piperidin-1-ylmethyl)-1,2,3,4-tetrahydro-naphthalen-1-yl)-1H-1,2,3-triazol-4-yl)methyl)-4-tosyl-3,4-dihydropyrido[3,2-b]pyrazin-2(1H)-one | 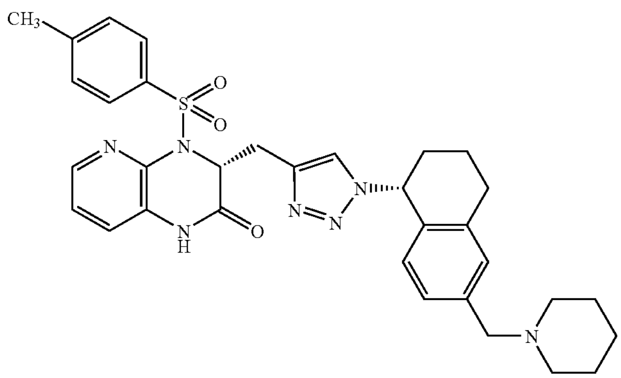 | Calcd. 611.767<br>Found: 612.2 |
| (R)-4-(3,4-dichlorophenyl-sulfonyl)-3-((3-((R)-6-(piperidin-1-ylmethyl)-1,2,3,4-tetrahydronaphthalen-1-yl)-3H-1,2,3-triazol-4-yl)methyl)-3,4-dihydropyrazin-2(1H)-one | 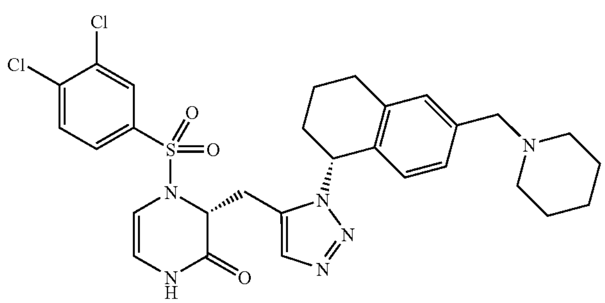 | Calcd. 615.57<br>Found: 615.2 |
| (R)-4-(3,4-dichlorophenyl-sulfonyl)-3-((1-((R)-6-(piperidin-1-ylmethyl)-1,2,3,4-tetrahydronaphthalen-1-yl)-1H-1,2,3-triazol-4-yl)methyl)-3,4-dihydropyrazin-2(1H)-one | 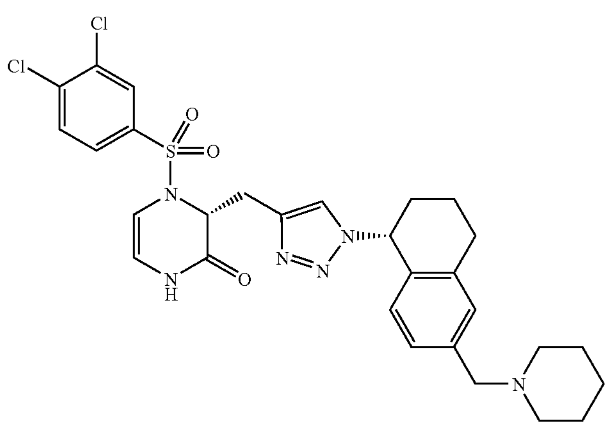 | Calcd. 615.57<br>Found: 615.2 |

-continued

| Compound Name | Structure | MS data (M + 1) |
|---|---|---|
| methyl 4-((R)-1-(4-(((R)-1-(3,4-dichlorophenylsulfonyl)-3-oxo-1,2,3,4-tetrahydropyrazin-2-yl)-methyl)-1H-1,2,3-triazol-1-yl)ethyl)-benzoate | 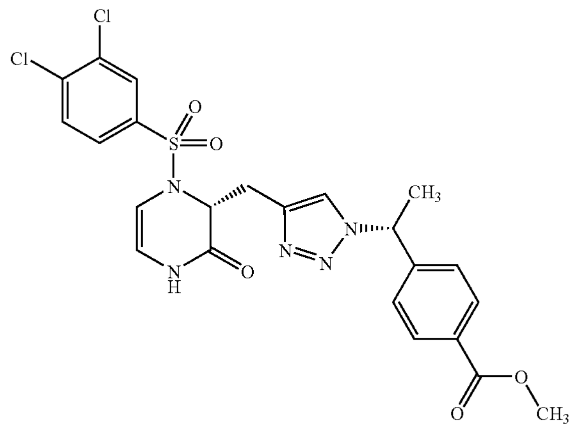 | Calcd. 550.421<br>Found: 550.4 |
| (R)-methyl 5-(4-(((R)-1-(3,4-dichlorophenylsulfonyl)-3-oxo-1,2,3,4-tetrahydropyrazin-2-yl)-methyl)-1H-1,2,3-triazol-1-yl)-5,6,7,8-tetrahydro-naphthalene-2-carboxylate | 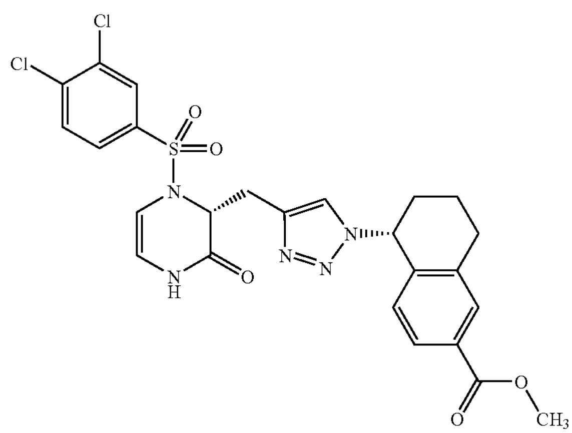 | |
| (R)-4-(2-(4-((3-oxo-1-tosyl-piperazin-2-yl)methyl)-1H-1,2,3-triazol-1-yl)ethyl)-benzonitrile | 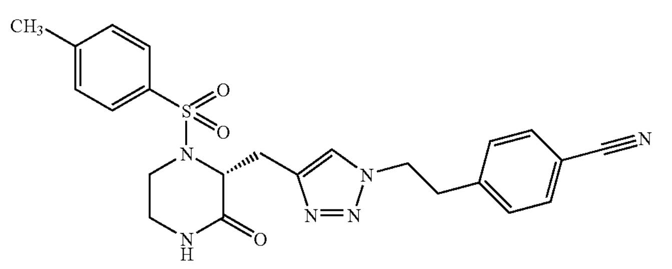 | Calcd. 464.548<br>Found: 465.2 |
| (R)-3-((1-(4-(4,5-dihydro-1H-imidazol-2-yl)phenethyl)-1H-1,2,3-triazol-4-yl)methyl)-4-tosylpiperazin-2-one | 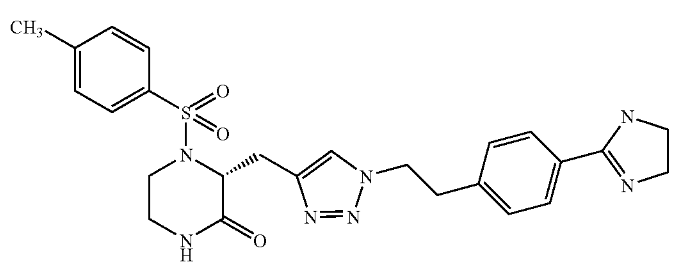 | Calcd. 507.616<br>Found: 508.2 |

-continued

| Compound Name | Structure | MS data (M + 1) |
|---|---|---|
| (R)-3-((1-(4-(4H-1,2,4-triazol-3-yl)phenethyl)-1H-1,2,3-triazol-4-yl)methyl)-4-tosylpiperazin-2-one | 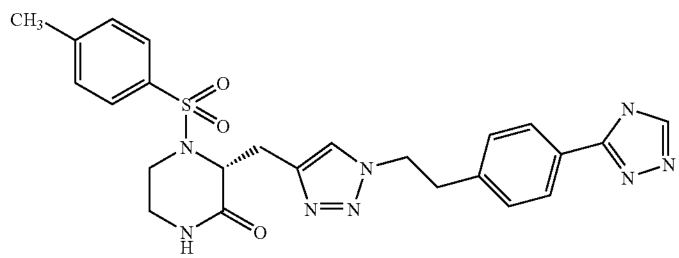 | Calcd. 506.588<br>Found: 507.2 |
| (R)-3-((1-(4-(4,5-dihydro-1H-imidazol-2-yl)phenethyl)-1H-1,2,3-triazol-4-yl)methyl)-4-tosyl-3,4-dihydropyrazin-2(1H)-one | 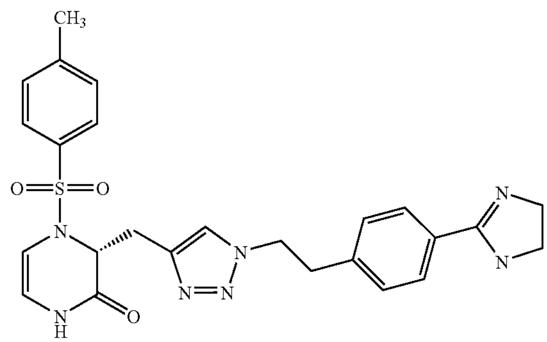 | Calcd. 506.6<br>Found: 506.2 |
| (R)-3-((1-(4-(4,5-dihydro-1H-imidazol-2-yl)phenethyl)-1H-1,2,3-triazol-4-yl)methyl)-4-(4-methoxyphenylsulfonyl)piperazin-2-one | 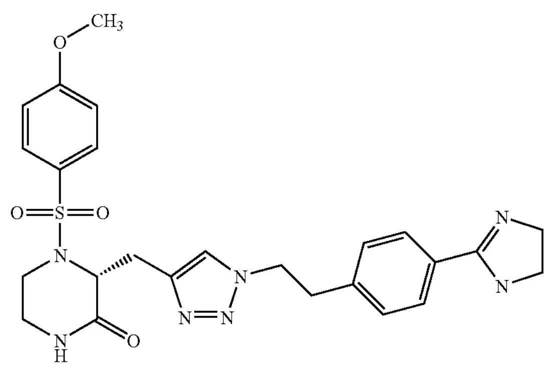 | Calcd. 523.615<br>Found: 524.2 |
| (R)-3-((1-((R)-6-(((S)-2-(hydroxymethyl)pyrrolidin-1-yl)methyl)-1,2,3,4-tetrahydro-naphthalen-1-yl)-1H-1,2,3-triazol-4-yl)methyl)-4-tosylpiperazin-2-one | 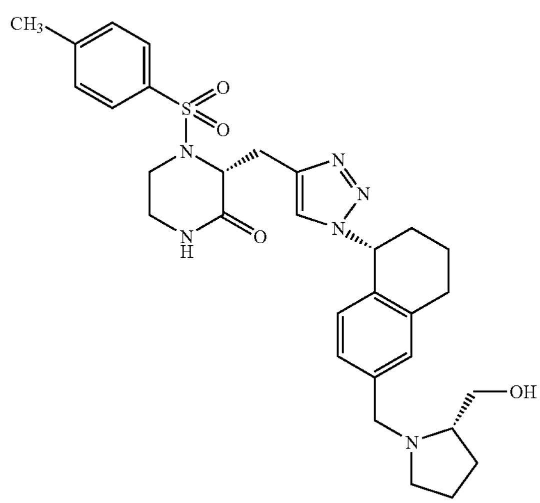 | Calcd. 578.734<br>Found: 579.2 |

| Compound Name | Structure | MS data (M + 1) |
|---|---|---|
| (R)-3-((1-((R)-6-(((R)-2-(hydroxyl-methyl)pyrrolidin-1-yl)methyl)-1,2,3,4-tetrahydro-naphthalen-1-yl)-1H-1,2,3-triazol-4-yl)methyl)-4-tosylpiperazin-2-one | 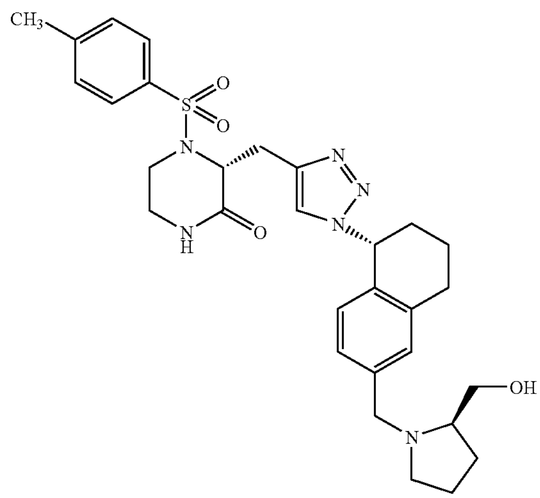 | Calcd. 578.734<br>Found: 579.2 |
| (R)-4-(3,4-dichlorophenyl-sulfonyl)-3-((1-((R)-3-(2,2,2-trifluoroacetyl)-1,2,3,4,7,8,9,10-octahydrobenzo-[f]isoquinolin-7-yl)-1H-1,2,3-triazol-4-yl)methyl)-3,4-dihydropyrazin-2(1H)-one | 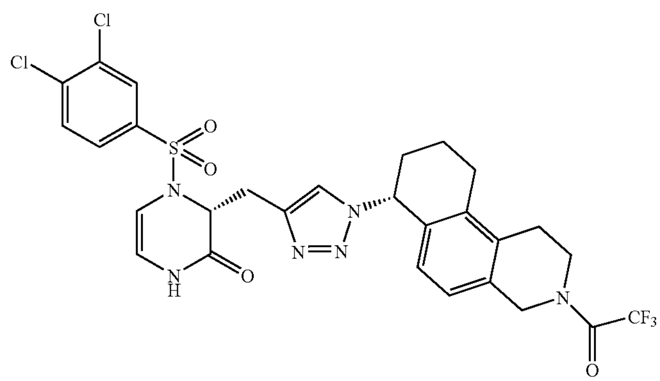 | Calcd. 669.51<br>Found: 669 |
| (R)-4-(3,4-dichlorophenyl-sulfonyl)-3-((1-((R)-2-(2,2,2-trifluoroacetyl)-1,2,3,4,7,8,9,10-octahydrobenzo-[h]isoquinolin-7-yl)-1H-1,2,3-triazol-4-yl)methyl)-3,4-dihydropyrazin-2(1H)-one | 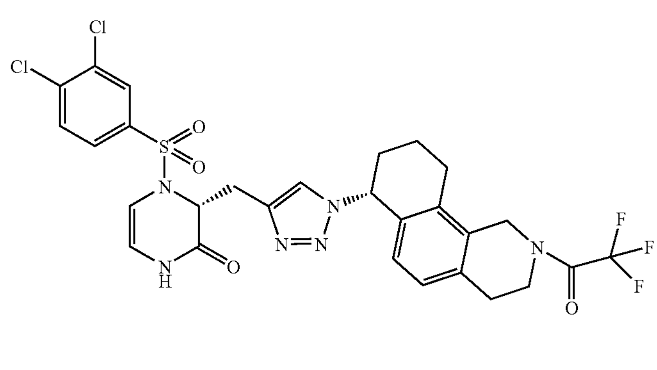 | Calcd. 669.51<br>Found: 669 |

-continued

| Compound Name | Structure | MS data (M + 1) |
|---|---|---|
| (R)-4-(3,4-dichlorophenyl-sulfonyl)-3-((1-((R)-2-isobutyl-1,2,3,4,6,7,8,9-octahydro-benzo[g]isoquinolin-6-yl)-1H-1,2,3-triazol-4-yl)methyl)-3,4-dihydropyrazin-2(1H)-one | 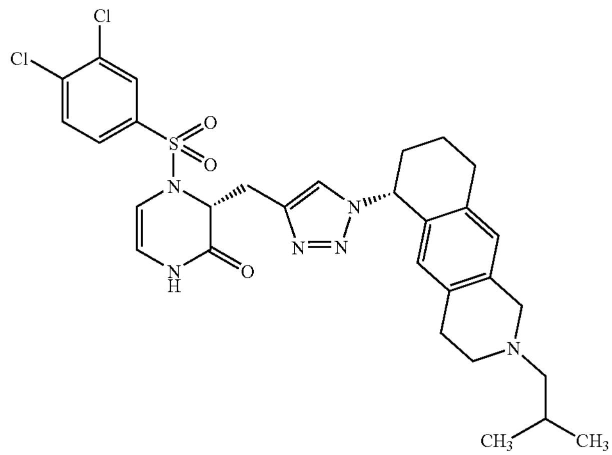 | Calcd. 629.61<br>Found: 629.1 |
| (R)-3-((1-((S)-2-(2-(azepan-1-yl)ethyl)-5,6,7,8-tetrahydro-quinazolin-5-yl)-1H-1,2,3-triazol-4-yl)methyl)-4-(3,4-dichloro-phenyl-sulfonyl)-3,4-dihydro-pyrazin-2(1H)-one | 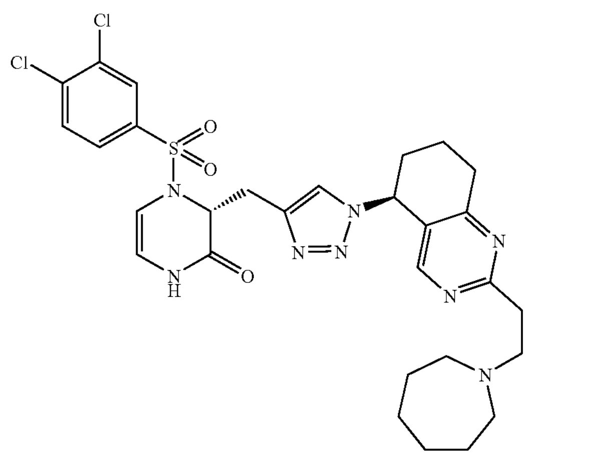 | Calcd. 645.61<br>Found: 645.1 |
| (R)-3-((1-((R)-2-(2-(azepan-1-yl)ethyl)-5,6,7,8-tetrahydro-quinazolin-5-yl)-1H-1,2,3-triazol-4-yl)methyl)-4-(3,4-dichloro-phenyl-sulfonyl)-3,4-dihydro-pyrazin-2(1H)-one | 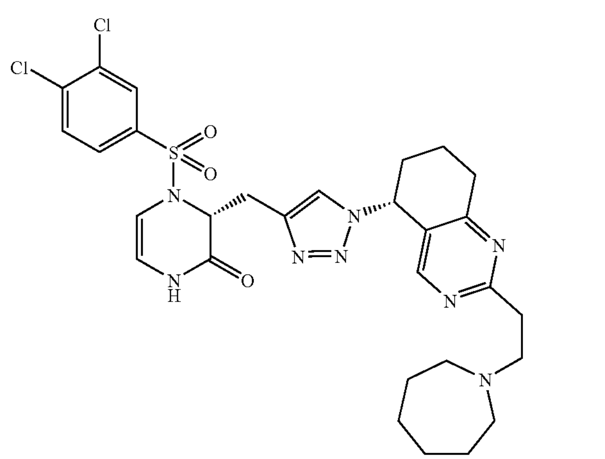 | Calcd.<br>Calcd. 645.61<br>Found: 645.1 |

The following examples can be made using the above examples and generic schemes.

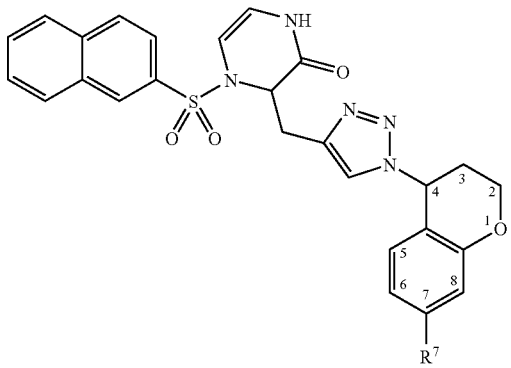

R[7]
—(CH$_2$)$_2$piperdidin-1-yl;
—CH$_2$N(CH$_3$)$_2$;
—CH$_2$piperazin-1-yl;
—CH$_2$(4-CH$_3$-piperazin-1-yl);
—CH$_2$N(Et)$_2$;

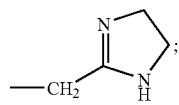

—(CH$_2$)$_2$N(CH$_3$)(Et)$_2$; or
—CH$_2$)$_2$piperazin-1-yl; and are named as follows:
  4-(naphthalen-2-ylsulfonyl)-3-((1-(7-(2-piperidin-1-yl-ethyl)chroman-4-yl)-1H-1,2,3-triazol-4-yl)methyl)-3,4-dihydropyrazin-2(1H)-one;
  4-(naphthalen-2-ylsulfonyl)-3-((1-(7-(dimethylaminomethyl)chroman-4-yl)-1H-1,2,3-triazol-4-yl)methyl)-3,4-dihydropyrazin-2(1H)-one;
  4-(naphthalen-2-ylsulfonyl)-3-((1-(7-(piperidin-1-ylmethyl)chroman-4-yl)-1H-1,2,3-triazol-4-yl)methyl)-3,4-dihydropyrazin-2(1H)-one;
  4-(naphthalen-2-ylsulfonyl)-3-((1-(7-(4-methylpiperazin-1-ylmethyl)chroman-4-yl)-1H-1,2,3-triazol-4-yl)methyl)-3,4-dihydropyrazin-2(1H)-one;
  4-(naphthalen-2-ylsulfonyl)-3-((1-(7-(diethylaminomethyl)chroman-4-yl)-1H-1,2,3-triazol-4-yl)methyl)-3,4-dihydropyrazin-2(1H)-one;
  4-(naphthalen-2-ylsulfonyl)-3-((1-(7-(4,5-dihydroimidazol-2-ylmethyl)chroman-4-yl)-1H-1,2,3-triazol-4-yl)methyl)-3,4-dihydropyrazin-2(1H)-one;
  4-(naphthalen-2-ylsulfonyl)-3-((1-(7-(2-ethylmethylaminoethyl)chroman-4-yl)-1H-1,2,3-triazol-4-yl)methyl)-3,4-dihydropyrazin-2(1H)-one; and
  4-(naphthalen-2-ylsulfonyl)-3-((1-(7-(2-piperazin-1-yl-ethyl)chroman-4-yl)-1H-1,2,3-triazol-4-yl)methyl)-3,4-dihydropyrazin-2(1H)-one.

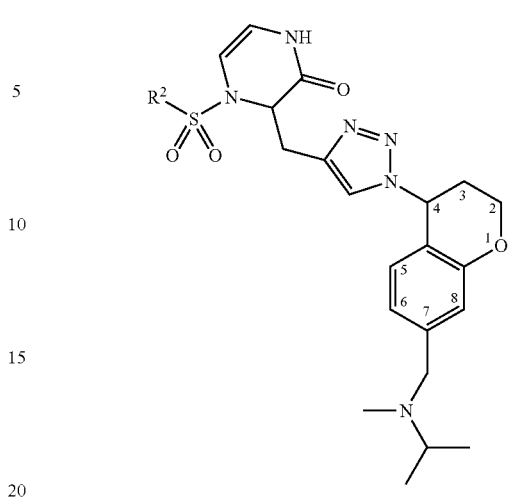

R[2]
5,6,7,8-tetrahydronaphth-2-yl;
2-quinolyl;
phenyl;
2-chlorophenyl;
3-chlorophenyl;
4-chlorophenyl;
4-methoxyphenyl;
3,5-dichlorophenyl;
3-methoxyphenyl;
3-fluorophenyl;
3-biphenyl;
4-biphenyl;
3-methylphenyl;
3-CF$_3$-phenyl;
2,4,6-trichlorophenyl;
2,3,4-trichlorophenyl;
2,4,5-trichlorophenyl;
3,4-dichlorophenyl;
4-t-butylphenyl;
1-naphthyl;
4-methyl-1-naphthyl;
phenyl-ethenyl;
benzo[1,2,5]oxadiazol-5-yl;
5-(dimethylamino)naphth-1-yl;
5-chloro-3-methylphenyl;
benzothiazol-2-yl;
2,3,4,5,6-pentamethylphenyl;
6-methoxy-2-naphthyl;
3-chloro-4-methylphenyl;
5-methoxy-3-methylbenzothien-2-yl;
6-methoxy-3-methylbenzothien-2-yl;
5-chloro-3-methylbenzothien-2-yl;
3-methylbenzothien-2-yl;
2,4-dichloro-5-methylphenyl;
3,5-dichloro-4-methylphenyl;
2,4-dichloro-3-methylphenyl;
7-methoxy-2-naphthyl;
6-fluoroethoxy-2-naphthyl;
3-methyl-5-trifluoromethoxybenzofur-2-yl;
3-methyl-5-methoxybenzofur-2-yl;
5-chloro-benzo[1,2,5]oxadiazol-4-yl;
3-methyl-5-trifluoromethoxybenzothien-2-yl;
6-ethoxy-2-naphthyl;
2-Cl-4-CF$_3$-phenyl;
6-bromonaphthyl;

3-methylbenzofur-2-yl;
3-chlorobenzothien-2-yl;
5-chloro-benzo[1,2,5]thiadiazol-4-yl;
5-chloro-1,3-dimethyl-1H-pyrazol-4-yl;
2,3-dichlorothien-5-yl;
2,5-dichlorothien-3-yl;
5-chloro-2-naphthyl;
4-butoxyphenyl;
3,5-di(trifluoromethyl)phenyl;
5-(isoxazol-3-yl)thien-2-yl;
2-chlorothien-5-yl;
4-chloro-benzo[1,2,5]oxadiazol-7-yl;
2,4-dichloro-6-methylphenyl;
2,4,6-trimethylphenyl;
2,5-dimethylphenyl;
4-chloro-2,5-dimethylphenyl;
2,5-dichlorophenyl;
3,4-difluorophenyl;
3-chloro-4-fluorophenyl;
2-methyl-5-trifluoromethylphenyl;
4-methylcyclohexyl;
3,5-dimethylbenzothien-2-yl;
5-fluoro-3-methylbenzothien-2-yl;
5-methylbenzothien-2-yl;
5-chloro-3-methylbenzofur-2-yl; or
3-pyridyl;

and are named as:

3-((1-(7-((isopropyl(methyl)amino)methyl)chroman-4-yl)-1H-1,2,3-triazol-4-yl)methyl)-4-(5,6,7,8-tetrahydronaphth-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2-quinolyl sulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(phenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2-chlorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-chlorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(4-chlorophenylsulfonyl lsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(4-methoxyphenylsulfonyl ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3,5-dichlorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-methoxyphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-fluorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(biphen-3-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(biphen-4-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-methylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-trifluoromethylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,3,4-trichlorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,4,5-trichlorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3,4-dichlorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(4-t-butylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(naphtha-1-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(4-methylnaphth-1-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(phenylethen-1-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(benzo[1,2,5]oxadiazol-5-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-(dimethylamino)naphth-1-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-chloro-3-methylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(benzothiazol-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,3,4,5,6-pentamethylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(6-methoxy-2-naphthylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-chloro-4-methylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-methoxy-3-methylbenzothien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(6-methoxy-3-methylbenzothien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-chloro-3-methylbenzothien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-methylbenzothien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,4-dichloro-5-methylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3,5-dichloro-4-methylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,4-dichloro-3-methylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(7-methoxy-2-naphthylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(6-fluoroethoxy-2-naphthylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-methyl-5-trifluoromethoxybenzofur-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-methyl-5-methoxybenzofur-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-chloro-benzo[1,2,5]oxadiazol-4-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-methyl-5-trifluoromethoxybenzothien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(6-ethoxy-2-naphthylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2-$C_{1-4}$-$CF_3$-phenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(6-bromonaphthylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-methylbenzofur-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-chlorobenzothien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-chloro-benzo[1,2,5]thiadiazol-4-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-chloro-1,3-dimethyl-1H-pyrazol-4-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,3-dichlorothien-5-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,5-dichlorothien-3-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-chloro-2-naphthylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(4-butoxyphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3,5-di(trifluoromethyl)phenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-(isoxazol-3-yl)thien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2-chlorothien-5-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(4-chloro-benzo[1,2,5]oxadiazol-7-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,4-dichloro-6-methylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,4,6-trimethylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,5-dimethylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(4-chloro-2,5-dimethylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,5-dichlorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(4-chloro-2,5-dimethylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3,4-difluorophenylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-chloro-4-fluorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2-methyl-5-trifluoromethylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(4-methylcyclohexylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3,5-dimethylbenzothien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-fluoro-3-methylbenzothien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-methylbenzothien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-chloro-3-methylbenzofur-2-ylsulfonyl)-3,4-dihydropyrazin-2(1H)-one; and 3-((1-(7-((isopropyl(methyl)amino)methyl)chroman-4-yl)-1H-1,2,3-triazol-4-yl)methyl)-4-(3-pyridylsulfonyl)-3,4-dihydropyrazin-2(1H)-one.

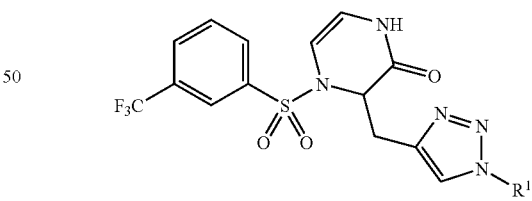

$R^1$
3-isopropyl-7-(1-methylpiperidin-2-yl)chroman-4-yl;
2,2-dimethyl-7-(1-methylpiperidin-2-yl)chroman-4-yl;
7-(piperidin-2-yl)chroman-4-yl;
2,2-dimethyl-7-(methylaminomethyl)chroman-4-yl;
7-(dimethylaminomethyl)-1,2,3,4-tetrahydronaphth-4-yl;
7-(piperidin-1-ylaminomethyl)-1,2,3,4-tetrahydronaphth-2-yl;
5-(piperidin-1-yl)methylindan-1-yl;
6-(4-methylpiperazin-1-yl)methylindan-1-yl;
4-(piperazin-1-yl)methylindan-1-yl;

2-(di-ethylaminomethyl)-5,6,7,8-tetrahydroquinolin-5-yl;
2-(isopropylaminomethyl)-5,6,7,8-tetrahydroquinolin-8-yl;
2-(t-butylaminomethyl)-5,6,7,8-tetrahydoisoquinolin-8-yl;
7-(morpholin-4-ylmethyl)-quinolin-4-yl;
1-methyl-2-oxo-6-(piperidin-1-yl)methylindol-3-yl;
7-(dimethylaminomethyl)-1,2,3,4-tetrahydronaphth-2-yl;
7-(diethylaminomethyl)-4,5,6,7-tetrahydobenzofur-4-yl;
7-(4-morpholinylmethyl)-4,5,6,7-tetrahydobenzothien-4-yl;
7-(aminomethoxy)chroman-4-yl;
4-4-(4,5-dihydro-1H-imidazol-2-yl)-phenylethyl;
4-4-(4,5-dihydro-1H-imidazol-2-yl)-phenyl;
4-(aminopropyl)phenyl; or
4-(aminoethyl)phenyl;

and are named as:

3-((1-(3-isopropyl-7-(1-methylpiperidin-2-yl)chroman-4-yl)-1H-1,2,3-triazol-4-yl)methyl)-4-(3-trifluoromethylsulfonyl)-3,4-dihydropyrazin-2(1H)-one;

3-((1-(2,2-dimethyl-7-(1-methylpiperidin-2-yl)chroman-4-yl)-1H-1,2,3-triazol-4yl)methyl)-4-(3-trifluoromethylsulfonyl)-3,4-dihydropyrazin-2(1H)-one;

3-((1-(7-(piperidin-2-yl)chroman-4-yl)-1H-1,2,3-triazol-4-yl)methyl)-4-(3-trifluoromethylphenylsulfonyl)-3,4-dihydropyrazin-2(1H)-one;

3-((1-(2,2-dimethyl-7-(methylaminomethyl)chroman-4-yl)-1H-1,2,3-triazol-4-yl)methyl)-4-yl)methyl)-4-(3-trifluoromethylsulfonyl)-3,4-dihydropyrazin-2(1H)-one;

3-((1-(7-(dimethylaminomethyl)-1,2,3,4-tetrahydonaphth-4-yl)-1H-1,2,3-triazol-4-yl)methyl)-4-(3-trifluoromethylphenylsulfonyl)-3,4-dihydropyrazin-2(1H)-one;

3-((1-(7-(piperidin-1-ylaminomethyl)-1,2,3,4-tetrahydonaphth-2-yl)-1H-1,2,3-triazol-4-yl)methyl)-4-(3-trifluoromethylsulfonyl)-3,4-dihydropyrazin-2(1H)-one;

3-((1-(5-(piperidin-1-yl)methylindan-1-yl)-1H-1,2,3-triazol-4-yl)methyl)-4-(3-trifluoromethylphenylsulfonyl)-3,4-dihydropyrazin-2(1H)-one;

3-((1-(6-(4-methylpiperazin-1-yl)methylindan-1-yl)-1H-1,2,3-triazol-4-yl)methyl)-4-(3-trifluoromethylsulfonyl)-3,4-dihydropyrazin-2(1H)-one;

3-((1-(4-(piperazin-1-yl)methylindan-1-yl)-1H-1,2,3-triazol-4-yl)methyl)-4-(3-trifluoromethylphenylsulfonyl)-3,4-dihydropyrazin-2(1H)-one;

3-((1-(2-(di-ethylaminomethyl)-5,6,7,8-tetrahydoquinolin-5-yl)-1H-1,2,3-triazol-4-yl)methyl)-4-(3-trifluoromethylphenylsulfonyl)-3,4-dihydropyrazin-2(1H)-one;

3-((1-(2-(isopropylaminomethyl)-5,6,7,8-tetrahydoquinolin-8-yl)-1H-1,2,3-triazol-4-yl)methyl)-4-(3-trifluoromethylphenylsulfonyl)-3,4-dihydropyrazin-2(1H)-one;

3-((1-(2-(t-butylaminomethyl)-5,6,7,8-tetrahydoisoquinolin-8-yl)-1H-1,2,3-triazol-4-yl)methyl)-4-(3-trifluoromethylphenylsulfonyl)-3,4-dihydropyrazin-2(1H)-one;

3-((1-(7-(morpholin-4-ylmethyl)-quinolin-4-yl)-1H-1,2,3-triazol-4-yl)methyl)-4-(3-trifluoromethylphenylsulfonyl)-3,4-dihydropyrazin-2(1H)-one;

3-((1-(1-methyl-2-oxo-6-(piperidin-1-yl)methylindol-3-yl)-1H-1,2,3-triazol-4-yl)methyl)-4-(3-trifluoromethylsulfonyl)-3,4-dihydropyrazin-2(1H)-one;

3-((1-(7-(dimethylaminomethyl)-1,2,3,4-tetrahydonaphth-2-yl)-1H-1,2,3-triazol-4-yl)methyl)-4-(3-trifluoromethylphenylsulfonyl)-3,4-dihydropyrazin-2(1H)-one;

3-((1-(7-(diethylaminomethyl)-4,5,6,7-tetrahydobenzofur-4-yl)-1H-1,2,3-triazol-4-yl)methyl)-4-(3-trifluoromethylphenylsulfonyl)-3,4-dihydropyrazin-2(1H)-one;

3-((1-(7-(4-morpholinylmethyl)-4,5,6,7-tetrahydobenzothien-4-yl)-1H-1,2,3-triazol-4-yl)methyl)-4-(3-trifluoromethylsulfonyl)-3,4-dihydropyrazin-2(1H)-one;

3-((1-(7-(aminomethoxy)chroman-4-yl)-1H-1,2,3-triazol-4-yl)methyl)-4-(3-trifluoromethylsulfonyl)-3,4-dihydropyrazin-2(1H)-one;

3-((1-(4-4-(4,5-dihydro-1H-imidazol-2-yl)-phenylethyl)-1H-1,2,3-triazol-4-yl)methyl)-4-(3-trifluoromethylphenylsulfonyl)-3,4-dihydropyrazin-2(1H)-one;

3-((4-4-(4,5-dihydro-1H-imidazol-2-yl)-phenyl)-1H-1,2,3-triazol-4-yl)methyl)-4-(3-trifluoromethylsulfonyl)-3,4-dihydropyrazin-2(1H)-one;

3-((1-(4-(aminopropyl)phenyl)-1H-1,2,3-triazol-4-yl)methyl)-4-(3-trifluoromethylsulfonyl)-3,4-dihydropyrazin-2(1H)-one;

3-((1-(4-(aminoethyl)phenyl)-1H-1,2,3-triazol-4-yl)methyl)-4-(3-trifluoromethylsulfonyl)-3,4-dihydropyrazin-2(1H)-one;

Biological Testing

Although the pharmacological properties of the compounds of the invention vary with structural change, in general, activity possessed by compounds of the invention may be demonstrated in vivo. The pharmacological properties of the compounds of this invention may be confirmed by a number of pharmacological in vitro assays. The exemplified pharmacological assays, which follow, have been carried out with the compounds according to the invention and their salts. Compounds of the present invention showed binding $IC_{50}$'s of B1 at doses less than 20 µM.

Human Bradykinin B1 Receptor and human B2 Receptor In Vitro Binding Assays

Example 1

Radioligand Binding Assay for human B1 and human B2 bradykinin receptor

Step 1 Preparation of membranes expressing human B1 bradykinin receptor:

Membranes were prepared from CHO-d⁻AQN cells stably transfected with human bradykinin B1 receptor cDNA. For large-scale production of membranes, cells were grown in 100 L suspension culture to 1.0E8 cells/mL then harvested using the Viafuge at continuous centrifugation of 1000 g. For pilot studies, cells were grown in 2 L spinner culture and harvested by centrifugation (1900 g, 10 min, 4° C.). The cell pellet was washed with PBS, centrifuged (1900 g, 10 min, 4° C.), then the cells resuspended in lysis buffer (25 mM HEPES, pH 7.4, 5 mM EDTA, 5 mM EGTA, 3 mM $MgCl_2$, 10% (w/v) sucrose, Complete Protease Inhibitor tablets (EDTA-free)) to a density of 14% w/v for passage through a microfluidizer (Microfluidics 110S, 3 passes, 6,000 psi). The resulting cell lysate was centrifuged (1900 g, 10 min, 4° C.), and the crude particulate fraction isolated by centrifugation (142,000 g, 1 h, 4° C.) of the low-speed supernatant. The resulting pellet was resuspended in ⅓ the original lysis buffer volume, homogenized, and recentrifuged as above. The membrane pellet was resuspended by homogenization in storage buffer (25 mM HEPES, pH 7.4, 3 mM $MgCl_2$, 10% (w/v) sucrose and Complete Protease Inhibitor tablets (EDTA-free)). Single-use aliquots were made and flash-frozen in liquid $N_2$ prior to storage at −80° C.

Membranes containing human bradykinin B2 receptor were purchased from Receptor Biology (now Perkin Elmer Life Sciences). They were derived from a CHO-K1 line stably expressing the human B2 receptor developed by Receptor Biology and subsequently purchased by Amgen. For some studies, membranes were prepared in-house from this same cell line using the method described for human B1 receptor membranes, except cells were grown in roller bottles and harvested using Cellmate. Step 2 Human B1 receptor binding assay was performed in 96-well polypropylene plates (Costar 3365) by adding 50 µl [$^3$H] des-arglo kallidin (NET1064; Perkin Elmer Life Sciences) to 10 µL test compound diluted in 90 µL assay buffer (24 mM TES, pH 6.8, 1 mM 1,10 o-phenanthroline, 0.3% BSA, 0.5 mM Pefabloc SC, 2 pg/mL aprotinin, 5 pg/mL leupeptin, and 0.7 µg/mL pepstatin A). Membranes (50 µL) were added last. [$^3$H] des-arg$^{10}$ kallidin was diluted from stock into assay buffer to yield a final concentration of 0.3 nM in the assay but was adjusted as needed to ensure a concentration at or below the Kd determined for each batch of receptor membranes. Nonspecific binding was defined with 2 MM des-Argl$^0$Leu$^9$ kallidin. Membranes were diluted in assay buffer to yield a final concentration of 0.068 nM hB1 receptor in the assay. Compounds were solubilized in either DMSO or ddH$_2$O, plated into polypropylene plates (Costar 3365), then serially diluted in either DMSO or dilution buffer (20 mM Hepes, pH 7.6, 0.1 % BSA) to yield a final concentration of either 5% DMSO or no DMSO in the assay. The assay mixture was incubated with shaking for 1 h at RT and then filtered through GF/C plates presoaked in 0.5% polyethyleneimine (Unifilter; Perkin Elmer Life Sciences) using a Filtermate 96-well harvester (Perkin Elmer Life Sciences). Filter plates were rapidly washed 6 times with 200 µL ice-cold buffer (50 mM Tris, pH 7.4), dried in a vacuum oven at 55° C. for 15-20 min, backed, and 40 µL per well of Microscint 20 was added. The plates were sealed and activity read on Topcount (Perkin Elmer Life Sciences) using a count time of 3 min per channel.

For human B2 bradykinin receptor, the same procedure was followed with the following exceptions: [$^3$H] bradykinin (NET706; Perkin Elmer Life Sciences) was used at a final concentration of 0.2 nM and non-specific binding was defined with 2M bradykinin. Human B2 receptor concentration was 0.068 nM final in the assay.

Data analysis

Data was analyzed in XLFit with the four-parameter logistic $y=A+((B-A)/(1+((C/x)^{\wedge}D)))$ and fit with the Levenburg-Marquardt algorithm. Raw cpm were converted to percent of control values prior to analysis (POC=((compound cpm−nonspecific cpm)/(no-compound cpm−nonspecific cpm) *100)). $K_i$ values were determined from the $IC_{50}$ using the Cheng-Prusoff equation and $K_d$ values determined by direct saturation binding of the radioligands.

Example 2

In vitro B1-Inhibition Activity

In vitro Assay of human B1 Receptor Function using Calcium Flux

Activation of the $G_q$ linked B1 receptor results in an increase in intracellular calcium. The calcium sensitive photoprotein aequorin can, therefore, be used as an indicator of B1 receptor activation. A-equorin is a 21-kDa photoprotein that forms a bioluminescent complex when linked to the chromophore cofactor coelenterazine. Following the binding of calcium to this complex, an oxidation reaction of coelenterazine results in the production of apoaequorin, coelenteramide, $CO_2$, and light that can be detected by conventional luminometry.

A stable CHO D-/hB1/Aequorin cell line was established and the cells were maintained in suspension in spinner bottles containing a 1:1 ratio of DMEM and HAM F12 (Gibco 11765-047), high glucose (Gibco 11965-084), 10% Heat Inactivated Dialyzed serum (Gibco 26300-061), 1× Non-Essential Amino Acids (Gibco 11140-050), 1× Glutamine-Pen—Strep (Gibco 10378-016), and Hygromycin, 300 µg/mL (Roche 843555). 15-24 h prior to the luminometer assay, 25,000 cells/well (2.5E6 cells/10 mL/plate) were plated in 96-well black-sided clear bottom assay plates (Costar #3904).

Media was removed from the wells and replaced with 60 µL of serum free HAM's F12 with 30 mM HEPES (pH 7.5) and 15 µM coelenterazine (Coelenterazine h Luciferin #90608 from Assay Designs). The plates were incubated for 1.5-2 h. Ten point $IC_{50}$ compound plates containing 1:3 or 1:5 dilutions of antagonist compounds and an agonist activator plate (20 nM des-Arg10-Kallidin final concentration, $EC_{80}$) were prepared using Ham's F12 with 30 mM HEPES, pH 7.5. Following coelenterazine incubation, an automated flash-luminometer platform was used to dispense the B1 antagonist compounds (dissolved in DMSO and diluted with buffer to the desired concentration (final DMSO concentration <1% DMSO)) to the cell plate, a CCD camera situated underneath the cell plate took 12 images of the cell plate at 5 second intervals to determine if there was any agonist activity with the compounds. The hB1 agonist, des-Arg$_{10}$-Kallidin, was added to the cell plate and another 12 images were recorded to determine tied $IC_{50}$ of the antagonist(s).

In vitro Assay of hB2 Receptor Function using Calcium Flux

The intracellular calcium flux induced by hB2 receptor activation was analyzed using an hB2 recombinant cell line (CHO-K1) purchased from PerkinElmer (Catalog Number: RBHB2C000EA) on a fluorometric imaging plate reader (FLIPR). The cells were cultured in T225 flask containing Ham's F12 Nutrient Mixture (Invitrogen Corp., Cat # 11765-047), 10% Fetal Clone II Bovine Serum (HyClone, Cat # SH3006603), 1 mM Sodium pyruvate (100 mM stock, Invitrogen Corp., Cat #12454-013), and 0.4 mg/mL Geneticin (G418; 50 mg/mL active geneticin, Invitrogen, Cat #10131-207). Culture medium was changed every other day. 24 h prior to the FLIPR assay, the hB2/CHO cells were washed once with PBS (Invitrogen) and 10 mL of Versene (1:5000, Invitrogen, Cat #15040-066) was added to each flask. After 5 min incubation at 37° C., Versene was removed and cells were detached from the flask and resuspended in culture medium. Cells were counted and 25,000 cells/well were plated in 96-well black-sided clear bottom assay plates (Costar #3904). Cells were incubated in a 37° C. $CO_2$ incubator overnight.

The media was aspirated from the cells and replaced with 65 gL of dye-loading buffer. The loading buffer was prepared by diluting a stock solution of 0.5mM Fluo-4 AM (Molecular Probes, dissolved in DMSO containing 10% [w/v] pluronic acid) to a concentration of 1 µM in Clear Dulbecco's Modified Eagle Medium (DMEM) containing 0.1% BSA, 20 mM HEPES, and 2.5 mM probenecid. The cells were dye-loaded for 1 h at RT. The excess dye was removed by washing the cells 2× with assay buffer. The assay buffer consists of Hank's Balanced Salt Solution (HBSS) containing 20 mM HEPES, 0.1% BSA, and 2.5 mM probenecid. After the wash cycles, a volume of 100 gL was left in each well, and the plate was ready to be assayed in the FLIPR System. Single point (10 µM final concentration) POC antagonist compound plates or ten point $IC_{50}$ compound plates containing 1:3 or 1:5 dilutions of antagonist compounds (dissolved in DMSO and diluted with buffer to the desired concentration (final DMSO concentration <1% DMSO)) and an agonist activator plate (0.3 nM bradykinin final concentration, $EC_{80}$) were prepared using assay buffer. The cell plate and the compound plates were loaded onto the FLIPR and during the assay, fluorescence readings are taken simultaneously from all 96 wells of the cell plate. Ten 1-second readings were taken to establish a stable baseline for each well, then 25 µL from the B1 antagonist plate was rapidly (50 µL/sec.) added. The fluorescence signal was measured in 1-second (1 min) followed by 6-second (2 min) intervals for a total of 3 min to determine if there is any agonist activity with the compounds. The B2 agonist, bradykinin, was added to the cell plate and another 3 min were recorded to determine the percent inhibition at 10 µM (POC plates) or the $IC_{50}$ of the antagonist.

Example 3

Cell and Tissue based In Vitro Assays of hB1 Receptor Binding

These studies established the antagonist activity of several compounds at the bradykinin B1 receptors in in vitro cell-based and isolated organ assays.

1. Rabbit Endothelial Cell B1-specific $PGI_2$ Secretion Assay

2. B1 and B2 Umbilical Vein Assay

In Vitro B1-Inhibition Activity:

The effectiveness of the compounds as inhibitors of B1 activity (i.e., B1 "neutralization") can be evaluated by measuring the ability of each compound to block B1 stimulated CGRP and substance P release and calcium signaling in Dorsal Root Ganglion (DRG) neuronal cultures.

Dorsal Root Ganglion Neuronal Cultures:

Dorsal root ganglia are dissected one by one under aseptic conditions from all spinal segments of embryonic 19-day old (E19) rats that are surgically removed from the uterus of timed-pregnant, terminally anesthetized Sprague-Dawley rats (Charles River, Wilmington, Ma.). DRG are collected in ice-cold L-15 media (GibcoBRL, Grand Island, N.Y.) containing 5% heat inactivated horse serum (GibcoBRL), and any loose connective tissue and blood vessels are removed. The DRG are rinsed twice in $Ca^{2+}$— and $Mg^{2+}$-free Dulbecco's phosphate buffered saline (DPBS), pH 7.4 (GibcoBRL). The DRG are dissociated into single cell suspension using a papain dissociation system (Worthington Biochemical Corp., Freehold, N.J.). Briefly, DRG are incubated in a digestion solution containing 20 U/mL of papain in Earle's Balanced Salt Solution (EBSS) at 37° C. for fifty minutes. Cells are dissociated by trituration through fire-polished Pasteur pipettes in a dissociation medium consisting of MEM/Ham's F12, 1:1, 1 mg/mL ovomucoid inhibitor and 1 mg/mL ovalbumin, and 0.005% deoxyribonuclease 1 (DNase). The dissociated cells are pelleted at 200×g for 5 min and re-suspended in EBSS containing 1 mg/mL ovomucoid inhibitor, 1 mg/mL ovalbumin and 0.005% DNase. Cell suspension is centrifuged through a gradient solution containing 10 mg/mL ovomucoid inhibitor, 10 mg/mL ovalbumin at 200×g for 6 min to remove cell debris, then filtered through a 88-µM nylon mesh (Fisher Scientific, Pittsburgh, Pa.) to remove any clumps. Cell number is determined with a hemocytometer, and cells are seeded into poly-ornithine 100 µg/mL (Sigma, St. Louis, Mo.) and mouse laminin 1 µg/mL (GibcoBRL)-coated 96-well plates at $10\times10^3$ cells/well in complete medium. The complete medium consists of minimal essential medium (MEM) and Ham's F12, 1:1, penicillin (100 U/mL), streptomycin (100 µg/mL), and 10% heat inactivated horse serum (GibcoBRL). The cultures are kept at 37° C., 5% $CO_2$ and 100% humidity. For controlling the growth of non-neuronal cells, 5-fluoro-2'-deoxyuridine (75 µM) and uridine (180 µM) are included in the medium.

Two hours after plating, cells are treated with recombinant human β-b1 or recombinant rat β-b1 at a concentration of 10 mg/ml (0.38 nm). Positive controls comprising serial-diluted anti-b1 antibody (r&d systems, Minneapolis, Mn.) are applied to each culture plate. Compounds are added at ten concentrations using 3.16-fold serial dilutions. All samples are diluted in complete medium before being added to the cultures. Incubation time is generally around 40 h prior to measurement of vr1 expression.

Measurement of VR1 Expression in DRG Neurons:

Cultures are fixed with 4% paraformaldehyde in Hanks' balanced salt solution for 15 min, blocked with Superblock (Pierce, Rockford, Ill.), and permeabilized with 0.25% Nonidet P-40 (Sigma) in Tris.HCl (Sigma)-buffered saline (TBS) for 1 h at RT. Cultures are rinsed once with TBS containing 0.1% Tween 20 (Sigma) and incubated with rabbit anti-VR1 IgG (prepared at Amgen) for 1.5 h at RT, followed by incubation of Eu-labeled anti-rabbit second antibody (Wallac Oy, Turku, Finland) for 1 h at RT. Washes with TBS (3× five min with slow shaking) are applied after each antibody incubation. Enhance solution (150 mL/well, Wallac Oy) is added to the cultures. The fluorescence signal is measured in a time-resolved fluorometer (Wallac Oy). VR1 expression in samples treated with the compounds is determined by comparing to a standard curve of B1 titration from 0-1000 ng/mL. Percent inhibition (compared to maximum possible inhibition) of B1 effect on VR1 expression in DRG neurons is determined by comparing to controls that are not B1-treated.

Example 4

In Vivo Antinociceptive Activity in Rat and Monkey Pain Models

Rat Neuropathic Pain Model

Male Sprague-Dawley rats (200 g) are anesthetized with isoflurane inhalant anesthesia and the left lumbar spinal nerves at the level of L5 and L6 are tightly ligated (4-0 silk suture) distal to the dorsal root ganglion and prior to entrance into the sciatic nerve, as first described by Kim and Chung (Kim, S. H.; Chung, J. M. An experimental model for peripheral neuropathy produced by segmental spinal nerve ligation in the rat. Pain 50:355-363, (1992)). The incisions are closed and the rats are allowed to recover. This procedure results in mechanical (tactile) allodynia in the left hind paw as assessed by recording the pressure at which the affected paw (ipsilateral to the site of nerve injury) was withdrawn from graded stimuli (von Frey filaments ranging from 4.0 to 148.1 mN) applied perpendicularly to the plantar surface of the paw (between the footpads) through wire-mesh observation cages. A paw withdrawal threshold (PWT) was determined by sequentially increasing and decreasing the stimulus strength and analyzing withdrawal data using a Dixon non-parametric test, as described by Chaplan et al. (Chaplan, S. R.; Bach, F. W.; Pogrel, J. W.; Chung, J. M.; Yaksh, T. L. Quantitative assessment of tactile allodynia in the rat paw. J. Neurosci. Meth., 53:55-63 (1994)).

Normal rats and sham surgery rats (nerves isolated but not ligated) withstand at least 148.1 mN (equivalent to 15 g) of pressure without responding. Spinal nerve ligated rats respond to as little as 4.0 mN (equivalent to 0.41 g) of pressure on the affected paw. Rats are included in the study only if they did not exhibit motor dysfunction (e.g., paw dragging or dropping) and their PWT was below 39.2 mN (equivalent to 4.0 g). At least seven days after surgery rats are treated with compounds (usually a screening dose of 60 mg/kg) or control diluent (PBS) once by s.c. injection and PWT was determined each day thereafter for 7 days.

Rat CFA Inflammatory Pain Model

Male Sprague-Dawley rats (200 g) are lightly anesthetized with isoflurane inhalant anesthesia and the left hindpaw is injected with complete Freund's adjuvant (CFA), 0.15 mL. This procedure results in mechanical (tactile) allodynia in the left hind paw as assessed by recording the pressure at which the affected paw is withdrawn from graded stimuli (von Frey filaments ranging from 4.0 to 148.1 mN) applied perpendicularly to the plantar surface of the paw (between the footpads) through wire-mesh observation cages. PWT is determined by sequentially increasing and decreasing the stimulus strength and analyzing withdrawal data using a Dixon non-parametric test, as described by Chaplan et al. (1994). Rats are included in the study only if they do not exhibit motor dysfunction (e.g., paw dragging or dropping) or broken skin and their PWT is below 39.2 mN (equivalent to 4.0 g). At least seven days after CFA injection rats are treated with compounds (usually a screening dose of 60 mg/kg) or control solution (PBS) once by s.c. injection and PWT is determined each day thereafter for 7 days. Average paw withdrawal threshold (PWT) is converted to percent of maximum possible effect (% MPE) using the following formula: % MPE=100*(PWT of treated rats−PWT of control rats)/(15−PWT of control rats). Thus, the cutoff value of 15 g (148.1 mN) is equivalent to 100% of the MPE and the control response is equivalent to 0% MPE.

At the screening dose of 60 mg/kg, compounds in vehicle are expected to produce an antinociceptive effect with a PD relationship.

Example 5

Green Monkey LPS Inflammation Model

The effectiveness of the compounds as inhibitors of B1 activity are evaluated in Male green monkeys (*Cercopithaecus aethiops* St Kitts) challenged locally with B1 agonists essentially as described by deBlois and Horlick (British Journal of Pharmacology, 132:327-335 (2002), which is hereby incorporated by reference in its entirety).

In order to determine whether compounds of the present invention inhibit B1 induced oedema the studies described below are conducted on male green monkeys (*Cercopithaecus aethiops* St Kitts) at the Caribbean Primates Ltd. experimental farm (St Kitts, West Indies). Procedures are reviewed and accepted by the Animal Care Committees of the CR-CHUM (Montreal, Canada) and of Caribbean Primates Ltd. (St Kitts, West Indies). Animals weighing 6.0±0.5 kg (n=67) were anaesthetized (50 mg ketamine $kg^{-1}$) and pretreated with a single intravenous injection of LPS (90 µg $kg^{-1}$) or saline (1 mL) via the saphenous vein.

Inflammation Studies

Kinin-induced oedema is evaluated by the ventral skin fold assay (Sciberras et al., 1987). Briefly, anaesthetized monkeys were injected with captopril (1 mg $kg^{-1}$ 30 min before assay). A single subcutaneous injection of dKD, BK or the vehicle (2 mM amastatin in 100 µL Ringer's lactate) is given in the ventral area and the increase in thickness of skin folds is monitored for 30-45 min using a calibrated caliper. The results are expressed as the difference between the skin fold thickness before and after the subcutaneous injection. Captopril and amastatin are used to reduce degradation of kinins at the carboxyl- and amino-terminus, respectively.

Antagonist Schild Analysis:

The dose-response relationship for dKD (1-100 nmol)-induced oedema is determined at 24 h post-LPS in the absence or presence of different concentrations of antagonist. BK (30 nmol) is used as a positive control.

Antagonist Time Course

The time course of inhibition by antagonist is determined at 4, 24 and 48 h, 72 and/or 96 h after single bolus administration. BK (30 nmol) is used as a positive control.

Drugs

Ketamine hydrochloride, LPS, amastatin and captopril are from Sigma (Missouri, U.S.A.). All peptides are from Phoenix Pharmaceuticals (California, U.S.A.).

Statistics

Values are presented as mean +standard error of the mean (s.e. mean). In edema studies, the pre-injection thickness of the skin folds was subtracted from the values after subcutaneous challenge. Curve fitting and $EC_{50}$ calculations were obtained using the Delta Graph 4.0 software for Apple Computers. Data were compared by two-way analysis of variance followed by unpaired, one tail Student's t-test with Bonferroni correction. P<0.05 was considered statistically significant.

The foregoing is merely illustrative of the invention and is not intended to limit the invention to the disclosed compounds. Variations and changes, which are obvious to one skilled in the art, are intended to be within the scope and nature of the invention, which are defined, in the appended claims.

From the foregoing description, one skilled in the art can easily ascertain the essential characteristics of this invention, and without departing from the spirit and scope thereof, can make various changes and modifications of the invention to adapt it to various usages and conditions. All mentioned references, patents, applications and publications, are hereby incorporated by reference in their entirety, as if here written.

What is claimed is:

1. A compound of Formula (I):

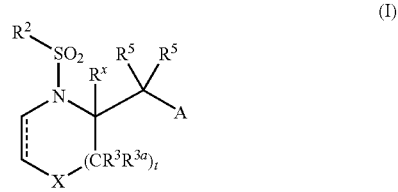

wherein:

t is 1;

X is selected from —NH— or —$NR^d$— where $R^d$ is $C_{1-8}$alkyl or $C_{1-4}$haloalkyl;

is:

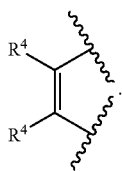

A is a group of formula (a):

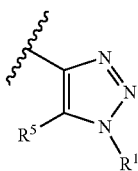

(a)

where:
R$^1$ is a 5-, 6-, 7-, or 8-membered saturated, partially saturated or unsaturated monocyclic, a saturated, partially saturated or unsaturated 8-, 9-, 10- or 11-membered bicyclic, or 12-, 13-, 14- or 15-membered tricyclic hydrocarbon ring containing 0, 1, 2, 3 or 4 atoms selected from N, O and S, wherein the carbon and sulfur atoms of the ring are substituted by 0, 1 or 2 oxo groups and the ring is substituted by 0, 1, 2 or 3 substituents selected from R$^6$, R$^7$ or R$^8$ independently selected from basic moieties, and additionally substituted by 0, 1, 2 or 3 substituents selected from R$^6$, R$_7$ and R$^8$ which are selected from R$^g$, C$_{1-8}$alkyl, C$_{1-4}$haloalkyl, hydroxyalkyl, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and the ring is additionally substituted by 0, 1, 2, 3, 4 or 5 substituents selected from R$^6$, R$_7$, R$^8$, R$^9$ and R$^{10}$ which are independently selected from Br, Cl, F and I;

R$^2$ is a saturated, partially saturated or unsaturated 5-, 6- or 7-membered monocyclic or 6-, 7-, 8-, 9-, 10- or 11-membered bicyclic hydrocarbon ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from R$^e$, R$^g$, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$ and —NR$^a$C$_{2-6}$alkylOR$^a$, and the ring is additionally substituted by 0, 1, 2, 3, 4 or 5 substituents independently selected from Br, Cl, F and I;

R$^3$, R$^{3a}$, R$^4$ and R$^5$ are independently in each instance selected from H, C$_{1-3}$alkyl, C$_{1-3}$haloalkyl, —OH, F, Cl, Br and I; or R$^3$ and R$^{3a}$ together form oxo;

R$^x$ is selected from H, F, Cl, (C$_1$-C$_3$)haloalkyl, and (C$_1$-C$_3$)alkyl;

R$^a$ is independently, at each instance, H or R$^b$;

R$^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl.

R$^d$ is independently at each instance C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$_a$C$_{2-6}$-alkyl-NR$^a$R$^a$ or —NR$_a$C$_{2-6}$alkylOR$^a$;

R$^e$ is independently at each instance C$_{1-6}$alkyl substituted by 0, 1, 2 or 3 substituents independently selected from R$^d$ and additionally substituted by 0 or 1 substituents selected from R$^g$; and R$^g$ is independently at each instance a saturated, partially saturated or unsaturated 5-, 6- or 7-membered monocyclic or 6-, 7-, 8-, 9-, 10- or 11-membered bicyclic hydrocarbon ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from C$_{1-8}$alkyl, C$_{1-4}$haloalkyl, halo, cyano, nitro, —C(=O)R$^b$—C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and the ring is additionally substituted by 0, 1, 2, 3, 4 or 5 substituents independently selected from Br, Cl, F and I;

or a pharmaceutically-acceptable salt thereof;

wherein the basic moieties are independently selected from amino, cycloalkylaminoC$_{1-6}$alkyl, cycloalkylC$_{1-6}$alkylamino-C$_{1-6}$alkyl, heterocyclylaminoC$_{1-6}$alkyl, heterocyclylC$_{1-6}$alkylaminoC$_{1-6}$alkyl, arylaminoC$_{1-6}$alkyl, arylC$_{1-6}$alkylaminoC$_{1-6}$alkyl, C$_{1-6}$-alkylamino-C$_{1-6}$- alkoxy, $C_{1-6}$-alkylamino-$C_{1-6}$-alkoxy-$C_{1-6}$-alkoxy, amino$C_{1-6}$alkoxy, amino$C_{1-6}$alkyl, $C_{1-6}$alkylamino$C_{1-6}$alkyl, $C_{1-4}$-alkylamino-$C_{2-6}$-alkenyl, 5-8 membered nitrogen-containing heterocyclyl-$C_{2-6}$-alkenyl, heterocyclyl-$C_{1-6}$alkylamino-$C_{2-6}$alkyl, 5-6 membered heterocyclyloxy, 4-6 membered nitrogen-containing heterocyclyl and 5-7 membered nitrogen-containing heterocyclyl-alkyl; and wherein each of said basic moieties is substituted by 0, 1, 2 or 3 groups independently selected from halo, —NH$_2$, hydroxyl, cyano, —CF$_3$, $C_{1-6}$alkylamino, oxo, $C_{1-6}$alkoxy, $C_{2-6}$alkenyl, $C_{2-6}$alkynyl, di$C_{1-6}$alkylamino, $C_{1-6}$alkyl, substituted $C_{1-6}$alkyl, aryl, substituted aryl, heteroaryl, substituted heteroaryl, cycloalkyl, substituted cycloalkyl, substituted saturated or partially saturated heterocyclyl and unsubstituted saturated or partially saturated heterocyclyl, wherein each substituted $C_{1-6}$alkyl, substituted aryl, substituted heteroaryl, and substituted saturated or partially saturated heterocyclyl is substituted by 0, 1, 2 or 3 groups independently selected from halo, —NH$_2$, hydroxyl, cyano, $C_{1-6}$alkylamino, $C_{1-6}$haloalkyl, oxo, $C_{1-6}$alkoxy, $C_{1-6}$alkoxy$C_{1-6}$alkyl, $C_{1-6}$alkyl, $C_{2-6}$alkenyl, $C_{2-6}$alkynyl, or di$C_{1-6}$alkylamino.

2. The compound of claim 1 wherein $R^1$ is a saturated, partially saturated or unsaturated 8-, 9-, 10- or 11-membered bicyclic or 12-, 13-, 14- or 15-membered tricyclic hydrocarbon ring containing 0, 1, 2, 3 or 4 atoms selected from N, O and S, wherein the carbon and sulfur atoms of the ring are substituted by 0, 1 or 2 oxo groups and the ring is substituted by $R^6$, $R_7$ or $R^8$ independently selected from basic moieties, and additionally substituted by 0, 1, 2 or 3 substituents selected from $R^6$, $R^7$ and $R^8$ which are selected from $R^g$, $C_{1-8}$alkyl, $C_{1-4}$haloalkyl, cyano, nitro, —C(=O)$R^b$, —C(=O)O$R^b$, —C(=O)NR$^a$R$^a$, —C(=NR$^a$)NR$^a$R$^a$, —OR$^a$, —OC(=O)$R^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and the ring is additionally substituted by 0, 1, 2, 3, 4 or 5 substituents selected from $R^6$, $R^7$, $R^8$, $R^9$ and $R^{10}$ which are independently selected from Br, Cl, F and I; and $R^x$ is H.

3. The compound of claim 2 wherein and $R^3$ and $R^{3a}$ together form oxo.

4. The compound of claim 3 wherein:

$R^5$ is hydrogen; and $R^1$ is:

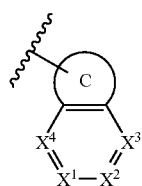

wherein:

$X^1$ is N or CR$^6$;

$X^2$ is N or CR$^7$;

$X^3$ is N or CR$^8$;

$X^4$ is N or CH; wherein no more than two of $X^1$, $X^2$, $X^3$ and $X^4$ is N; and the C ring is a saturated or partially saturated 6- or 7-membered ring containing 0, 1 or 2 atoms selected from N, O and S, wherein the carbon and sulfur atoms of the ring are substituted by 0, 1 or 2 oxo groups and the ring is substituted by 0 or 1 substituents selected from $R^g$, $C_{1-8}$alkyl, $C_{1-4}$haloalkyl, cyano, nitro, —C(=O)$R^b$, —C(=O)O$R^b$, —C(=O)NR$^a$R$^a$, —C(=NR$^a$)NR$^a$R$^a$, —OR$^a$, —OC(=O)$R^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and the ring is additionally substituted by 0, 1, 2 or 3 substituents independently selected from Br, Cl, F and I.

5. The compound of claim 3 wherein:

$R^5$ is hydrogen;

$R^1$ is:

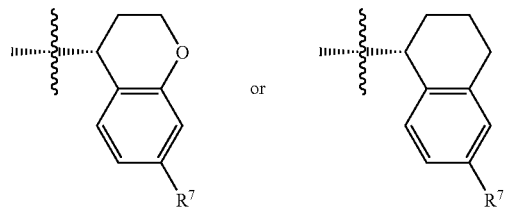

where $R^7$ is a basic moiety; and

X is —NH—.

6. The compound of claim 5 wherein $R^7$ is selected from amino, aminomethyl, isopropylaminomethyl, t-butylaminomethyl, 2-t-butylaminoethyl, 2-tert-butylamino-1-methylethyl, 1-tert-butylaminoethyl, 1-(tert-butylamino-methyl)-vinyl, 1-(piperidin-1-ylmethyl)-vinyl, N-isobutylaminomethyl, N-isobutyl-aminoethyl, (2,2-dimethyl)propylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)-aminomethyl, N,N-dimethylaminomethyl, N,N-diethylaminomethyl, N,N-di(t-butyl)-aminomethyl, cyclopropylaminomethyl, cyclopropylaminoethyl, cyclopropylmethyl-aminomethyl, cyclopropylmethylaminoethyl, cyclobutylaminomethyl, cyclobutylaminoethyl, cyclobutylmethylaminomethyl, cyclobutylmethylaminoethyl, 4,5-dihydro-imidazolyl, 1-piperidinylmethyl, 4-fluoropiperidin-1-ylmethyl, 4,4-difluoropiperidin-1-ylmethyl, 3-hydroxypiperidin-1-ylmethyl, 4-hydroxypiperidin-1-ylmethyl, 4-(piperidin-1-yl)-piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethyl-pyrrolidin-1-ylmethyl, piperazin-1-ylmethyl, azocan-1-ylmethyl, azepan-1-ylmethyl, (7-azabicyclo[2.2.1]hept-7-yl)methyl, (1,3,3-trimethyl-6-azabicyclo[3.2.1]oct-6-yl)methyl, 2-piperidinyl and 4-methylpiperazin-1-ylmethyl; and $R^2$ is phenyl substituted by 1, 2 or 3 substituents selected $C_{1-6}$alkyl, $C_{1-4}$haloalkyl, halo, cyano, or nitro.

7. A compound selected from the group consisting of:

(R)-3-((1-((R)-7-cyclopropylaminomethyl-3,4-dihydro-2H-chromen-4-yl)-1H-1,2,3-triazol-4-yl)methyl)-4-(4-methylbenzenesulfonyl)-3,4-dihydropyrazin-2(1H)-one;

(R)-3-((1-((R)-7-tert-butylaminomethyl-3,4-dihydro-2H-chromen-4-yl)-1H-1,2,3-triazol-4-yl)methyl)-4-(4-methylbenzenesulfonyl)-3,4-dihydropyrazin-2(1H)-one;

(R)-3-((1-((R)-7-cyclopropylmethylamino-3,4-dihydro-2H-chromen-4-yl)-1H-1,2,3-triazol-4-yl)methyl)-4-(4-methylbenzenesulfonyl)-piperazin-2-one;

(R)-3-((1-((R)-6-((2,2-dimethylethylamino)methyl)-1,2,3,4-tetrahydronaphthalen-1-yl)-1H-1,2,3-triazol-4-yl)methyl)-4-(4-methylbenzenesulfonyl)-3,4-dihydropyrazin-2(1H)-one;

(R)-3-((1-((R)-6-(piperidin-1-ylmethyl)-1,2,3,4-tetrahydronaphthalen-1-yl)-1H-1,2,3-triazol-4-yl)methyl)-4-(4-methylbenzenesulfonyl)-3,4-dihydropyrazin-2(1H)-one;

(R)-4-(3,4-dichlorobenzenesulfonyl)-3-((1-((R)-1-(4-(piperidin-1-ylmethyl)phenyl)-ethyl)-1H-1,2,3-triazol-4-yl)methyl)-3,4-dihydropyrazin-2(1H)-one;

(R)-3-((1-((R)-6-((cyclopentyl-amino)methyl)-1,2,3,4-tetrahydronaphthalen-1-yl)-1H-1,2,3-triazol-4-yl)methyl)-4-tosyl-3,4-dihydropyrazin-2(1H)-one;

(R)-3-((1-((R)-6-((4-fluoro-piperidin-1-yl)methyl)-1,2,3,4-tetrahydronaphthalen-1-yl)-1H-1,2,3-triazol-4-yl)methyl)-4-(phenylsulfonyl)-3,4-dihydro-pyrazin-2(1H)-one;

(R)-4-(4-chlorophenyl-sulfonyl)-3-((1-((R)-6-((4-fluoro-piperidin-1-yl)methyl)-1,2,3,4-tetrahydronaphthalen-1-yl)-1H-1,2,3-triazol-4-yl)methyl)piperazin-2-one;

(R)-3-((1-((R)-6-((4-fluoro-piperidin-1-yl)methyl)-1,2,3,4-tetrahydronaphthalen-1-yl)-1H-1,2,3-triazol-4-yl)methyl)-4-(4-methoxyphenylsulfonyl)piperazin-2-one;

(R)-4-(4-chlorophenyl-sulfonyl)-3-((1-((R)-6-((4-fluoro-piperidin-1-yl)methyl)-1,2,3,4-tetrahydronaphthalen-1-yl)-1H-1,2,3-triazol-4-yl)methyl)-3,4-dihydropyrazin-2(1H)-one;

(R)-3-((1-((R)-6-((4-fluoro-piperidin-1-yl)methyl)-1,2,3,4-tetrahydronaphthalen-1-yl)-1H-1,2,3-triazol-4-yl)methyl)-4-(4-methoxyphenylsulfonyl)-3,4-dihydropyrazin-2(1H)-one;

(R)-3-((1-((R)-6-((cyclopentyl-amino)methyl)-1,2,3,4-tetrahydronaphthalen-1-yl)-1H-1,2,3-triazol-4-yl)methyl)-4-(phenylsulfonyl)piperazin-2-one;

(R)-3-((1-((R)-6-((cyclopentyl-amino)methyl)-1,2,3,4-tetrahydronaphthalen-1-yl)-1H-1,2,3-triazol-4-yl)methyl)-4-(3-(trifluoromethyl)phenyl-sulfonyl)-3,4-dihydropyrazin-2(1H)-one;

(R)-3-((1-((R)-6-((cyclopentyl-amino)methyl)-1,2,3,4-tetrahydronaphthalen-1-yl)-1H-1,2,3-triazol-4-yl)methyl)-4-(phenylsulfonyl)-3,4-dihydro-pyrazin-2(1H)-one;

(R)-4-(4-chlorophenyl-sulfonyl)-3-((1-((R)-6-((cyclopentyl-amino)methyl)-1,2,3,4-tetrahydronaphthalen-1-yl)-1H-1,2,3-triazol-4-yl)methyl)piperazin-2-one;

(R)-3-((1-((R)-6-((cyclopentyl-amino)methyl)-1,2,3,4-tetrahydronaphthalen-1-yl)-1H-1,2,3-triazol-4-yl)methyl)-4-(4-methoxyphenylsulfonyl)piperazin-2-one;

(R)-4-(4-chlorophenyl-sulfonyl)-3-((1-((R)-6-((cyclopentylamino)methyl)-1,2,3,4-tetra-hydronaphthalen-1-yl)-1H-1,2,3-triazol-4-yl)methyl)-3,4-dihydropyrazin-2(1H)-one;

(R)-3-((1-((R)-6-((cyclopentyl-amino)methyl)-1,2,3,4-tetrahydronaphthalen-1-yl)-1H-1,2,3-triazol-4-yl)methyl)-4-(4-methoxyphenylsulfonyl)-3,4-dihydropyrazin-2(1H)-one;

(R)-3-((1-((R)-6-((tert-butyl-amino)methyl)-1,2,3,4-tetrahydronaphthalen-1-yl)-1H-1,2,3-triazol-4-yl)methyl)-4-(phenylsulfonyl)piperazin-2-one;

(R)-3-((1-((R)-6-((tert-butyl-amino)methyl)-1,2,3,4-tetrahydronaphthalen-1-yl)-1H-1,2,3-triazol-4-yl)methyl)-4-(3-(trifluoromethyl)phenyl-sulfonyl)-3,4-dihydropyrazin-2(1H)-one;

(R)-3-((1-((R)-6-((tert-butyl-amino)methyl)-1,2,3,4-tetrahydronaphthalen-1-yl)-1H-1,2,3-triazol-4-yl)methyl)-4-(phenylsulfonyl)-3,4-dihydropyrazin-2(1H)-one;

(R)-3-((1-((R)-6-((tert-butyl-amino)methyl)-1,2,3,4-tetrahydronaphthalen-1-yl)-1H-1,2,3-triazol-4-yl)methyl)-4-(4-chlorophenylsulfony)piperazin-2-one;

(R)-3-((1-((R)-6-((tert-butyl-amino)methyl)-1,2,3,4-tetrahydronaphthalen-1-yl)-1H-1,2,3-triazol-4-yl)methyl)-4-(4-methoxyphenyl-sulfonyl)piperazin-2-one;

(R)-3-((1-((R)-6-((tert-butyl-amino)methyl)-1,2,3,4-tetrahydronaphthalen-1-yl)-1H-1,2,3-triazol-4-yl)methyl)-4-(4-chlorophenylsulfonyl)-3,4-dihydropyrazin-2(1H)-one;

(R)-3-((1-((R)-6-((tert-butyl-amino)methyl)-1,2,3,4-tetrahydronaphthalen-1-yl)-1H-1,2,3-triazol-4-yl)methyl)-4-(4-methoxyphenylsulfonyl)-3,4-dihydropyrazin-2(1H)-one;

(R)-3-((1-((R)-6-((neopentyl-amino)methyl)-1,2,3,4-tetrahydronaphthalen-1-yl)-1H-1,2,3-triazol-4-yl)methyl)-4-tosyl-3,4-dihydropyrazin-2(1H)-one;

(R)-3-((1-((R)-6-((neopentyl-amino)methyl)-1,2,3,4-tetrahydronaphthalen-1-yl)-1H-1,2,3-triazol-4-yl)methyl)-4-(phenylsulfonyl)piperazin-2-one;

(R)-3-((1-((R)-6-((neopentyl-amino)methyl)-1,2,3,4-tetrahydronaphthalen-1-yl)-1H-1,2,3-triazol-4-yl)methyl)-4-(3-(trifluoromethyl)phenyl-sulfonyl)-3,4-dihydropyrazin-2(1H)-one;

(R)-3-((1-((R)-6-((neopentyl-amino)methyl)-1,2,3,4-tetrahydronaphthalen-1-yl)-1H-1,2,3-triazol-4-yl)methyl)-4-(phenylsulfonyl)-3,4-dihydro-pyrazin-2(1H)-one;

(R)-4-(4-chlorophenylsulfonyl)-3-((1-((R)-6-((neopentylamino)methyl)-1,2,3,4-tetra-hydronaphthalen-1-yl)-1H-1,2,3-triazol-4-yl)methyl)-piperazin-2-one;

(R)-4-(4-chlorophenyl-sulfonyl)-3-((1-((R)-6-((neopentylamino)methyl)-1,2,3,4-tetra-hydronaphthalen-1-yl)-1H-1,2,3-triazol-4-yl)methyl)-3,4-dihydropyrazin-2(1H)-one;

(R)-4-(4-methoxyphenyl-sulfonyl)-3-((1-((R)-6-((neopentylamino)methyl)-1,2,3,4-tetrahydronaphthalen-1-yl)-1H-1,2,3-triazol-4-yl)methyl)-3,4-dihydro-pyrazin-2(1H)-one;

(R)-3-((1-((R)-6-((4-methyl-piperazin-1-yl)methyl)-1,2,3,4-tetrahydronaphthalen-1-yl)-1H-1,2,3-triazol-4-yl)methyl)-4-tosyl-3,4-dihydropyrazin-2(1H)-one;

(R)-3-((1-((R)-6-((4-methyl-piperazin-1-yl)methyl)-1,2,3,4-tetrahydronaphthalen-1-yl)-1H-1,2,3-triazol-4-yl)methyl)-4-(phenylsulfonyl)piperazin-2-one;

(R)-3-((1-((R)-6-((4-methyl-piperazin-1-yl)methyl)-1,2,3,4-tetrahydronaphthalen-1-yl)-1H-1,2,3-triazol-4-yl)methyl)-4-(3-(trifluoromethyl)phenylsulfonyl)-3,4-dihydropyrazin-2(1H)-one;

(R)-3-((1-((R)-6-((4-methyl-piperazin-1-yl)methyl)-1,2,
3,4-tetrahydronaphthalen-1-yl)-1H-1,2,3-triazol-4-yl)
methyl)-4-(phenylsulfonyl)-3,4-dihydropyrazin-2(1H)-
one;

(R)-4-(4-chlorophenyl-sulfonyl)-3-((1-((R)-6-((4-methylpiperazin-1-yl)methyl)-1,2,3,4-tetrahydronaphthalen-1-yl)-1H-1,2,3-triazol-4-yl)methyl)piperazin-2-one;

(R)-4-(4-methoxyphenyl-sulfonyl)-3-((1-((R)-6-((4-methylpiperazin-1-yl)methyl)-1,2,3,4-tetrahydronaphthalen-1-yl)-1H-1,2,3-triazol-4-yl)methyl)piperazin-2-one;

(R)-4-(4-chlorophenyl-sulfonyl)-3-((1-((R)-6-((4-methylpiperazin-1-yl)methyl)-1,2,3,4-tetrahydro-naphthalen-1-yl)-1H-1,2,3-triazol-4-yl)methyl)-3,4-dihydropyrazin-2(1H)-one;

(R)-4-(4-methoxyphenyl-sulfonyl)-3-((1-((R)-6-((4-methylpiperazin-1-yl)methyl)-1,2,3,4-tetrahydronaphthalen-1-yl)-1H-1,2,3-triazol-4-yl)methyl)-3,4-dihydropyrazin-2(1H)-one;

(R)-3-((1-((R)-6-((isobutyl-amino)methyl)-1,2,3,4-tetrahydronaphthalen-1-yl)-1H-1,2,3-triazol-4-yl)methyl)-4-tosyl-3,4-dihydropyrazin-2(1H)-one;

(R)-3-((1-((R)-6-((isobutyl-amino)methyl)-1,2,3,4-tetrahydronaphthalen-1-yl)-1H-1,2,3-triazol-4-yl)methyl)-4-(phenylsulfonyl)piperazin-2-one;

(R)-3-((1-((R)-6-((isobutyl-amino)methyl)-1,2,3,4-tetrahydronaphthalen-1-yl)-1H-1,2,3-triazol-4-yl)methyl)-4-(3-(trifluoromethyl)phenylsulfonyl)-3,4-dihydropyrazin-2(1H)-one;

(R)-3-((1-((R)-6-((isobutyl-amino)methyl)-1,2,3,4-tetrahydronaphthalen-1-yl)-1H-1,2,3-triazol-4-yl)methyl)-4-(phenylsulfonyl)-3,4-dihydropyrazin-2(1H1)-one;

(R)-4-(4-chlorophenyl-sulfonyl)-3-((1-((R)-6-((isobutylamino)methyl)-1,2,3,4-tetra-hydronaphthalen-1-yl)-1H-1,2,3-triazol-4-yl)methyl)piperazin-2-one;

(R)-3-((1-((R)-6-((isobutyl-amino)methyl)-1,2,3,4-tetrahydronaphthalen-1-yl)-1H-1,2,3-triazol-4-yl)methyl)-4-(4-methoxyphenylsulfonyl)piperazin-2-one;

(R)-4-(4-chlorophenyl-sulfonyl)-3-((1-((R)-6-((isobutylamino)methyl)-1,2,3,4-tetra-hydronaphthalen-1-yl)-1H-1,2,3-triazol-4-yl)methyl)-3,4-dihydropyrazin-2(1H)-one;

(R)-3-((1-((R)-6-((isobutyl-amino)methyl)-1,2,3,4-tetrahydronaphthalen-1-yl)-1H-1,2,3-triazol-4-yl)methyl)-4-(4-methoxyphenylsulfonyl)-3,4-dihydropyrazin-2(1H)-one;

(R)-3-((1-((R)-6-((4-fluoro-piperidin-1-yl)methyl)-1,2,3,4-tetrahydronaphthalen-1-yl)-1H-1,2,3-triazol-4-yl)methyl)-4-tosyl-3,4-dihydropyrazin-2(1H)-one;

(R)-3-((1-((R)-6-((4-fluoro-piperidin-1-yl)methyl)-1,2,3,4-tetrahydronaphthalen-1-yl)-1H-1,2,3-triazol-4-yl)methyl)-4-(phenylsulfonyl)piperazin-2-one;

(R)-3-((1-((R)-6-((4-fluoro-piperidin-1-yl)methyl)-1,2,3,4-tetrahydronaphthalen-1-yl)-1H-1,2,3-triazol-4-yl)methyl)-4-(3-(trifluoro-methyl)phenylsulfonyl)-3,4-dihydropyrazin-2(1H)-one;

(R)-3-((1-(4-(4,5-dihydro-1H-imidazol-2-yl)phenethyl)-1H-1,2,3-triazol-4-yl)methyl)-4-tosylpiperazin-2-one;

(R)-4-(3,4-dichlorophenylsulfonyl)-3-((1-((R)-3-isobutyl-1,2,3,4,7,8,9,10-octahydrobenzo[f]isoquinolin-7-yl)-1H-1,2,3-triazol-4-yl)methyl)-3,4-dihydropyrazin-2(1H)-one;

(R)-4-(3,4-dichlorophenylsulfonyl)-3-((1-((R)-2-isobutyl-1,2,3,4,6,7,8,9-octahydro-benzo[g]isoquinolin-6-yl)-1H-1,2,3-triazol-4-yl)methyl)-3,4-dihydropyrazin-2(1H)-one;

(R)-2-((1-((R)-6-(piperidin-1-ylmethyl)-1,2,3,4-tetrahydronaphthalen-1-yl)-1H-1,2,3-triazol-4-yl)methyl)-1-tosyl-1,2-dihydropyrido[2,3-b]pyrazin-3(4H)-one;

(R)-3-((1-((R)-6-chloro-1,1-dioxothiochroman-4-yl)-1H-1,2,3-triazol-4-yl)methyl)-4-(3,4-dichlorophenylsulfonyl)-3,4-dihydropyrazin-2(1H)-one;

(R)-4-(3,4-dichlorophenyl-sulfonyl)-3-((1-((R)-1,2,3,4,7,8,9,10-octahydro-benzo[f]isoquinolin-7-yl)-1H-1,2,3-triazol-4-yl)methyl)-3,4-dihydropyrazin-2(1H)-one;

(R)-4-(3,4-dichlorophenyl-sulfonyl)-3-((1-((R)-1,2,3,4,6,7,8,9-octahydro-benzo[g]isoquinolin-6-yl)-1H-1,2,3-triazol-4-yl)methyl)-3,4-dihydropyrazin-2(1H)-one;

(R)-4-(3,4-dichlorophenyl-sulfonyl)-3-((1-((R)-3-isobutyl-1,2,3,4,7,8,9,10-octahydro-benzo[f]isoquinolin-7-yl)-1H-1,2,3-triazol-4-yl)methyl)-3,4-dihydropyrazin-2(1H)-one;

(S)-4-(3,4-dichlorophenyl-sulfonyl)-3-((1-((S)-2-(2-(piperidin-1-yl)ethyl)-5,6,7,8-tetrahydroquinazolin-5-yl)-1H-1,2,3-triazol-4-yl)methyl)-3,4-dihydropyrazin-2(1H)-one;

(R)-4-(3,4-dichlorophenyl-sulfonyl)-3-((1-((S)-2-(2-(piperidin-1-yl)ethyl)-5,6,7,8-tetrahydroquinazolin-5-yl)-1H-1,2,3-triazol-4-yl)methyl)-3,4-dihydropyrazin-2(1H)-one;

(R)-4-(3,4-dichlorophenyl-sulfonyl)-3-((1-((R)-2-(2-(piperidin-1-yl)ethyl)-5,6,7,8-tetrahydroquinazolin-5-yl)-1H-1,2,3-triazol-4-yl)methyl)-3,4-dihydropyrazin-2(1H)-one;

(S)-4-(3,4-dichlorophenyl-sulfonyl)-3-((1-((R)-2-(2-(piperidin-1-yl)ethyl)-5,6,7,8-tetrahydroquinazolin-5-yl)-1H-1,2,3-triazol-4-yl)methyl)-3,4-dihydropyrazin-2(1H)-one;

(R)-methyl 5-(4-(((R)-3-oxo-1-tosylpiperazin-2-yl)methyl)-1H-1,2,3-triazol-1-yl)-5,6,7,8-tetrahydronaphthalene-2-carboxylate;

(S)-4-(3,4-dichlorophenyl-sulfonyl)-3-((1-((S)-2-(2-(4-methylpiperidin-1-yl)ethyl)-5,6,7,8-tetrahydro-quinazolin-5-yl)-1H-1,2,3-triazol-4-yl)methyl)-3,4-dihydropyrazin-2(1H)-one;

(R)-4-(3,4-dichlorophenyl-sulfonyl)-3-((1-((S)-2-(2-(4-methylpiperidin-1-yl)ethyl)-5,6,7,8-tetrahydro-quinazolin-5-yl)-1H-1,2,3-triazol-4-yl)methyl)-3,4-dihydropyrazin-2(1H)-one;

(S)-4-(3,4-dichlorophenyl-sulfonyl)-3-((1-((R)-2-(2-(4-methylpiperidin-1-yl)ethyl)-5,6,7,8-tetrahydro-quinazolin-5-yl)-1H-1,2,3-triazol-4-yl)-methyl)-3,4-dihydropyrazin-2(1H)-one;

(R)-4-(3,4-dichlorophenyl-sulfonyl)-3-((1-((R)-2-(2-(4-methylpiperidin-1-yl)ethyl)-5,6,7,8-tetrahydro-quinazolin-5-yl)-1H-1,2,3-triazol-4-yl)-methyl)-3,4-dihydropyrazin-2(1H)-one;

(R)-3-((1-((R)-6-(((S)-2-(hydroxymethyl)pyrrolidin-1-yl)methyl)-1,2,3,4-tetrahydronaphthalen-1-yl)-1H-1,2,3-triazol-4-yl)methyl)-4-tosyl-3,4-dihydropyrazin-2(1H)-one;

(R)-3-((1-((R)-6-(((R)-2-(hydroxymethyl)pyrrolidin-1-yl)methyl)-1,2,3,4-tetrahydro-naphthalen-1-yl)-1H-1,2,3-triazol-4-yl)methyl)-4-tosyl-3,4-dihydropyrazin-2(1H)-one;

(R)-3-((1-((R)-6-(piperidin-1-ylmethyl)-1,2,3,4-tetrahydro-naphthalen-1-yl)-1H-1,2,3-triazol-4-yl)methyl)-4-tosyl-3,4-dihydropyrazin-2(1H)-one;

(R)-2-((1-((R)-6-(piperidin-1-ylmethyl)-1,2,3,4-tetrahydro-naphthalen-1-yl)-1H-1,2,3-triazol-4-yl)methyl)-1-tosyl-1,2-dihydropyrido[2,3-b]pyrazin-3(4H)-one;

(R)-3-((1-((R)-6-(piperidin-1-ylmethyl)-1,2,3,4-tetrahydro-naphthalen-1-yl)-1H-1,2,3-triazol-4-yl)methyl)-4-tosyl-3,4-dihydropyrido[3,2-b]pyrazin-2(1H)-one;

(R)-4-(3,4-dichlorophenyl-sulfonyl)-3-((3-((R)-6-(piperidin-1-ylmethyl)-1,2,3,4-tetrahydronaphthalen-1-yl)-3H-1,2,3-triazol-4-yl)methyl)-3,4-dihydropyrazin-2(1H)-one;

(R)-4-(3,4-dichlorophenyl-sulfonyl)-3-((1-((R)-6-(piperidin-1-ylmethyl)-1,2,3,4-tetrahydronaphthalen-1-yl)-1H-1,2,3-triazol-4-yl)methyl)-3,4-dihydropyrazin-2(1H)-one;

methyl 4-((R)-1-(4-(((R)-1-(3,4-dichlorophenylsulfonyl)-3-oxo-1,2,3,4-tetrahydropyrazin-2-yl)methyl)-1H-1,2,3-triazol-1-yl)ethyl)benzoate;

(R)-methyl 5-(4-(((R)-1-(3,4-dichlorophenylsulfonyl)-3-oxo-1,2,3,4-tetrahydropyrazin-2-yl)methyl)-1H-1,2,3-triazol-1-yl)-5,6,7,8-tetrahydro-naphthalene-2-carboxylate;

(R)-3-((1-(4-(4,5-dihydro-1H-imidazol-2-yl)phenethyl)-1H-1,2,3-triazol-4-yl)methyl)-4-tosylpiperazin-2-one;

(R)-3-((1-(4-(4H-1,2,4-triazol-3-yl)phenethyl)-1H-1,2,3-triazol-4-yl)methyl)-4-tosylpiperazin-2-one;

(R)-3-((1-(4-(4,5-dihydro-1H-imidazol-2-yl)phenethyl)-1H-1,2,3-triazol-4-yl)methyl)-4-tosyl-3,4-dihydropyrazin-2(1H)-one;

(R)-3-((1-(4-(4,5-dihydro-1H-imidazol-2-yl)phenethyl)-1H-1,2,3-triazol-4-yl)methyl)-4-(4-methoxyphenylsulfonyl)piperazin-2-one;

(R)-3-((1-((R)-6-(((S)-2-(hydroxymethyl)pyrrolidin-1-yl)methyl)-1,2,3,4-tetrahydronaphthalen-1-yl)-1H-1,2,3-triazol-4-yl)methyl)-4-tosylpiperazin-2-one;

(R)-3-((1-((R)-6-(((R)-2-(hydroxymethyl)pyrrolidin-1-yl)methyl)-1,2,3,4-tetrahydronaphthalen-1-yl)-1H-1,2,3-triazol-4-yl)methyl)-4-tosylpiperazin-2-one;

(R)-4-(3,4-dichlorophenyl-sulfonyl)-3-((1-((R)-3-(2,2,2-trifluoroacetyl)-,2,3,4,7,8,9,10-octahydrobenzo[f]isoquinolin-7-yl)-1H-1,2,3-triazol-4-yl)methyl)-3,4-dihydropyrazin-2(1H)-one;

(R)-4-(3,4-dichlorophenyl-sulfonyl)-3-((1-((R)-2-(2,2,2-trifluoroacetyl)-,2,3,4,7,8,9,10-octahydrobenzo[h]isoquinolin-7-yl)-1H-1,2,3-triazol-4-yl)methyl)-3,4-dihydropyrazin-2(1H)-one;

(R)-4-(3,4-dichlorophenyl-sulfonyl)-3-((1-((R)-2-isobutyl-1,2,3,4,6,7,8,9-octahydro-benzo[g]isoquinolin-6-yl)-1H-1,2,3-triazol-4-yl)methyl)-3,4-dihydropyrazin-2(1H)-one;

(R)-3-((1-((S)-2-(2-(azepan-1-yl)ethyl)-5,6,7,8-tetrahydro-quinazolin-5-yl)-1H-1,2,3-triazol-4-yl)methyl)-4-(3,4-dichloro-phenylsulfonyl)-3,4-dihydro-pyrazin-2(1H)-one;

(R)-3-((1-((R)-2-(2-(azepan-1-yl)ethyl)-5,6,7,8-tetrahydro-quinazolin-5-yl)-1H-1,2,3-triazol-4-yl)methyl)-4-(3,4-dichloro-phenylsulfonyl)-3,4-dihydro-pyrazin-2(1-H)-one;

4-(naphthalen-2-ylsulfonyl)-3-((1-(7-(2-piperidin-1-ylethyl)chroman-4-yl)-1H-1,2,3-triazol-4-yl)methyl)-3,4-dihydropyrazin-2(1H)-one;

4-(naphthalen-2-ylsulfonyl)-3-((1-(7-(dimethylaminomethyl)chroman-4-yl)-1H-1,2,3-triazol-4-yl)methyl)-3,4-dihydropyrazin-2(1H)-one;

4-(naphthalen-2-ylsulfonyl)-3-((1-(7-(piperidin-1-ylmethyl)chroman-4-yl)-1H-1,2,3-triazol-4-yl)methyl)-3,4-dihydropyrazin-2(1H)-one;

4-(naphthalen-2-ylsulfonyl)-3-((1-(7-(4-methylpiperazin-1-ylmethyl)chroman-4-yl)-1H-1,2,3-triazol-4-yl)methyl)-3,4-dihydropyrazin-2(1H)-one;

4-(naphthalen-2-ylsulfonyl)-3-((1-(7-(diethylaminomethyl)chroman-4-yl)-1H-1,2,3-triazol-4-yl)methyl)-3,4-dihydropyrazin-2(1H)-one;

4-(naphthalen-2-ylsulfonyl)-3-((1-(7-(4,5-dihydroimidazol-2-ylmethyl)chroman-4-yl)-1H-1,2,3-triazol-4-yl)methyl)-3,4-dihydropyrazin-2(1H)-one;

4-(naphthalen-2-ylsulfonyl)-3-((1-(7-(2-ethylmethylaminoethyl)chroman-4-yl)-1H-1,2,3-triazol-4-yl)methyl)-3,4-dihydropyrazin-2(1H)-one;

4-(naphthalen-2-ylsulfonyl)-3-((1-(7-(2-piperazin-1-ylethyl)chroman-4-yl)-1H-1,2,3-triazol-4-yl)methyl)-3,4-dihydropyrazin-2(1H)-one;

3-((1-(7-((isopropyl(methyl)amino)methyl)chroman-4-yl)-1H-1,2,3-triazol-4-yl)methyl)-4-(5,6,7,8-tetrahydronaphth-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2-quinolyl sulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(phenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2-chlorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-chlorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(4-chlorophenylsulfonylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(4-methoxyphenylsulfonyl ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3,5-dichlorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-methoxyphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-fluorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(biphen-3-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(biphen-4-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-methylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-trifluoromethylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,3,4-trichlorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,4,5-trichlorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3,4-dichlorophenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(4-t-butylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(naphtha-1-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(4-methylnaphth-1-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(phenylethen-1-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(benzo[1,2,5]oxadiazol-5-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-(dimethylamino)naphth-1-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-chloro-3-methylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(benzothiazol-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,3,4,5,6-pentamethylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(6-methoxy-2-naphthylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-chloro-4-methylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-methoxy-3-methylbenzothien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(6-methoxy-3-methylbenzothien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-chloro-3-methylbenzothien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-methylbenzothien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,4-dichloro-5-methylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3,5-dichloro-4-methylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,4-dichloro-3-methylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(7-methoxy-2-naphthylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(6-fluoroethoxy-2-naphthylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-methyl-5-trifluoromethoxybenzofur-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-methyl-5-methoxybenzofur-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-chloro-benzo[1,2,5]oxadiazol-4-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-methyl-5-trifluoromethoxybenzothien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(6-ethoxy-2-naphthylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2-Cl4-$CF_3$-phenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(6-bromonaphth-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-methylbenzofur-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3-chlorobenzothien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-chloro-benzo[1,2,5]thiadiazol-4-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-chloro-1,3-dimethyl-1H-pyrazol-4-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,3-dichlorothien-5-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,5-dichlorothien-3-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-chloro-2-naphthylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(4-butoxyphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(3,5-di(trifluoromethyl)phenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(5-(isoxazol-3-yl)thien-2-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2-chlorothien-5-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(4-chloro-benzo[1,2,5]oxadiazol-7-ylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,4-dichloro-6-methylphenylsulfonyl)-3,4-dihydropyrazin-2(1H)-one;

3-((1-(7-((isopropyl(methyl)amino)methyl)chroman-4-yl)-1H-1,2,3-triazol-4-yl)methyl)-4-(2,4,6-trimethylphenylsulfonyl)-3,4-dihydropyrazin-2(1H)-one;
3-((1-(7-((isopropyl(methyl)amino)methyl)chroman-4-yl)-1H-1,2,3-triazol-4-yl)methyl)-4-(2,5-dimethylphenylsulfonyl)-3,4-dihydropyrazin-2(1H)-one;
3-((1-(7-((isopropyl(methyl)amino)methyl)chroman-4-yl)-1H-1,2,3-triazol-4-yl)methyl)-4-(4-chloro-2,5-dimethylphenylsulfonyl)-3,4-dihydropyrazin-2(1H)-one;
3-((1-(7-((isopropyl(methyl)amino)methyl)chroman-4-yl)-1H-1,2,3-triazol-4-yl)methyl)-4-(2,5-dichlorophenylsulfonyl)-3,4-dihydropyrazin-2(1H)-one;
3-((1-(7-((isopropyl(methyl)amino)methyl)chroman-4-yl)-1H-1,2,3-triazol-4-yl)methyl)-4-(4-chloro-2,5-dimethylphenylsulfonyl)-3,4-dihydropyrazin-2(1H)-one;
3-((1-(7-((isopropyl(methyl)amino)methyl)chroman-4-yl)-1H-1,2,3-triazol-4-yl)methyl)-4-(3,4-difluorophenylphenylsulfonyl)-3,4-dihydropyrazin-2(1H)-one;
3-((1-(7-((isopropyl(methyl)amino)methyl)chroman-4-yl)-1H-1,2,3-triazol-4-yl)methyl)-4-(3-chloro-4-fluorophenylsulfonyl)-3,4-dihydropyrazin-2(1H)-one;
3-((1-(7-((isopropyl(methyl)amino)methyl)chroman-4-yl)-1H-1,2,3-triazol-4-yl)methyl)-4-(2-methyl-5-trifluoromethylphenylsulfonyl)-3,4-dihydropyrazin-2(1H)-one;
3-((1-(7-((isopropyl(methyl)amino)methyl)chroman-4-yl)-1H-1,2,3-triazol-4-yl)methyl)-4-(4-methylcyclohexylsulfonyl)-3,4-dihydropyrazin-2(1H)-one;
3-((1-(7-((isopropyl(methyl)amino)methyl)chroman-4-yl)-1H-1,2,3-triazol-4-yl)methyl)-4-(3,5-dimethylbenzothien-2-ylsulfonyl)-3,4-dihydropyrazin-2(1H)-one;
3-((1-(7-((isopropyl(methyl)amino)methyl)chroman-4-yl)-1H-1,2,3-triazol-4-yl)methyl)-4-(5-fluoro-3-methylbenzothien-2-ylsulfonyl)-3,4-dihydropyrazin-2(1H)-one;
3-((1-(7-((isopropyl(methyl)amino)methyl)chroman-4-yl)-1H-1,2,3-triazol-4-yl)methyl)-4-(5-methylbenzothien-2-ylsulfonyl)-3,4-dihydropyrazin-2(1H)-one;
3-((1-(7-((isopropyl(methyl)amino)methyl)chroman-4-yl)-1H-1,2,3-triazol-4-yl)methyl)-4-(5-chloro-3-methylbenzofur-2-ylsulfonyl)-3,4-dihydropyrazin-2(1H)-one;
3-((1-(7-((isopropyl(methyl)amino)methyl)chroman-4-yl)-1H-1,2,3-triazol-4-yl)methyl)-4-(3-pyridylsulfonyl)-3,4-dihydropyrazin-2(1H)-one;
3-((1-(3-isopropyl-7-(1-methylpiperidin-2-yl)chroman-4-yl)-1H-1,2,3-triazol-4-yl)methyl)-4-(3-trifluoromethylphenylsulfonyl)-3,4-dihydropyrazin-2(1H)-one;
3-((1-(2,2-dimethyl-7-(1-methylpiperidin-2-yl)chroman-4-yl)-1H-1,2,3-triazol-4-yl)methyl)-4-(3-trifluoromethylphenylsulfonyl)-3,4-dihydropyrazin-2(1H)-one;
3-((1-(7-(piperidin-2-yl)chroman-4-yl)-1H-1,2,3-triazol-4-yl)methyl)-4-(3-trifluoromethylphenylsulfonyl)-3,4-dihydropyrazin-2(1H)-one;
3-((1-(2,2-dimethyl-7-(methylaminomethyl)chroman-4-yl)-1H-1,2,3-triazol-4-yl)methyl)-4-(3-trifluoromethylphenylsulfonyl)-3,4-dihydropyrazin-2(1H)-one;
3-((1-(7-(dimethylaminomethyl)-1,2,3,4-tetrahydonaphth-4-yl)-1H-1,2,3-triazol-4-yl)methyl)-4-(3-trifluoromethylphenylsulfonyl)-3,4-dihydropyrazin-2(1H)-one;
3-((1-(7-(piperidin-1-ylaminomethyl)-1,2,3,4-tetrahydonaphth-2-yl)-1H-1,2,3-triazol-4-yl)methyl)-4-(3-trifluoromethylphenylsulfonyl)-3,4-dihydropyrazin-2(1H)-one;
3-((1-(5-(piperidin-1-yl)methylindan-1-yl)-1H-1,2,3-triazol-4-yl)methyl)-4-(3-trifluoromethylphenylsulfonyl)-3,4-dihydropyrazin-2(1H)-one;
3-((1-(6-(4-methylpiperazin-1-yl)methylindan-1-yl)-1H-1,2,3-triazol-4-yl)methyl)-4-(3-trifluoromethylphenylsulfonyl)-3,4-dihydropyrazin-2(1H)-one;
3-((1-(4-(piperazin-1-yl)methylindan-1-yl)-1H-1,2,3-triazol-4-yl)methyl)-4-(3-trifluoromethylphenylsulfonyl)-3,4-dihydropyrazin-2(1H)-one;
3-((1-(2-(diethylaminomethyl)-5,6,7,8-tetrahydoquinolin-5-yl)-1H-1,2,3-triazol-4-yl)methyl)-4-(3-trifluoromethylphenylsulfonyl)-3,4-dihydropyrazin-2(1H)-one;
3-((1-(2-(isopropylaminomethyl)-5,6,7,8-tetrahydoquinolin-8-yl)-1H-1,2,3-triazol-4-yl)methyl)-4-(3-trifluoromethylphenylsulfonyl)-3,4-dihydropyrazin-2(1H)-one;
3-((1-(2-(t-butylaminomethyl)-5,6,7,8-tetrahydoisoquinolin-8-yl)-1H-1,2,3-triazol-4-yl)methyl)-4-(3-trifluoromethylphenylsulfonyl)-3,4-dihydropyrazin-2(1H)-one;
3-((1-(7-(morpholin-4-ylmethyl)-quinolin-4-yl)-1H-1,2,3-triazol-4-yl)methyl)-4-(3-trifluoromethylphenylsulfonyl)-3,4-dihydropyrazin-2(1H)-one;
3-((1-(1-methyl-2-oxo-6-(piperidin-1-yl)methylindol-3-yl)-1H-1,2,3-triazol-4-yl)methyl)-4-(3-trifluoromethylphenylsulfonyl)-3,4-dihydropyrazin-2(1H)-one;
3-((1-(7-(dimethylaminomethyl)-1,2,3,4-tetrahydonaphth-2-yl)-1H-1,2,3-triazol-4-yl)methyl)-4-(3-trifluoromethylphenylsulfonyl)-3,4-dihydropyrazin-2(1H)-one;
3-((1-(7-(diethylaminomethyl)-4,5,6,7-tetrahydrobenzofur-4-yl)-1H-1,2,3-triazol-4-yl)methyl)-4-(3-trifluoromethylphenylsulfonyl)-3,4-dihydropyrazin-2(1H)-one;
3-((1-(7-(4-morpholinylmethyl)-4,5,6,7-tetrahydobenzothien-4-yl)-1H-1,2,3-triazol-4-yl)methyl)-4-(3-trifluoromethylphenylsulfonyl)-3,4-dihydropyrazin-2(1H)-one;
3-((1-(7-(aminomethoxy)chroman-4-yl)-1H-1,2,3-triazol-4-yl)methyl)-4-(3-trifluoromethylphenylsulfonyl)-3,4-dihydropyrazin-2(1H)-one;
3-((1-(4-4-(4,5-dihydro-1H-imidazol-2-yl)-phenylethyl)-1H-1,2,3-triazol-4-yl)methyl)-4-(3-trifluoromethylphenylsulfonyl)-3,4-dihydropyrazin-2(1H)-one;
3-((4-4-(4,5-dihydro-1H-imidazol-2-yl)-phenyl)-1H-1,2,3-triazol-4-yl)methyl)-4-(3-trifluoromethylphenylsulfonyl)-3,4-dihydropyrazin-2(1H)-one;
3-((1-(4-(aminopropyl)phenyl)-1H-1,2,3-triazol-4-yl)methyl)-4-(3-trifluoromethylphenylsulfonyl)-3,4-dihydropyrazin-2(1H)-one; and
3-((1-(4-(aminoethyl)phenyl)-1H-1,2,3-triazol-4-yl)methyl)-4-(3-trifluoromethylphenylsulfonyl)-3,4-dihydropyrazin-2(1H)-one; or
a pharmaceutically acceptable salt thereof.

8. A pharmaceutical composition comprising a pharmaceutically acceptable carrier and a compound of claim 1.

* * * * *

UNITED STATES PATENT AND TRADEMARK OFFICE
CERTIFICATE OF CORRECTION

PATENT NO. : 7,612,060 B2 Page 1 of 1
APPLICATION NO. : 11/247046
DATED : November 3, 2009
INVENTOR(S) : Toshihiro Aya et al.

It is certified that error appears in the above-identified patent and that said Letters Patent is hereby corrected as shown below:

Column 144, line 34, delete "sulfonylsulfonyl" and insert --sulfonyl--; line 37, delete "nylsulfonyl ylsulfonyl" and insert --sulfonyl--.

Signed and Sealed this

First Day of June, 2010

David J. Kappos
*Director of the United States Patent and Trademark Office*